United States Patent
Kamioka et al.

(10) Patent No.: US 10,815,241 B2
(45) Date of Patent: Oct. 27, 2020

(54) OPTICALLY ACTIVE AZABICYCLO RING DERIVATIVE

(71) Applicant: Sumitomo Dainippon Pharma Co., Ltd., Osaka-shi (JP)

(72) Inventors: Seiji Kamioka, Osaka (JP); Hitoshi Ban, Osaka (JP); Naoaki Shimada, Osaka (JP); Wataru Hirose, Osaka (JP); Akihiko Arakawa, Odawara (JP); Kazuto Yamazaki, Ikoma (JP); Kenjiro Hira, Osaka (JP)

(73) Assignee: Sumitomo Dainippon Pharma Co., Ltd., Osaka-shi (JP)

( * ) Notice: Subject to any disclaimer, the term of this patent is extended or adjusted under 35 U.S.C. 154(b) by 0 days.

(21) Appl. No.: 16/748,191

(22) Filed: Jan. 21, 2020

(65) Prior Publication Data

US 2020/0157114 A1    May 21, 2020

Related U.S. Application Data

(63) Continuation of application No. 16/629,739, filed as application No. PCT/JP2019/033234 on Aug. 26, 2019.

(30) Foreign Application Priority Data

Aug. 27, 2018    (JP) ................. 2018-158315

(51) Int. Cl.
| | |
|---|---|
| *C07D 487/10* | (2006.01) |
| *A61P 35/00* | (2006.01) |
| *C07D 471/04* | (2006.01) |
| *A61K 31/4747* | (2006.01) |
| *A61K 45/06* | (2006.01) |

(52) U.S. Cl.
CPC ........ *C07D 487/10* (2013.01); *A61K 31/4747* (2013.01); *A61P 35/00* (2018.01); *C07D 471/04* (2013.01); *A61K 45/06* (2013.01)

(58) Field of Classification Search
CPC .................................................. C07D 487/10
See application file for complete search history.

(56) References Cited

FOREIGN PATENT DOCUMENTS

| WO | WO2017112768 | 6/2017 |
| WO | WO2017/214367 | 12/2017 |
| WO | WO 2018/050686 A1 | 3/2018 |
| WO | WO 2019/189732 A1 | 10/2019 |

OTHER PUBLICATIONS

Thomas Look, "Oncogenic Transcription Factors in the Human Acute Leukemias", Science, vol. 278, Nov. 7, 1997, pp. 1059-1064 and cover page.
Akihiko Yokoyama et al., "The Menin Tumor Suppressor Protein is an Essential Oncogenic Cofactor for MLL-Associated Leukemogenesis", Cell, vol. 123, Oct. 21, 2005, pp. 207-218.
Akihiko Yokoyama et al., "Menin Critically Links MLL Proteins with LEDGF on Cancer-Associated Target Genes", Cancer Cell, 14, Jul. 2008, pp. 36-46.
Rohit Malik et al., "Targeting the MLL Complex in Castration-Resistant Prostate Cancer", Nature Medicine, vol. 21, No. 4, Apr. 2015, pp. 344-352.
Imachi, H. et al., Breast Cancer Res Treat.122(2):395-407 (2010).
Svoboda, L.K., et al., Oncotarget. 8(1):458-471 (2017).

*Primary Examiner* — Brian E McDowell
(74) *Attorney, Agent, or Firm* — Oblon, McClelland, Maier & Neustadt, L.L.P.

(57) ABSTRACT

The present invention relates to the compound of formula (1a) wherein p is 1 or 2, $R^1$-$R^4$ are hydrogen atom or the like, and a-d are 1 or 2, or a pharmaceutically acceptable salt thereof, which has an antitumor effect by inhibiting the binding between a MLL fusion protein that is infused with AF4, AF9, or the like, which is a representative fusion partner gene causing MLL leukemia, and menin.

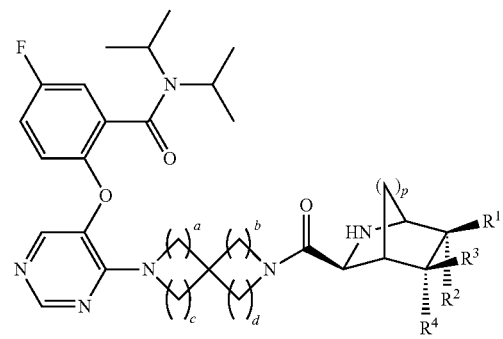

(1a)

10 Claims, 3 Drawing Sheets

OPTICALLY ACTIVE AZABICYCLO RING DERIVATIVE

This application is a continuation of application Ser. No. 16/629,739 and incorporates by reference the entire contents of application PCT/JP2019/033234, filed Aug. 26, 2019, and Japanese Patent Application 2018-158315, filed Aug. 27, 2018.

TECHNICAL FIELD

The present invention relates to an optically active azabicyclo ring derivative useful as a medicament, or a pharmaceutically acceptable salt thereof, and a pharmaceutical composition comprising it, or a medicament comprising the composition for treating or preventing conditions related to the binding between menin and MLL.

BACKGROUND ART

MLL leukemia is a disease that accounts for about 6 to 7% of acute myeloid leukemia (AML) and acute lymphoblastic leukemia (ALL), and about 1100 people are newly diagnosed with MLL leukemia each year in America. It has been reported that major fusion partner genes that cause MLL leukemia are likely to be AF9, ELL, ENL, AF10, and AF6 in AML, and AF4, ENL, and AF9 in ALL (Non-patent literature 1).

It is inferred that a MLL fusion protein fused with a fusion partner gene can cause unrestrained proliferation of undifferentiated hematopoietic cells to lead to leukemia (Non-patent literature 2). It is reported that a MLL fusion protein firstly binds to menin to form a complex. Accordingly, it is expected that canceration caused by a MLL fusion protein can be prevented by inhibiting the first binding between a MLL fusion protein and menin (Non-patent literature 3).

It is reported that MLL acts as an activation cofactor of an androgen signal in prostate cancer. Accordingly, it is expected that a small molecular inhibitor which is targeted to inhibiting the binding between menin and a MLL fusion protein is useful as a medicament for treating the cancer (Non-patent literature 4).

It is reported that menin acts as an activation cofactor of an estrogen signal in breast cancer. Accordingly, it is expected that a small molecular inhibitor which is targeted to inhibiting the binding between menin and a MLL fusion protein is useful as a medicament of the cancer (Non-patent literature 5).

It is reported that menin or MLL is important for tumor progression in Ewing's sarcoma, liver cancer, and p53 gain-of-function mutation cancer, and it is expected that a small molecular inhibitor which is targeted to inhibiting the binding between menin and a MLL fusion protein is useful as a medicament of the cancers (Non-patent literature 6).

Patent literatures 1 to 3 disclose small molecular inhibitors which are targeted to inhibiting the binding between menin and a MLL fusion protein. The present compound of the following formula (1) which is an optically active azabicyclo ring derivative, however, is not disclosed or suggested in them.

PRIOR ART

Patent Reference

[Patent Literature 1] WO 2017/112768
[Patent Literature 2] WO 2017/214367
[Patent Literature 3] WO 2018/050686

Non-Patent Reference

[Non-patent Literature 1] Look A. T, Science, 278 (5340): 1059-1064 (1997)
[Non-patent Literature 2] Yokoyama A, et al., Cell 123 (2): 207-18 (2005)
[Non-patent Literature 3] Yokoyama A, et al., Cancer Cell. 14(1): 34-46 (2008)
[Non-patent Literature 4] Malik, R. et al., Nature Medicine. 21(4):344-352 (2015)
[Non-patent Literature 5] Imacho, H et al., Breast Cancer Res Treat. 122(2):395-407 (2010)
[Non-patent Literature 6] Svoboda, L. K. et al., Oncotargrt. 8(1):458-471 (2017)

SUMMARY OF INVENTION

Technical Problem

The purpose of the present invention may be to provide a compound which has an antitumor effect by inhibiting the binding between a MLL (mixed lineage leukemia) fusion protein that is fused with AF4 or AF9, which is a representative fusion partner gene causing MLL leukemia, and menin. More preferably, the purpose of the present invention may be to provide a compound which has an antitumor effect by inhibiting the binding between menin and a MLL fusion protein, and which is expected to have high safety by having a gap between the concentration at which the compound can inhibit cell proliferation and the concentration at which the compound can inhibit hERG current. In other words, the purpose of the present invention is to provide an antitumor medicament with high therapeutic effect.

Solution to Problem

The present inventors have extensively studied to reach the above purpose, and then have found that a compound of the following formula (1) or a pharmaceutically acceptable salt thereof (hereinafter, it may be referred to as "the present compound") has an excellent antitumor effect through a potent inhibitory effect on the binding between menin and a MLL fusion protein.

Accordingly, the present invention is described as follows:

(Item 1)
A compound of formula (1):

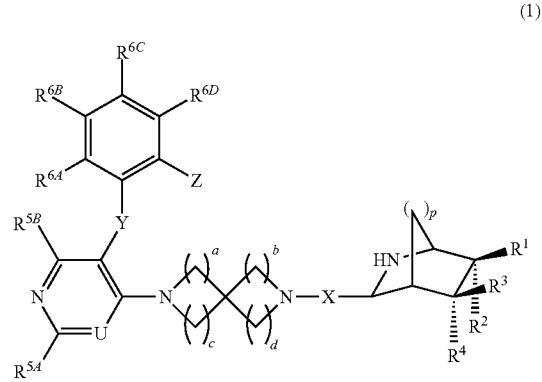

or a pharmaceutically acceptable salt thereof, wherein
p is 1 or 2;
$R^1$, $R^2$, $R^3$ and $R^4$ are each independently hydrogen atom, halogen atom, cyano, nitro, carboxyl, sulfonic acid, $-OR^7$, —$SR^7$, —$COR^8$, —$CO_2R^8$, —$CONR^9R^{10}$, —$SO_2R^8$, —$SO_2NR^9R^{10}$, —$OCOR^8$, —$OCO_2R^8$, —$OCONR^9R^{10}$, —$NR^9R^{10}$, —$NR^{11}COR^8$, —$NR^{11}CO_2R^8$, —$NR^{11}CONR^9R^{10}$, —$NR^{11}SO_2R^8$, —$NR^{11}SO_2NR^9R^{10}$, or -M-Q; or $R^1$ and $R^2$ and/or $R^3$ and $R^4$ may be combined together to form each independently =O, =$CR^{12A}R^{13A}$, =$N^{11}NR^{12B}R^{13B}$, or =N—$OR^{12B}$;

M is, each independently if there are plural, optionally-substituted $C_{1-6}$ alkylene, optionally-substituted $C_{2-6}$ alkenylene, optionally-substituted $C_{2-6}$ alkynylene, optionally-substituted $C_{3-10}$ cycloalkylene, optionally-substituted 3- to 10-membered saturated heterocyclyl, optionally-substituted $C_{6-10}$ arylene, or optionally-substituted 5- to 12-membered heteroarylene;

Q is, each independently if there are plural, hydrogen atom, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl;

$R^7$ is, each independently if there are plural, hydrogen atom, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl;

$R^8$ is, each independently if there are plural, $C_{1-6}$ alkyl;

$R^9$, $R^{10}$, and $R^{11}$ are each independently hydrogen atom or $C_{1-6}$ alkyl, and if there are plural $R^9$, $R^{10}$, or $R^{11}$, each $R^9$, $R^{10}$, or $R^{11}$ may be the same or different, or when $R^9$ and $R^{10}$ are both $C_{1-6}$ alkyl, they may be combined with the nitrogen atom to which they are each attached to form 3- to 8-membered nitrogen-containing saturated heterocycle;

$R^{12A}$ and $R^{13A}$ are each independently hydrogen atom, halogen atom, cyano, nitro, carboxyl, sulfonic acid, —$COR^{14}$, —$CO_2R^{14}$, —$CONR^{15}R^{16}$, —$SO_2R^{14}$, —$SO_2NR^{15}R^{16}$, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl, and if there are plural $R^{12A}$ or $R^{13A}$, each $R^{12A}$ or $R^{13A}$ may be the same or different, or when $R^{12A}$ and $R^{13A}$ are both optionally-substituted $C_{1-6}$ alkyl, they may be combined with the carbon atom to which they are attached to form 3- to 8-membered saturated carbocycle;

$R^{12B}$ and $R^{13B}$ are each independently hydrogen atom, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl, and if there are plural $R^{12B}$ or $R^{13B}$, each $R^{12B}$ or $R^{13B}$ may be the same or different, or when $R^{12B}$ and $R^{13B}$ are both optionally-substituted $C_{1-6}$ alkyl, they may be combined with the nitrogen atom to which they are attached to form 3- to 8-membered nitrogen-containing saturated heterocycle; $R^{14}$ is, each independently if there are plural, $C_{1-6}$ alkyl;

$R^{15}$ and $R^{16}$ are each independently hydrogen atom or $C_{1-6}$ alkyl, and if there are plural $R^{15}$ or $R^{16}$, each $R^{15}$ or $R^{16}$ may be the same or different, or when $R^{15}$ and $R^{16}$ are both $C_{1-6}$ alkyl, they may be combined with the nitrogen atom to which they are attached to form 3- to 8-membered nitrogen-containing saturated heterocycle;

X is —C(O)— or $C_{1-6}$ alkylene;

a, b, c, and d are each independently 1 or 2;

$R^{5A}$, $R^{5B}$, $R^{6A}$, $R^{6B}$, $R^{6C}$, and $R^{6D}$ are each independently hydrogen atom, halogen atom, cyano, nitro, carboxyl, sulfonic acid, —$OR^{17}$, —$SR^{17}$, —$COR^{18}$, —$CO_2R^{18}$, —$CONR^{19}R^{20}$, —$SO_2R^{18}$, —$SO_2NR^{19}R^{20}$, —$OCOR^{18}$, —$OCO_2R^{18}$, —$OCONR^{19}R^{20}$, —$NR^{19}R^{20}$, —$NR^{21}COR^{18}$, —$NR^{21}CO_2R^{18}$, —$NR^{21}CONR^{19}R^{20}$, —$NR^{21}SO_2R^{18}$, —$NR^{21}SO_2NR^{19}R^{20}$, optionally-substituted $C_{1-6}$ alkyl, optionally-substituted $C_{2-6}$ alkenyl, or optionally-substituted $C_{2-6}$ alkynyl;

$R^{17}$, $R^{19}$, $R^{20}$, and $R^{21}$ are each independently hydrogen atom or $C_{1-6}$ alkyl, and if there are plural $R^{17}$, $R^{19}$, $R^{20}$, or $R^{21}$, each $R^{17}$, $R^{19}$, $R^{20}$, or $R^{21}$ may be the same or different, or when $R^{19}$ and $R^{20}$ are both $C_{1-6}$ alkyl, they may be combined with the nitrogen atom to which they are each attached to form 3- to 8-membered nitrogen-containing saturated heterocycle;

$R^{18}$ is, each independently if there are plural, $C_{1-6}$ alkyl;

U is $CR^{22}$ or nitrogen atom;

$R^{22}$ is hydrogen atom, halogen atom, $C_{1-3}$ alkyl (which may be substituted with 1 to 5 the same or different substituents selected from fluorine atom, —$OR^{23}$ and —$NR^{23}R^{24}$), —$CO_2R^{25}$, —$CONR^{26}R^{27}$, or cyano;

$R^{23}$ and $R^{24}$ are each independently hydrogen atom or $C_{1-6}$ alkyl, and if there are plural $R^{23}$ or $R^{24}$, each $R^{23}$ or $R^{24}$ may be the same or different, or when $R^{23}$ and $R^{24}$ are both $C_{1-6}$ alkyl, they may be combined with the nitrogen atom to which they are attached to form 3- to 8-membered nitrogen-containing saturated heterocycle;

$R^{25}$ is $C_{1-6}$ alkyl;

$R^{26}$ and $R^{27}$ are each independently hydrogen atom or $C_{1-6}$ alkyl, or when $R^{26}$ and $R^{27}$ are both $C_{1-6}$ alkyl, they may be combined with the nitrogen atom to which they are attached to form 3- to 8-membered nitrogen-containing saturated heterocycle;

Y is —O—, —S—, —$CR^{28}R^{29}$—, or —$NR^{28}$—;

$R^{28}$ and $R^{29}$ are each independently hydrogen atom or $C_{1-6}$ alkyl;

Z is hydrogen atom, halogen atom, cyano, nitro, carboxyl, sulfonic acid, —$OR^{30}$, —$SR^{30}$, —$COR^{31}$, —$CO_2R^{31}$, —$CONR^{32}R^{33}$, —$SO_2R^{31}$, —$SO_2NR^{32}R^{33}$, —$OCOR^{31}$, —$OCO_2R^{31}$, —$OCONR^{32}R^{33}$, —$NR^{32}R^{33}$, —$NR^{34}COR^{31}$, —$NR^{34}CO_2R^{31}$, —$NR^{34}CONR^{32}R^{33}$, —$NR^{34}SO_2R^{31}$, —$NR^{34}SO_2NR^{32}R^{33}$, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl;

$R^{30}$, $R^{32}$, $R^{33}$, and $R^{34}$ are each independently hydrogen atom, $C_{1-6}$ alkyl (which may be substituted with 1 to 5 the same or different substituents selected from the group consisting of fluorine atom, chlorine atom, bromine atom and hydroxy), or $C_{3-10}$ cycloalkyl, or when $R^{32}$ and $R^{33}$ are both $C_{1-6}$ alkyl, they may be combined with the nitrogen atom to which they are attached to form 3- to 8-membered nitrogen-containing saturated heterocycle; and $R^{31}$ is $C_{1-6}$ alkyl optionally-substituted with 1 to 5 the same or different substituents selected from the group consisting of fluorine atom, chlorine atom, bromine atom, and hydroxy.

(Item 2)

The compound of Item 1 or a pharmaceutically acceptable salt thereof, wherein $R^1$, $R^2$, $R^3$, and $R^4$ are each independently hydrogen atom, halogen atom, —$OR^7$, or -M-Q; or $R^1$ and $R^2$ and/or $R^3$ and $R^4$ may be combined together to form each independently =O or =$CR^{12A}R^{13A}$; and $R^{12A}$ and $R^{13A}$ are each independently hydrogen atom, halogen atom, cyano, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl or optionally-substituted 5- to 12-membered heteroaryl, and if there are plural $R^{12A}$ or $R^{13A}$, each R or R may be the same or different, or when $R^{12}$ and $R^{13A}$ are both optionally-substituted $C_{1-6}$ alkyl, they may be combined with the carbon atom to which they are attached to form 3- to 8-membered saturated carbocycle.

(Item 3)

The compound of Item 1 or 2 or a pharmaceutically acceptable salt thereof, wherein the optionally-substituted $C_{1-6}$ alkylene, the optionally-substituted $C_{2-6}$ alkenylene, the optionally-substituted $C_{2-6}$ alkynylene, the optionally-substituted $C_{3-10}$ cycloalkylene, the optionally-substituted 3- to 10-membered saturated heterocyclyl, the optionally-substituted $C_{6-10}$ arylene, the optionally-substituted 5- to 12-membered heteroarylene, the optionally-substituted $C_{1-6}$ alkyl, the optionally-substituted $C_{2-6}$ alkenyl, the optionally-substituted $C_{2-6}$ alkynyl, the optionally-substituted $C_{3-10}$ cycloalkyl, the optionally-substituted $C_{6-10}$ aryl, and the optionally-substituted 5- to 12-membered heteroaryl in M, Q, Z, $R^{5A}$, $R^{5B}$, $R^{6A}$, $R^{6B}$, $R^{6C}$, $R^{6D}$, $R^7$, $R^{12A}$, $R^{12B}$, $R^{13A}$, and $R^{13B}$ may be independently substituted with 1 to 5 the same or different substituents selected from the group consisting of (1) halogen atom,
(2) hydroxy,
(3) $C_{6-10}$ aryl,
(4) 5- to 12-membered heteroaryl,
(5) $C_{1-6}$ alkyl,
(6) $C_{2-6}$ alkenyl,
(7) $C_{2-6}$ alkynyl,
(8) $C_{1-6}$ alkoxy,
(9) $C_{3-10}$ cycloalkyl,
(10) 3- to 10-membered saturated heterocyclyl,
(11) carboxyl,
(12) —$COR^{35A}$,
(13) —$CO_2R^{35A}$,
(14) —$CONR^{36A}R^{37A}$,
(15) —$NR^{36A}R^{37A}$,
(16) —$NR^{36A}COR^{35A}$,
(17) —$NR^{36A}SO_2R^{35A}$,
(18) —$SO_2R^{35A}$,
(19) —$SO_2NR^{36A}R^{37A}$,
(20) sulfonic acid,
(21) phosphoric acid,
(22) cyano, and
(23) nitro wherein the said (3) $C_{6-10}$ aryl, (4) 5- to 12-membered heteroaryl, (5) $C_{1-6}$ alkyl, (6) $C_{2-6}$ alkenyl, (7) $C_{2-6}$ alkynyl, (8) $C_{1-6}$ alkoxy, (9) $C_{3-10}$ cycloalkyl, and (10) 3- to 10-membered saturated heterocyclyl may be independently substituted with 1 to 5 the same or different substituents selected from the group consisting of (a) halogen atom,
(b) hydroxy,
(C) $C_{6-10}$ aryl,
(d) 5- to 10-membered heteroaryl,
(e) $C_{1-6}$ alkyl,
(f) $C_{2-6}$ alkenyl,
(g) $C_{2-6}$ alkynyl,
(h) $C_{1-6}$ alkoxy,
(i) $C_{3-10}$ cycloalkyl,
(j) 3- to 10-membered saturated heterocyclyl,
(k) carboxyl,
(l) —$COR^{35B}$,
(m) —$CO_2R^{35B}$,
(n) —$CONR^{36B}R^{37B}$,
(o) —$NR^{36B}R^{37B}$,
(p) —$NR^{36B}COR^{35B}$,
(q) —$NR^{36B}SO_2R^{35B}$,
(r) —$SO_2R^{35B}$,
(s) —$SO_2NR^{36B}R^{37B}$,
(t) sulfonic acid,
(u) phosphoric acid,
(v) cyano, and
(w) nitro;

$R^{35A}$ is, each independently if there are plural, $C_{1-6}$ alkyl;
$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 8-membered nitrogen-containing saturated heterocycle;

$R^{35B}$ is, each independently if there are plural, $C_{1-6}$ alkyl; and $R^{36B}$ and $R^{37B}$ are each independently hydrogen atom or $C_{1-6}$ alkyl, and if there are plural $R^{36B}$ or $R^{37B}$, each $R^{36B}$ or $R^{37B}$ may be the same or different, or when $R^{36B}$ and $R^{37B}$ are both $C_{1-6}$ alkyl, they may be combined with the nitrogen atom to which they are attached to form 3- to 8-membered nitrogen-containing saturated heterocycle.

(Item 4)

The compound of any one of Items 1 to 3 or a pharmaceutically acceptable salt thereof, wherein the optionally-substituted $C_{1-6}$ alkylene, the optionally-substituted $C_{2-6}$ alkenylene, the optionally-substituted $C_{2-6}$ alkynylene, the optionally-substituted $C_{3-10}$ cycloalkylene, the optionally-substituted 3- to 10-membered saturated heterocyclyl, the optionally-substituted $C_{6-10}$ arylene, the optionally-substituted 5- to 12-membered heteroarylene, the optionally-substituted $C_{1-6}$ alkyl, the optionally-substituted $C_{2-6}$ alkenyl, the optionally-substituted $C_{2-6}$ alkynyl, the optionally-substituted $C_{3-10}$ cycloalkyl, the optionally-substituted $C_{6-10}$ aryl, and the optionally-substituted 5- to 12-membered heteroaryl in M, Q, Z, $R^{5A}$, $R^{5B}$, $R^{6A}$, $R^{6B}$, $R^{6C}$, $R^{6D}$, $R^7$, $R^{12A}$, $R^{12B}$, $R^{13A}$, and $R^{13B}$ may be independently substituted with 1 to 5 the same or different substituents selected from the group consisting of: (1) halogen atom, (2) hydroxy,
(3) phenyl,
(4) 5- to 6-membered heteroaryl,
(5) $C_{1-6}$ alkyl optionally-substituted with 1 to 3 hydroxy,
(6) $C_{2-6}$ alkynyl,
(7) $C_{1-6}$ alkoxy,
(8) $C_{3-7}$ cycloalkyl,
(9) 3- to 7-membered saturated heterocyclyl,
(10) —$COR^{35A}$,
(11) —$CO_2R^{35A}$,
(12) —$CONR^{36A}R^{37A}$,
(13) —$NR^{36A}R^{37A}$,
(14) —$NR^{36A}COR^{35A}$,
(15) —$NR^{36A}SO_2R^{35A}$,
(16) —$SO_2R^{35A}$,
(17) —$SO_2NR^{36A}R^{37A}$,
(18) cyano, and
(19) nitro;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 5)

The compound of any one of Items 1 to 4 or a pharmaceutically acceptable salt thereof, wherein
X is —C(O)—; and
Y is —O—.

(Item 6)

The compound of any one of Items 1 to 5 or a pharmaceutically acceptable salt thereof, wherein
$R^{5A}$, $R^{5B}$, $R^{6A}$, $R^{6B}$, and $R^{6D}$ are hydrogen atom; and
$R^{6C}$ is fluorine atom.

(Item 7)

The compound of any one of Items 1 to 6 or a pharmaceutically acceptable salt thereof, wherein
U is $CR^{22}$ or nitrogen atom; and
$R^{22}$ is —$CF_3$ or cyano.

(Item 8)

The compound of any one of Items 1 to 7 or a pharmaceutically acceptable salt thereof, wherein
U is nitrogen atom.

(Item 9)

The compound of any one of Items 1 to 8 or a pharmaceutically acceptable salt thereof, wherein
Z is —$CONR^{32}R^{33}$, 3- to 6-membered saturated heterocyclyl (which may be substituted with 1 to 3 the same or different substituents selected from $C_{1-3}$ alkyl and $C_{3-6}$ cycloalkyl), phenyl (which may be substituted with 1 to 3 the same or different substituents selected from cyano, $C_{1-3}$ alkyl, and $C_{3-6}$ cycloalkyl, wherein the alkyl or the cycloalkyl may be substituted with 1 to 3 hydroxy), or 5- to 6-membered heteroaryl optionally-substituted with 1 to 3 $C_{1-3}$ alkyl; and
$R^{32}$ and $R^{33}$ are each independently hydrogen atom or $C_{1-3}$ alkyl, or when $R^{32}$ and $R^{33}$ are both $C_{1-6}$ alkyl, they may be combined with the nitrogen atom to which they are attached to form 3- to 6-membered nitrogen-containing saturated heterocycle.

(Item 10)

The compound of any one of Items 1 to 9 or a pharmaceutically acceptable salt thereof, wherein
Z is the following formula (Z-1), (Z-2), (Z-3), (Z-4), (Z-5), (Z-6), (Z-7), (Z-8), or (Z-9):

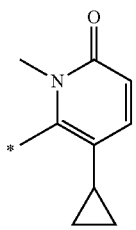

(Z-1)

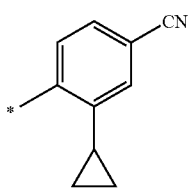

(Z-2)

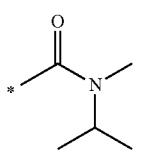

(Z-3)

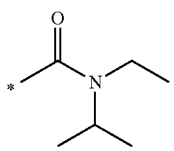

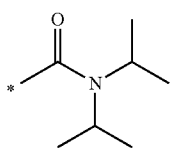

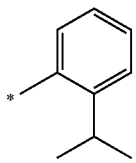

(Z-4)

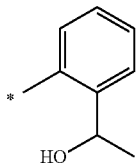

(Z-5)

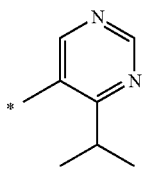

(Z-6)

(Z-7)

(Z-8)

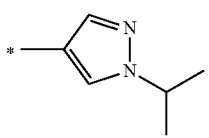

(Z-9)

wherein * is a bonding site to the aromatic ring.

(Item 11)

The compound of Item 10 or a pharmaceutically acceptable salt thereof, wherein
Z is (Z-3).

(Item 12)

The compound of any one of Items 1 to 11 or a pharmaceutically acceptable salt thereof, wherein
M is, each independently if there are plural, $C_{1-6}$ alkylene (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$ and cyano), $C_{2-6}$ alkenylene, $C_{2-6}$ alkynylene, $C_{3-10}$ cycloalkylene, 3- to 10-membered saturated heterocyclyl, $C_{6-10}$ arylene, or 5- to 12-membered heteroarylene, wherein the alkenylene, the alkynylene, the cycloalkylene, the saturated heterocyclyl, the arylene and the heteroarylene may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

Q is, each independently if there are plural, hydrogen atom, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{37A}$, —$NR^{36A}SO_2R^{35A}$, —$SO_2R^{35A}$, —$SO_2NR^{36A}R^{37A}$, and cyano;

$R^7$ is, each independently if there are plural, hydrogen atom, $C_{1-6}$ alkyl (which may be substituted with 1 to 5 the same or different substituents selected from the group consisting of fluorine atom, chlorine atom, bromine atom, hydroxy, phenyl, 5- to 6-membered heteroaryl, $C_{2-4}$ alkynyl, $C_{3-7}$ cycloalkyl, 3- to 7-membered saturated heterocyclyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^{12A}$ and $R^{13A}$ are each independently hydrogen atom, halogen atom, cyano, $C_{1-6}$ alkyl (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$ and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$ and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are attached to form 3- to 8-membered saturated carbocycle;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the same nitrogen atom to which they are attached to form 3- to 8-membered nitrogen-containing saturated heterocycle.

(Item 13)

The compound of Item 1 of formula (Ia):

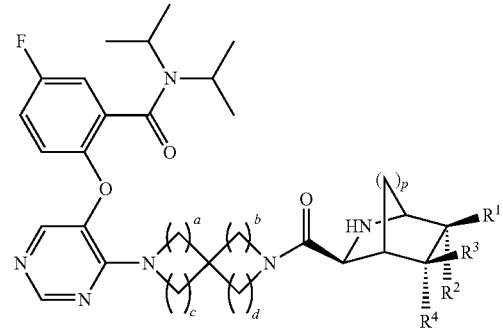

(Ia)

or a pharmaceutically acceptable salt thereof, wherein p is 1 or 2;

$R^1$, $R^2$, $R^3$, and $R^4$ are each independently hydrogen atom, halogen atom, —$OR^7$, or -M-Q; or $R^1$ and $R^2$ and/or $R^3$ and $R^4$ may be combined to form each independently =O or =$CR^{12A}R^{13A}$;

M is, each independently if there are plural, $C_{1-6}$ alkylene (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenylene, $C_{2-6}$ alkynylene, $C_{3-10}$ cycloalkylene, 3- to 10-membered saturated heterocyclyl, $C_{6-10}$ arylene, or 5- to 12-membered heteroarylene, wherein the alkenylene, the alkynylene, the cycloalkylene, the saturated heterocyclyl, the arylene, and the heteroarylene may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

Q is, each independently if there are plural, hydrogen atom, $C_{3-10}$ cycloalkyl, 3- to 10-membered saturated heterocyclyl, $C_{6-10}$ aryl or 5- to 12-membered heteroaryl, wherein the cycloalkyl, the saturated heterocyclyl, the aryl and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^7$ is, each independently if there are plural, hydrogen atom, $C_{1-6}$ alkyl (which may be substituted with 1 to 5 the same or different substituents selected from the group consisting of fluorine atom, chlorine atom, bromine atom, hydroxy, phenyl, 5- to 6-membered heteroaryl, $C_{2-4}$ alkynyl, $C_{3-7}$ cycloalkyl, 3- to 7-membered saturated heterocyclyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^{12A}$ and $R^{13A}$ are each independently hydrogen atom, halogen atom, $C_{1-6}$ alkyl (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{3SA}$, —$NR^{36A}SO_2R^{3SA}$, —$SO_2R^{35A}$, —$SO_2NR^{36A}R^{37A}$, and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are attached to form 3- to 8-membered saturated carbocycle;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle; and a, b, c, and d are each independently 1 or 2.

(Item 14)

The compound of any one of Items 1 to 13 or a pharmaceutically acceptable salt thereof, wherein M is, each independently if there are plural, $C_{1-6}$ alkylene which may be substituted with 1 to 5 the same or different substituents selected from the group consisting of fluorine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with nitrogen atom to which they are attached to form 3- to 6-membered nitrogen-containing saturated heterocycle.

[Item 15]

The compound of any one of Items 1 to 14 or a pharmaceutically acceptable salt thereof, wherein Q is, each independently if there are plural, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$ and cyano;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 16)

The compound of any one of Items 1 to 15 or a pharmaceutically acceptable salt thereof, wherein $R^7$ is, each independently if there are plural, hydrogen atom, $C_{1-6}$ alkyl (which may be substituted with 1 to 5 the same or different substituents selected from the group consisting of fluorine atom, phenyl, $C_{3-7}$ cycloalkyl, and 3- to 7-membered saturated heterocyclyl), $C_{2-6}$ alkenyl, $C_{2-6}$ alkynyl, $C_{3-10}$ cycloalkyl, 3- to 10-membered saturated heterocyclyl (wherein the cycloalkyl and the saturated heterocyclyl may be each independently substituted with 1 to 5 the same or different substituents selected from the group consisting of fluorine atom and $C_{1-3}$ alkyl), $C_{6-10}$ aryl, or 5- to 12-membered heteroaryl (wherein the aryl and the heteroaryl may be each independently substituted with 1 to 5 the same or different substituents selected from the group consisting of fluorine atom, chlorine atom, bromine atom, and $C_{1-3}$ alkyl).

(Item 17)

The compound of any one of Items 1 to 16 or a pharmaceutically acceptable salt thereof, wherein $R^7$ is, each independently if there are plural, hydrogen atom, $C_{1-6}$ alkyl, or $C_{2-6}$ alkenyl, wherein the alkyl or the alkenyl may be substituted with one phenyl.

(Item 18)

The compound of any one of Items 1 to 17 or a pharmaceutically acceptable salt thereof, wherein $R^{12A}$ and $R^{13A}$ are each independently hydrogen atom, $C_{1-6}$ alkyl (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$ and cyano), $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{37A}$, —$SO_2R^{35A}$, —$SO_2NR^{36A}R^{37A}$ and cyano, and if there are plural $R^{12A}$ or $R^{13A}$, each R or R may be the same or different, or when $R^{12A}$ and $R^{13A}$ are both $C_{1-6}$ alkyl, they may be combined with the carbon atom to which they are each attached to form 3- to 8-membered saturated carbocycle;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 19)

The compound of any one of Items 1 to 18 or a pharmaceutically acceptable salt thereof, wherein p is 1 or 2;

$R^1$, $R^2$, $R^3$, and $R^4$ are each independently hydrogen atom, halogen atom, —$OR^7$, or -M-Q; or $R^1$ and $R^2$ and/or $R^3$ and $R^4$ may be combined together to form each independently =O or =$CR^{12A}R^{13A}$;

M is, each independently if there are plural, $C_{1-6}$ alkylene which may be substituted with 1 to 3 the same or different substituents selected from the group consisting of fluorine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$ and cyano;

Q is, each independently if there are plural, $C_{3-10}$ cycloalkyl, 3- to 10-membered saturated heterocyclyl, $C_{6-10}$ aryl or 5- to 12-membered heteroaryl, wherein the cycloalkyl, the saturated heterocyclyl, the aryl, and the heteroaryl may be each independently substituted with 1 to 3 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^7$ is, each independently if there are plural, hydrogen atom, $C_{1-6}$ alkyl, or $C_{2-6}$ alkenyl, wherein the alkyl and the alkenyl may be substituted with one phenyl;

$R^{12A}$ and $R^{13A}$ are each independently hydrogen atom, $C_{1-6}$ alkyl (which may be substituted with 1 to 3 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 3 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{37A}$, —$NR^{36A}SO_2R^{35A}$, —$SO_2R^{35A}$, —$SO_2NR^{37A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are attached to form 3- to 8-membered saturated carbocycle;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle; and a, b, c and d are each independently 1 or 2.

(Item 20)

The compound of any one of Items 1 to 19 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently =O or =$CR^{12A}R^{13A}$.

(Item 21)

The compound of any one of Items 1 to 20 or a pharmaceutically acceptable salt thereof, wherein M is, each independently if there are plural, $C_{1-3}$ alkylene which may be substituted with 1 to 3 the same or different substituents selected from the group consisting of fluorine atom, $C_{2-4}$ alkynyl, $C_{1-3}$ alkoxy, —$NR^{36A}R^{37A}$, and cyano; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 22)

The compound of any one of Items 1 to 21 or a pharmaceutically acceptable salt thereof, wherein M is, each independently if there are plural, $C_{1-3}$ alkylene.

(Item 23)

The compound of any one of Items 1 to 22 or a pharmaceutically acceptable salt thereof, wherein Q is, each independently if there are plural, $C_{3-6}$ cycloalkyl, 3- to 6-membered saturated heterocyclyl, phenyl, or 5- to 6-membered heteroaryl, wherein the cycloalkyl, the saturated heterocyclyl, the phenyl, and the heteroaryl may be each independently substituted with 1 to 3 the same or different substituents selected from the group consisting of fluorine atom, chlorine atom, bromine atom, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 24)

The compound of any one of Items 1 to 23 or a pharmaceutically acceptable salt thereof, wherein Q is, each independently if there are plural, $C_{3-6}$ cycloalkyl, 3- to 6-membered saturated heterocyclyl, phenyl or 5- to 6-membered heteroaryl, wherein the cycloalkyl, the saturated heterocyclyl, the phenyl, and the heteroaryl may be each independently substituted with 1 to 3 the same or different substituents selected from the group consisting of fluorine atom, $C_{1-3}$ alkyl, —$NR^{36A}SO_2R^{35A}$, —$SO_2NR^{36A}R^{37A}$, and cyano;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 25)

The compound of any one of Items 1 to 24 or a pharmaceutically acceptable salt thereof, wherein Q is, each independently if there are plural, $C_{3-6}$ cycloalkyl which may be substituted with 1 to 3 the same or different substituents selected from the group consisting of fluorine atom, $C_{1-3}$ alkyl, —$NR^{36A}SO_2R^{35A}$, —$SO_2NR^{36A}R^{37A}$, and cyano.

(Item 26)

The compound of any one of Items 1 to 25 or a pharmaceutically acceptable salt thereof, wherein $R^{12A}$ and $R^{13A}$ are each independently hydrogen atom, $C_{1-6}$ alkyl (which may be substituted with 1 to 3 the same or different substituents selected from the group consisting of fluorine atom, $-NR^{36A}SO_2R^{35A}$, $-SO_2NR^{36A}R^{37A}$, and cyano), $C_{3-10}$ cycloalkyl (which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$ and cyano), and if there are plural $R^{12A}$ or $R^{13A}$, each $R^{12A}$ or $R^{13A}$ may be the same or different, or when $R^{12A}$ and $R^{13A}$ are both $C_{1-3}$ alkyl, they may be combined with the carbon atom to which they are attached to form 3- to 6-membered saturated carbocycle;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 27)

The compound of any one of Items 1 to 26 or a pharmaceutically acceptable salt thereof, wherein $R^{12A}$ and $R^{13A}$ are each independently hydrogen atom, or $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano, and if there are plural $R^{12A}$ and $R^{13A}$, each $R^{12A}$ and $R^{13A}$ may be the same or different;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 28)

The compound of any one of Items 1 to 27 or a pharmaceutically acceptable salt thereof, wherein a and c are 1; and both b and d are either 1 or 2.

(Item 29)

The compound of any one of Items 1 to 28 or a pharmaceutically acceptable salt thereof, wherein p is 1 or 2;

$R^1$, $R^2$, $R^3$ and $R^4$ are each independently hydrogen atom, fluorine atom, or -M-Q; or $R^1$ and $R^2$ and/or $R^3$ and $R^4$ may be combined together to form each independently =O or $=CR^{12A}R^{13A}$; M is, each independently if there are plural, $C_{1-3}$ alkylene;

Q is, each independently if there are plural, $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{12A}$ and $R^{13A}$ are each independently hydrogen atom, $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano, and if there are plural $R^{12A}$ or $R^{13A}$, each $R^{12A}$ or $R^{13A}$ may be the same or different, $R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

a and c are 1; and both b and d are either 1 or 2.

(Item 30)

The compound of any one of Items 1 to 29 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=CR^{12A}R^{13A}$.

(Item 31)

The compound of any one of Items 1 to 30 or a pharmaceutically acceptable salt thereof, wherein M is methylene.

(Item 32)

The compound of any one of Items 1 to 31 or a pharmaceutically acceptable salt thereof, wherein Q is, each independently if there are plural, $C_{3-6}$ cycloalkyl which may be substituted with 1 to 3 the same or different substituents selected from the group consisting of fluorine atom and $C_{1-3}$ alkyl.

(Item 33)

The compound of any one of Items 1 to 32 or a pharmaceutically acceptable salt thereof, wherein Q is, each independently if there are plural, $C_{3-6}$ cycloalkyl.

(Item 34)

The compound of any one of Items 1 to 33 or a pharmaceutically acceptable salt thereof, wherein $R^{12A}$ and $R^{13A}$ are each independently hydrogen atom or $C_{3-6}$ cycloalkyl.

(Item 35)

The compound of any one of Items 1 to 34 or a pharmaceutically acceptable salt thereof, wherein $R^{12A}$ and $R^{13A}$ are hydrogen atom.

(Item 36)

The compound of any one of Items 1 to 35 or a pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene;

Q is, each independently if there are plural, $C_{3-6}$ cycloalkyl;

a and c are 1; and both b and d are either 1 or 2.

(Item 37)

The compound of any one of Items 1 to 36 or a pharmaceutically acceptable salt thereof, wherein $R^1$ and $R^2$ are hydrogen atom; and $R^3$ and $R^4$ are each independently hydrogen atom or fluorine atom;

provided that both $R^3$ and $R^4$ are not hydrogen atom.

(Item 38)

The compound of any one of Items 1 to 36 or a pharmaceutically acceptable salt thereof, wherein $R^1$ and $R^2$ are each independently hydrogen atom or -M-Q; and $R^3$ and $R^4$ are each independently hydrogen atom or fluorine atom;

provided that both $R^1$ and $R^2$ are not hydrogen atom.

(Item 39)

The compound of any one of Items 1 to 36 or a pharmaceutically acceptable salt thereof, wherein $R^1$ is hydrogen atom;

$R^2$ is -M-Q;

R³ is hydrogen atom; and
R⁴ is hydrogen atom or fluorine atom.
(Item 40)
The compound of any one of Items 1 to 36 or a pharmaceutically acceptable salt thereof, wherein
R¹ is -M-Q;
R² is hydrogen atom;
R³ is hydrogen atom or fluorine atom; and
R⁴ is hydrogen atom.
(Item 41)
The compound of any one of Items 1 to 36 or a pharmaceutically acceptable salt thereof, wherein
R¹, R², R³, and R⁴ are each independently hydrogen atom; or R¹ and R² and/or R³ and R⁴ may be combined together to form =CH₂;
provided that all of R¹, R², R³ and R⁴ are not hydrogen atom.
(Item 42)
The compound of any one of Items 1 to 36 or a pharmaceutically acceptable salt thereof, wherein
R¹ and R² are combined together to form =CH₂; and
R³ and R⁴ are hydrogen atom.
(Item 43)
The compound of any one of Items 1 to 36 or a pharmaceutically acceptable salt thereof, wherein
R¹ and R² are hydrogen atom; and
R³ and R⁴ are combined together to form =CH₂.
(Item 44)
The compound of any one of Items 1 to 43 or a pharmaceutically acceptable salt thereof, wherein
a, b, c, and d are 1.
(Item 45)
The compound of any one of Items 1 to 43 or a pharmaceutically acceptable salt thereof, wherein
a and c are 1; and
b and d are 2.
(Item 46)
The compound of any one of Items 1 to 45 or a pharmaceutically acceptable salt thereof, wherein
p is 1.
(Item 47)
The compound of any one of Items 1 to 45 or a pharmaceutically acceptable salt thereof, wherein
p is 2.
(Item 48)
The compound of Item 1 or a pharmaceutically acceptable salt thereof, selected from:
2-[(4-{7-[(1S,3S,4R,6S)-6-(cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide (Example 1),
2-[(4-{6-[(1S,3S,4R,6S)-6-(cyclopropylmethyl)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl)benzamide (Example 3),
2-[(4-{7-[(1S,3S,4R,6R)-6-(cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide (Example 4),
2-[(4-{6-[(1S,3S,4R,6R)-6-(cyclopropylmethyl)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl)benzamide (Example 5),
5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (Example 6),
5-fluoro-2-[(4-{6-[(1S,3S,4R)-5-methylidene-2-azabicyclo[2.2.2]octane-3-carbonyl]-2,6-diazaspiro[3.3]heptan-2-yl}pyrimidin-5-yl)oxy]-N,N-di(propan-2-yl)benzamide (Example 7),
5-fluoro-2-[(4-{7-[(1S,3S,4R)-6-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (Example 8),
5-fluoro-2-[(4-{6-[(1S,3S,4R)-6-methylidene-2-azabicyclo[2.2.2]octane-3-carbonyl]-2,6-diazaspiro[3.3]heptan-2-yl}pyrimidin-5-yl)oxy]-N,N-di(propan-2-yl)benzamide (Example 9),
5-fluoro-2-[(4-{6-[(1S,3S,4S,5S)-5-fluoro-2-azabicyclo[2.2.2]octane-3-carbonyl]-2,6-diazaspiro[3.3]heptan-2-yl}pyrimidin-5-yl)oxy]-N,N-di(propan-2-yl)benzamide (Example 10),
2-[(4-{6-[(1R,3S,4R)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl)benzamide (Example 11),
5-fluoro-2-[(4-{7-[(1S,3S,4S)-5-oxo-2-azabicyclo[2.2.2]octane-3-carbonyl]-2,7-diazaspiro[3.5]nonan-2-yl}pyrimidin-5-yl)oxy]-N,N-di(propan-2-yl)benzamide (Example 12),
2-[(4-{7-[(1S,3S,4S,5S,6S)-6-(cyclropylmethyl)-5-fluoro-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide (Example 14),
2-[(4-{6-[(1R,3S,4S)-2-azabicyclo[2.2.1]heptane-3-carbonyl]-2,6-diazaspiro[3.3]heptan-2-yl}pyrimidin-5-yl)oxy]-5-fluoro-N,N-di(propan-2-yl)benzamide (Example 15),
2-[(4-{7-[(1R,3S,4S)-2-azabicyclo[2.2.1]heptane-3-carbonyl]-2,7-diazaspiro[3.5]nonan-2-yl}pyrimidin-5-yl)oxy]-5-fluoro-N,N-di(propan-2-yl)benzamide (Example 16),
5-fluoro-2-[(4-{7-[(1S,3S,4R)-5-methylidene-2-azabicyclo[2.2.1]heptane-3-carbonyl]-2,7-diazaspiro[3.5]nonan-2-yl}pyrimidin-5-yl)oxy]-N,N-di(propan-2-yl)benzamide (Example 18),
2-[(4-{7-[(1S,3S,4S,5R,6R)-6-(cyclopropylmethyl)-5-fluoro-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide (Example 19) and
5-fluoro-2-[(4-{7-[(1S,3S,4R)-5-(²H₂)methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (Example 20).
(Item 49)
The compound of Item 1 or a pharmaceutically acceptable salt thereof, selected from:
2-[(4-{7-[(1S,3S,4R,6S)-6-(cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide (Example 1),
2-[(4-{6-[(1S,3S,4R,6S)-6-(cyclopropylmethyl)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl)benzamide (Example 3),
2-[(4-{7-[(1S,3S,4R,6R)-6-(cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide (Example 4) and
2-[(4-{6-[(1S,3S,4R,6R)-6-(cyclopropylmethyl)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl)benzamide (Example 5).

(Item 50)

The compound of Item 1, or a hydrochloride, L(+)-tartrate or succinate thereof, selected from:

2-[(4-{7-[(1S,3S,4R,6S)-6-(cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl) benzamide (Example 1), 2-[(4-{6-[(1S,3S,4R,6S)-6-(cyclopropylmethyl)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl) benzamide (Example 3), 2-[(4-{7-[(1S,3S,4R,6R)-6-(cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl) benzamide (Example 4) and 2-[(4-{6-[(1S,3S,4R,6R)-6-(cyclopropylmethyl)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl) benzamide (Example 5).

(Item 51)

The compound of Item 1 or a pharmaceutically acceptable salt thereof, selected from:

5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (Example 6), 5-fluoro-2-[(4-{6-[(1S,3S,4R)-5-methylidene-2-azabicyclo[2.2.2]octane-3-carbonyl]-2,6-diazaspiro[3.3]heptan-2-yl}pyrimidin-5-yl)oxy]-N,N-di(propan-2-yl)benzamide (Example 7), 2-[(4-{6-[(1R,3S,4S)-2-azabicyclo[2.2.1]heptane-3-carbonyl]-2,6-diazaspiro[3.3]heptan-2-yl}pyrimidin-5-yl)oxy]-5-fluoro-N,N-di(propan-2-yl)benzamide (Example 15), 2-[(4-{7-[(1R,3S,4S)-2-azabicyclo[2.2.1]heptane-3-carbonyl]-2,7-diazaspiro[3.5]nonan-2-yl}pyrimidin-5-yl)oxy]-5-fluoro-N,N-di(propan-2-yl)benzamide (Example 16), 5-fluoro-2-[(4-{7-[(1S,3S,4R)-5-methylidene-2-azabicyclo[2.2.1]heptane-3-carbonyl]-2,7-diazaspiro[3.5]nonan-2-yl}pyrimidin-5-yl)oxy]-N,N-di(propan-2-yl)benzamide (Example 18) and 5-fluoro-2-[(4-{7-[(1S,3S,4R)-5-($^2$H$_2$)methylidene-2-azabicyclo[2.2.2]octane-3-carbonyl]-2,7-diazaspiro[3.5]nonan-2-yl}pyrimidin-5-yl)oxy]-N,N-di(propan-2-yl) benzamide (Example 20).

(Item 52)

The compound of Item 1, or a hydrochloride, L(+)-tartrate or succinate thereof, selected from:

5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (Example 6), 5-fluoro-2-[(4-{6-[(1S,3S,4R)-5-methylidene-2-azabicyclo[2.2.2]octane-3-carbonyl]-2,6-diazaspiro[3.3]heptan-2-yl}pyrimidin-5-yl)oxy]-N,N-di(propan-2-yl)benzamide (Example 7), 5-fluoro-2-[(4-{7-[(1S,3S,4R)-5-methylidene-2-azabicyclo[2.2.1]heptane-3-carbonyl]-2,7-diazaspiro[3.5]nonan-2-yl}pyrimidin-5-yl)oxy]-N,N-di(propan-2-yl)benzamide (Example 18) and 5-fluoro-2-[(4-{7-[(1S,3S,4R)-5-($^2$H$_2$)methylidene-2-azabicyclo[2.2.2]octane-3-carbonyl]-2,7-diazaspiro[3.5]nonan-2-yl}pyrimidin-5-yl)oxy]-N,N-di(propan-2-yl) benzamide (Example 20).

(Item 53)

2-[(4-{7-[(1S,3S,4R,6S)-6-(Cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide (Example 1), or a hydrochloride, L(+)-tartrate or succinate thereof.

(Item 54)

2-[(4-{6-[(1S,3S,4R,6S)-6-(Cyclopropylmethyl)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl) benzamide (Example 3), or a hydrochloride, L(+)-tartrate or succinate thereof.

(Item 55)

2-[(4-{7-[(1S,3S,4R,6R)-6-(Cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide (Example 4), or a hydrochloride, L(+)-tartrate or succinate thereof.

(Item 56)

2-[(4-{6-[(1S,3S,4R,6R)-6-(Cyclopropylmethyl)-2-azabicyclo[2.2.2]octane-3-carbonyl]-2,6-diazaspiro[3.3]heptan-2-yl}pyrimidin-5-yl)oxy]-5-fluoro-N,N-di(propan-2-yl)benzamide (Example 5), or a hydrochloride, L(+)-tartrate or succinate thereof.

(Item 57)

5-Fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (Example 6), or a hydrochloride, L(+)-tartrate or succinate thereof.

(Item 58)

5-Fluoro-2-[(4-{6-[(1S,3S,4R)-5-methylidene-2-azabicyclo[2.2.2]octane-3-carbonyl]-2,6-diazaspiro[3.3]heptan-2-yl}pyrimidin-5-yl)oxy]-N,N-di(propan-2-yl)benzamide (Example 7), or a hydrochloride, L(+)-tartrate or succinate thereof.

(Item 59)

5-Fluoro-2-[(4-{7-[(1S,3S,4R)-5-methylidene-2-azabicyclo[2.2.1]heptane-3-carbonyl]-2,7-diazaspiro[3.5]nonan-2-yl}pyrimidin-5-yl)oxy]-N,N-di(propan-2-yl)benzamide (Example 18), or a hydrochloride, L(+)-tartrate or succinate thereof.

(Item 60)

5-Fluoro-2-[(4-{7-[(1S,3S,4R)-5-($^2$H$_2$)methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (Example 20), or a hydrochloride, L(+)-tartrate or succinate thereof.

(Item 61)

A medicament comprising the compound of any one of Items 1 to 60 or a pharmaceutically acceptable salt thereof as an active ingredient.

(Item 62)

An antitumor medicament comprising the compound of any one of Items 1 to 60 or a pharmaceutically acceptable salt thereof as an active ingredient.

(Item 63)

The antitumor medicament of Items 62, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer.
(Item 64)
The antitumor medicament of Item 62 or 63, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic myeloid leukemia, malignant lymphoma (including B-cell lymphoma), myeloma (including multiple myeloma), brain tumor, prostate cancer, breast cancer, neuroblastoma, Ewing's sarcoma, or liver cancer.
(Item 65)
The antitumor medicament of any one of Items 62 to 64, wherein the tumor is MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, multiple myeloma, neuroblastoma, or prostate cancer.
(Item 66)
The antitumor medicament of any one of Items 62 to 65, wherein the tumor is MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, or multiple myeloma.
(Item 67)
The antitumor medicament of any one of Items 62 to 66, wherein the tumor is MLL acute leukemia, or NPM mutated acute leukemia.
(Item 68)
The antitumor medicament of any one of Items 62 to 67, wherein the tumor is accompanied by high expression of HOXa gene cluster, or MEIS gene cluster.
(Item 69)
The antitumor medicament of any one of Items 62 to 68, wherein the tumor is accompanied by p53 gain-of-function mutation.
(Item 70)
A method for treating a tumor comprising administrating the compound of any one of Items 1 to 60 or a pharmaceutically acceptable salt thereof to a patient in need thereof.
[Item 71]
The method of Item 70, wherein the tumor is involved in Menin-MLL.
(Item 72)
Use of the compound of any one of Items 1 to 60 or a pharmaceutically acceptable salt thereof in the manufacture of an antitumor medicament.
(Item 73)
The compound of any one of Items 1 to 60 or a pharmaceutically acceptable salt thereof for use in the treatment of a tumor.
(Item 74)
A pharmaceutical composition comprising the compound of any one of Items 1 to 60 or a pharmaceutically acceptable salt thereof in combination with at least one different agent or a pharmaceutically acceptable salt thereof, wherein the different agent is at least one agent selected from the group consisting of an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.
(Item 75)
The compound of any one of Items 1 to 60 or a pharmaceutically acceptable salt thereof for treating a tumor, which is used in combination with at least one different agent or a pharmaceutically acceptable salt thereof, wherein the different agent is at least one agent selected from an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

Effect of the Invention

The present invention provides an inhibitor of the binding between menin and MLL fusion protein, comprising an optically-active azabicyclo ring derivative or a pharmaceutically acceptable salt thereof. The compound of the present invention is useful as a medicament for diseases involved in the binding between menin and MLL, and is applicable to a patient suffering from, specifically, MLL acute leukemia, NPM mutated acute leukemia, prostate cancer, breast cancer, Ewing's sarcoma, liver cancer, p53 gain-of-function mutated cancer, and the like.

DESCRIPTION OF EMBODIMENTS

Figure 1:
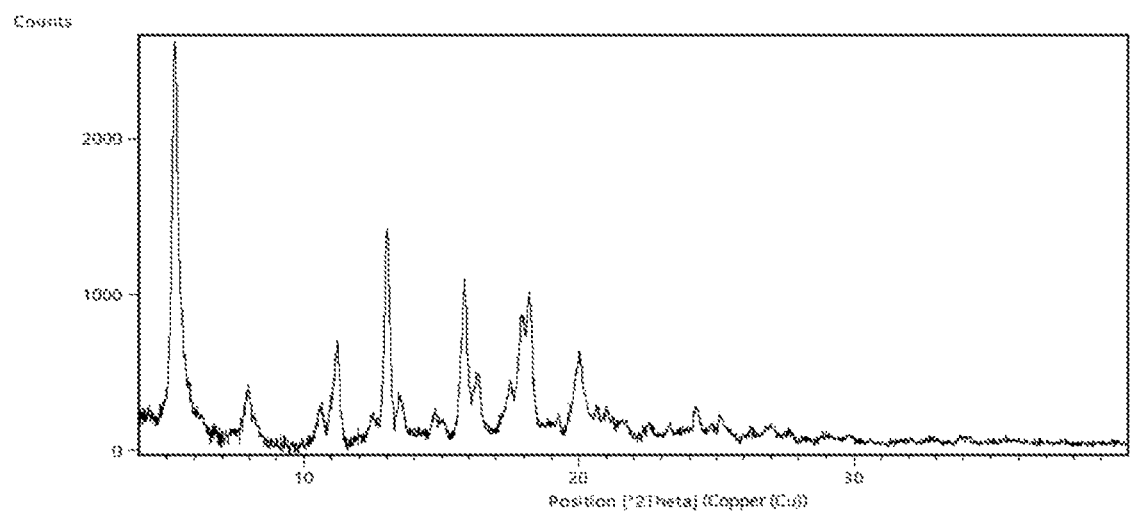
FIG. 1 shows a powder X-ray diffraction pattern of crystal form I of the compound of Example 21. The horizontal axis shows a diffraction angle 2θ (°) and the vertical axis shows counts (the same as in FIG. 2 to FIG. 5).

Hereinafter, terms used herein are explained as follows.
The "halogen atom" includes, for example, fluorine atom, chlorine atom, bromine atom, iodine atom, and the like. It is preferably fluorine atom.
The "$C_{1-6}$ alkyl" means alkyl having 1 to 6 carbon atoms, and "$C_6$ alkyl" means alkyl having 6 carbon atoms. The same is applied to the case of the other carbon numbers.
The "$C_{1-6}$ alkyl" means straight or branched chain saturated hydrocarbon group having 1 to 6 carbon atoms. The $C_{1-6}$ alkyl includes preferably "$C_{1-4}$ alkyl", more preferably "$C_{1-3}$ alkyl". The "$C_{1-3}$ alkyl" includes, for example, methyl, ethyl, propyl, 1-methylethyl, and the like. The "$C_{1-4}$ alkyl" includes, for example, butyl, 1,1-dimethylethyl, 1-methylpropyl, 2-methylpropyl, and the like, besides the examples listed in the said "$C_{1-3}$ alkyl". The "$C_{1-6}$ alkyl" includes, for example, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like, besides the examples listed in the said "$C_{1-4}$ alkyl"

The "$C_{2-6}$ alkenyl" means straight or branched chain unsaturated hydrocarbon group having 2 to 6 carbon atoms and 1 to 3 double bonds. The "$C_{2-6}$ alkenyl" includes preferably "$C_{2-4}$ alkenyl". The "$C_{2-4}$ alkenyl" includes, for example, vinyl, propenyl, methylpropenyl, butenyl, and the like. The "$C_{2-6}$ alkenyl" includes, for example, pentenyl, hexenyl, and the like, besides the examples listed in the said "$C_{2-4}$ alkenyl".

The "$C_{2-6}$ alkynyl" means straight or branched chain unsaturated hydrocarbon group having 2 to 6 carbon atoms and a triple bond. The "$C_{2-6}$ alkynyl" includes preferably "$C_{2-4}$ alkynyl". The "$C_{2-4}$ alkynyl" includes, for example, propynyl, methylpropynyl, butynyl, and the like. The "$C_{2-6}$ alkynyl" includes, for example, methylbutynyl, pentynyl, hexynyl, and the like, besides the examples listed in the said "$C_{2-4}$ alkynyl".

The "$C_{1-5}$ alkoxy" means "$C_{1-6}$ alkyloxy", and the part "$C_{1-6}$ alkyl" is as defined in the said "$C_{1-6}$ alkyl". The "$C_{1-6}$ alkoxy" includes preferably "$C_{1-4}$ alkoxy", more preferably "$C_{1-3}$ alkoxy". The "$C_{1-3}$ alkoxy" includes, for example, methoxy, ethoxy, propoxy, 1-methylethoxy, and the like. The "$C_{1-4}$ alkoxy" includes, for example, butoxy, 1,1-dimethylethoxy, 1-methylpropoxy, 2-methylpropoxy, and the like, besides the examples listed in the said "$C_{1-3}$ alkyl". The "$C_{1-6}$ alkoxy" includes, for example, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like, besides the examples listed in the said "$C_{1-4}$ alkyl".

The "$C_{1-6}$ alkylene" means divalent straight or branched chain saturated hydrocarbon group having 1 to 6 carbon atoms. The "$C_{1-6}$ alkylene" includes preferably "$C_{1-4}$ alkylene", more preferably "$C_{1-3}$ alkylene". The "$C_{1-3}$ alkylene" includes, for example, methylene, ethylene, propylene, trimethylene, and the like. The "$C_{1-4}$ alkylene" includes, for example, butylene, 1,1-dimethylethylene, 1,2-dimethylethylene, 1-methyltrimethylene, 2-methyltrimethylene, and the like, besides the examples listed in the said "$C_{1-3}$ alkylene". The "$C_{1-6}$ alkylene" includes, for example, pentylene, 1,1-dimethyltrimethylene, 1,2-dimethyltrimethylene, 1-methylbutylene, 2-methylbutylene, 1-methylpentylene, 2-methylpentylene, 3-methylpentylene, hexylene, and the like, besides the examples listed in the said "$C_{1-4}$ alkylene".

The "$C_{2-6}$ alkenylene" means divalent straight or branched chain unsaturated hydrocarbon group having 2 to 6 carbon atoms and 1 to 3 double bonds. The "$C_{2-6}$ alkenylene" includes preferably "$C_{2-4}$ alkenylene". The "$C_{2-4}$ alkenylene" includes, for example, vinylene, propenylene, methylpropenylene, butenylene, and the like. The "$C_{2-6}$ alkenylene" includes, for example, pentenylene, hexenylene, and the like, besides the examples listed in the said "$C_{2-4}$ alkenyl".

The "$C_{2-6}$ alkynylene" means divalent straight or branched chain unsaturated hydrocarbon group having 2 to 6 carbon atoms and 1 to 3 triple bonds. The "$C_{2-6}$ alkynylene" includes preferably "$C_{2-4}$ alkynylene". The "$C_{2-4}$ alkynylene" includes, for example, ethynylene, propynylene, butynylene, and the like. The "$C_{2-6}$ alkynylene" includes, for example, methylbutynylene, pentynylene, hexynylene, and the like, besides the examples listed in the said "$C_{2-4}$ alkynylene".

The "$C_{3-10}$ cycloalkyl" means cyclic saturated hydrocarbon group having 3 to 10 carbon atoms, which may have a partially-unsaturated bond or a bridged structure. The "$C_{3-10}$ cycloalkyl" includes preferably "$C_{3-7}$ cycloalkyl". The "$C_{3-7}$ cycloalkyl" includes, for example, cyclopropyl, cyclobutyl, cyclopentyl, cyclohexyl, cycloheptyl, and the like. The "$C_{3-10}$ cycloalkyl" includes, for example, cyclooctyl, cyclononyl, cyclodecyl, adamantyl, and the like, besides the examples listed in the said "$C_{3-7}$ cycloalkyl".

The "$C_{3-10}$ cycloalkyl" also encompasses bicyclic compounds, i.e., $C_{3-10}$ cycloalkyl fused with an aromatic hydrocarbon ring. The fused ring compounds includes, for example, the following structures:

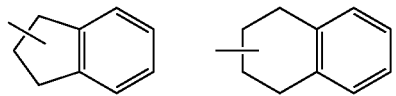

The "$C_{3-10}$ cycloalkylene" means divalent cyclic saturated hydrocarbon group having 3 to 10 carbon atoms, which may have a partially-unsaturated bond or a bridged structure. The "$C_{3-10}$ cycloalkylene" includes preferably "$C_{3-7}$-cycloalkylene". The "$C_{3-7}$ cycloalkylene" includes, for example, cyclopropylene, cyclobutylene, cyclopentylene, cyclohexylene, cycloheptylene, and the like. The "$C_{3-10}$ cycloalkylene" includes, for example, cyclooctylene, cyclononylene, cyclodecylene, adamantylene, and the like, besides the examples listed in the said "$C_{3-7}$ cycloalkylene".

The "3- to 8-membered saturated carbocycle" means cyclic saturated hydrocarbon group having 3 to 8 carbon atoms. The "3- to 8-membered saturated carbocycle" includes preferably "4- to 6-membered saturated carbocycle". The "4- to 6-membered saturated carbocycle" includes, for example, cyclobutane ring, cyclopentane ring, cyclohexane ring, and the like. The "3- to 8-membered saturated carbocycle" includes, for example, cyclopropane ring, cycloheptane ring, cyclooctane ring, and the like, besides the examples listed in the said "4- to 6-membered saturated carbocycle".

The "3- to 10-membered saturated heterocyclyl" means monovalent or divalent saturated heterocycle consisting of 1 to 2 atoms selected independently from the group consisting of nitrogen atom, oxygen atom and sulfur atom, and 2 to 9 carbon atoms, which may have a partially-unsaturated bond and a bridged structure. The atoms of which the ring consists may include oxidized atoms such as —C(O)—, —S(O)—, and —SO$_2$—. The "3- to 10-membered saturated heterocyclyl" is preferably "4- to 7-membered monocyclic saturated heterocyclyl", more preferably "5- or 6-membered monocyclic saturated heterocyclyl". The "5- or 6-membered monocyclic saturated heterocyclyl" includes, for example, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyl, tetrahydropyranyl, tetrahydrofurylene, pyrrolidinylene, imidazolidinylene, piperidinylene, morpholinylene, thiomorpholinylene, dioxothiomorpholinylene, hexamethyleneiminylene, oxazolidinylene, thiazolidinylene, oxoimidazolidinylene, dioxoimidazolidinylene, oxooxazolidinylene, dioxooxazolidinylene, dioxothiazolidinylene, tetrahydrofuranylene, tetrahydropyranylene, and the like. The "4- to 7-membered monocyclic saturated heterocyclyl" includes, for example, oxetanyl, azetidinyl, oxetanylene, azetidinylene, and the like, besides the examples listed in the said "5- or 6-membered monocyclic saturated heterocyclyl". The "3- to 10-membered saturated heterocyclyl" includes, for example, oxiranyl, aziridinyl, oxiranylene, aziridinylene, and the like, besides the examples listed in the said "4- to 7-membered monocyclic saturated heterocyclyl".

The "3- to 10-membered saturated heterocyclyl" also encompasses bicyclic compounds, i.e., "3- to 10-membered saturated heterocyclyl" fused with a 6-membered aromatic hydrocarbon ring or a 6-membered aromatic heterocycle. The 6-membered aromatic hydrocarbon ring in the fused ring includes benzene ring and the like. The 6-membered aromatic heterocycle in the fused ring includes pyridine, pyrimidine, pyridazine, and the like. The bicyclic "3- to 10-membered saturated heterocyclyl" includes dihydroindolyl, dihydroisoindolyl, dihydropurinyl, dihydrothiazolopyrimidinyl, dihydrobenzodioxanyl, isoindolyl, indazolyl, tetrahydroquinolinyl, tetrahydroisoquinolinyl, tetrahydronaphthyridinyl, dihydroindolylene, dihydroisoindolylene, dihydropurinylene, dihydrothiazolopyrimidinylene, dihydrobenzodioxanylene, isoindolylene, indazolylene, tetrahydroquinolinylene, tetrahydroisoquinolinylene, tetrahydronaphthyridinylene, and the like.

The "3- to 8-membered nitrogen-containing saturated heterocycle" means a saturated heterocycle which consists of a nitrogen atom and 2 to 7 carbon atoms. The "3- to 8-membered nitrogen-containing saturated heterocycle" includes preferably "4- to 6-membered nitrogen-containing saturated heterocycle". The "4- to 6-membered nitrogen-containing saturated heterocycle" includes, for example, azetidine ring, pyrrolidine ring, piperidine ring, and the like. The "3- to 8-membered nitrogen-containing saturated heterocycle" includes, for example, aziridine ring, azepane ring, azocane ring, and the like, besides the examples listed in the said "4- to 6-membered nitrogen-containing saturated heterocycle".

The "$C_{6-10}$ aryl" means aromatic hydrocarbon ring having 6 to 10 carbon atoms. The "$C_{6-10}$ aryl" includes, for example, phenyl, 1-naphthyl, 2-naphthyl, and the like. It includes preferably phenyl.

The "$C_{6-10}$ aryl" also encompasses bicyclic compounds, i.e., $C_{6-10}$ aryl fused with $C_{4-6}$ cycloalkyl or 5- or 6-membered saturated heterocycle. The bicyclic "$C_{6-10}$ aryl" includes, for example, the following groups:

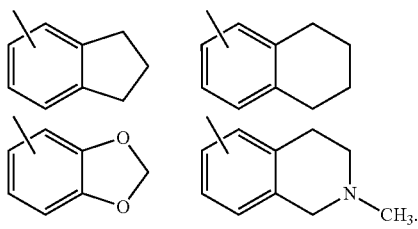

The "$C_{6-10}$ arylene" means divalent aromatic hydrocarbon group having 6 to 10 carbon atoms. The "$C_{6-10}$ arylene" includes, for example, phenylene, 1-naphthylene, 2-naphthylene, and the like. It includes preferably phenylene.

The "aromatic hydrocarbon ring" means a cyclic part of the said "$C_{6-10}$ aryl" and the said "$C_{6-10}$ arylene".

The "5- to 12-membered heteroaryl" means monocyclic 5- to 7-membered aromatic heterocyclic group or bicyclic 8- to 12-membered aromatic heterocyclic group having 1 to 4 atoms selected independently from the group consisting of nitrogen atom, oxygen atom and sulfur atom. It is preferably "5- to 7-membered monocyclic heteroaryl". It is more preferably pyridyl, pyrimidinyl, quinolyl, or isoquinolyl. It is even more preferably pyridyl. The "5- to 7-membered monocyclic heteroaryl" includes, for example, pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, triazinyl, triazolyl, oxadiazolyl, triazolyl, tetrazolyl, and the like. The "5- to 12-membered heteroaryl" includes indolyl, indazolyl, chromenyl, quinolyl, isoquinolyl, benzofuranyl, benzothienyl, benzooxazolyl, benzothiazolyl, benzoisoxazolyl, benzoisothiazolyl, benzotriazolyl, benzoimidazolyl, and the like, besides the examples listed in the said "5- to 7-membered monocyclic heteroaryl".

The "5- to 12-membered heteroarylene" means divalent monocyclic 5- to 7-membered aromatic heterocyclic group or divalent bicyclic 8- to 12-membered aromatic heterocyclic group having 1 to 4 atoms selected independently from the group consisting of nitrogen atom, oxygen atom and sulfur atom. It is preferably "5- to 7-membered monocyclic heteroarylene". It is more preferably pyridylene, pyrimidylene, quinolylene, or isoquinolylene. It is even more preferably pyridylene. The "5- to 7-membered monocyclic heteroarylene" includes, for example, pyridylene, pyridazinylene, isothiazolylene, pyrrolylene, furylene, thienylene, thiazolylene, imidazolylene, pyrimidinylene, thiadiazolylene, pyrazolylene, oxazolylene, isooxazolylene, pyrazinilene, triazinylene, triazolylene, oxadiazolylene, triazolylene, tetrazolylene, and the like. The "5- to 12-membered heteroarylene" includes indolylene, indazolylene, chromenylene, quinolylene, isoquinolylene, benzofuranylene, benzothienylene, benzooxazolylene, benzothiazolylene, benzoisooxazolylene, benzoisothiazolylene, benzotriazolylene, benzoimidazolylene, and the like, besides the examples listed in the said "5- to 7-membered monocyclic heteroarylene".

The "aromatic heterocyclic group" means a cyclic part of the said "5- to 12-membered heteroaryl" and the said "5- to 12-membered heteroarylene".

In the present specification, a bond across a ring group as showed in the following formula (W) means that the bond is attached to a substitutable position of the "group". For example, in the case of the following formula (W):

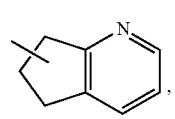

(W)

, it represents the following formula (W-1), (W-2), or (W-3):

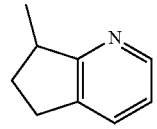

(W-1)

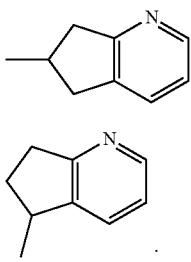

(W-2)

(W-3)

In the present specification, the stereochemistry of substituents in the compound of formula (I) or the example compounds can be illustrated, for example, as follows:

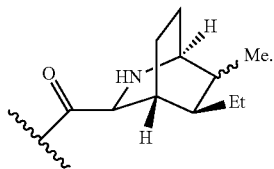 [SMILES: *C(=O)C1N[C@H]2CC[C@@H]1[C@H](CC)C2C]

In the above structure, the bonds shown as wedged line represent substituents in front of the page; the bond shown as dashed line represents a substituent in back of the page; and the bond shown as wavy line represents that the substituent exists in front and back of the page in an certain ratio, and when a bond which extends from the ring outside is shown as linear line, it represents that the bond exists either in front or back of the page.

The "cancer" and "tumor" are used interchangeably, and the both mean malignant neoplasm, which encompasses cancer, sarcoma, and hematologic malignancy. The "cancer" and "tumor" include, for example, acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, a myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, skin cancer, and the like. The above tumors may be accompanied by increased expression or mutation of specific genes. The tumors accompanied by increased expression of genes include, for example, tumors accompanied by high expression of HOXa gene cluster, tumors accompanied by high expression of MEIS gene cluster, and the like. The tumors accompanied by mutation of genes include tumors accompanied by p53 gain-of-function mutation and the like.

In the present compound of formula (1), preferred p, X, Y, Z, M, Q, a, b, c, d, U, $R^1$, $R^2$, $R^3$, $R^4$, $R^{5A}$, $R^{5B}$, $R^{6A}$, $R^{6B}$, $R^{6C}$, $R^{6D}$, $R^7$, $R^8$, $R^9$, $R^{10}$, $R^{11}$, $R^{12A}$, $R^{12B}$, $R^{13A}$, $R^{13B}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35A}$, $R^{35B}$, $R^{36A}$, $R^{36B}$, $R^{37A}$ and $R^{37B}$ are as follows, but the technical scope of the present invention is not limited to the scope of compounds listed below.

In an embodiment, p includes 1. In another embodiment, p includes 2.

X is preferably —C(O)—.

Y is preferably —O—.

Z includes preferably (Z-1), (Z-2), (Z-3), (Z-4), (Z-5), (Z-6), (Z-7), (Z-8), and (Z-9). It is more preferably (Z-3).

M includes preferably $C_{1-3}$ alkylene optionally substituted with 1 to 3 the same or different substituents selected from the group consisting of fluorine atom, $C_{2-4}$ alkynyl, $C_{1-3}$ alkoxy, —$NR^{36A}R^{37A}$, and cyano. It includes more preferably $C_{1-3}$ alkylene. It includes even more preferably methylene.

Q includes preferably $C_{3-6}$ cycloalkyl optionally-substituted with 1 to 3 the same or different substituents selected from the group consisting of fluorine atom, $C_{1-3}$ alkyl, —$NR^{36A}SO_2R^{35A}$, —$SO_2NR^{36A}R^{37A}$, and cyano; 3- to 6-membered saturated heterocyclyl optionally-substituted with 1 to 3 the same or different substituents selected from the group consisting of fluorine atom, $C_{1-3}$ alkyl, —$NR^{36A}SO_2R^{35A}$, —$SO_2NR^{36A}R^{37A}$, and cyano; phenyl optionally-substituted with 1 to 3 the same or different substituents selected from the group consisting of fluorine atom, $C_{1-3}$ alkyl, —$NR^{36A}SO_2R^{31}$, —$SO_2NR^{36A}R^{37A}$, and cyano; and 5- to 6-membered heteroaryl optionally-substituted with 1 to 3 the same or different substituents selected from the group consisting of fluorine atom, $C_{1-3}$ alkyl, —$NR^{36A}SO_2R^{35A}$, —$SO_2NR^{36A}R^{37A}$, and cyano. It includes more preferably $C_{3-6}$ cycloalkyl optionally-substituted with 1 to 3 the same or different substituents selected from the group consisting of fluorine atom, $C_{1-3}$ alkyl, —$NR^{36}SO_2R^{35A}$, —$SO_2NR^{36A}R^{37A}$, and cyano. It includes even more preferably $C_{3-6}$ cycloalkyl optionally-substituted with 1 to 3 the same or different substituents selected from the group consisting of fluorine atom and $C_{1-3}$ alkyl. $C_{3-6}$ cycloalkyl is especially preferable.

The symbols a and c include preferably 1.

In an embodiment, both of b and d include 1. In another embodiment, both of b and d include 2.

U is preferably nitrogen atom.

$R^1$ includes preferably hydrogen atom or -M-Q.

$R^2$ includes preferably hydrogen atom or -M-Q.

$R^3$ includes preferably hydrogen atom or fluorine atom.

$R^4$ includes preferably hydrogen atom or fluorine atom.

In another embodiment, $R^1$ and $R^2$ are combined together to form =$CR^{12A}R^{13A}$. It is more preferably =$CH_2$.

In another embodiment, $R^3$ and $R^4$ are combined together to form =$CR^{12A}R^{13A}$. It is more preferably —$CH_2$.

In another embodiment of $R^1$, $R^2$, $R^3$, and R, $R^1$ is hydrogen atom, $R^2$ is -M-Q, $R^3$ is hydrogen atom, and $R^4$ is hydrogen atom or fluorine atom.

In another embodiment of $R^1$, $R^2$, $R^3$, and $R^4$, $R^1$ is -M-Q, $R^2$ is hydrogen atom, $R^3$ is hydrogen atom or fluorine atom, and $R^4$ is hydrogen atom.

In another embodiment of $R^1$, $R^2$, $R^3$, and $R^4$, $R^1$ and $R^2$ are both hydrogen atom, and $R^3$ and $R^4$ are combined together to form =$CH_2$.

In another embodiment of $R^1$, $R^2$, $R^3$, and $R^4$, $R^3$ and $R^4$ are both hydrogen atom, and $R^1$ and $R^2$ are combined together to form =$CH_2$.

In another embodiment of $R^1$, $R^2$, $R^3$, and $R^4$, $R^1$ and $R^2$ are both hydrogen atom, $R^3$ is hydrogen atom, and $R^4$ is fluorine atom.

In another embodiment of $R^1$, $R^2$, $R^3$, and $R^4$, $R^1$ and $R^2$ are both hydrogen atom, $R^3$ is fluorine atom, and $R^4$ is hydrogen atom.

$R^{5A}$ and $R^{5B}$ are preferably hydrogen atom.

$R^{6A}$, $R^{6B}$, and $R^{6D}$ are preferably hydrogen atom.

$R^{6C}$ is preferably fluorine atom.

$R^7$ includes preferably hydrogen atom, $C_{1-6}$ alkyl, or $C_{2-6}$ alkenyl, wherein the alkyl or the alkenyl may be substituted with one phenyl.

$R^8$, $R^{14}$, $R^{18}$, $R^{25}$, $R^{31}$, $R^{35A}$, and $R^{35B}$ are preferably $C_{1-3}$ alkyl.

$R^9$, $R^{10}$, $R^{11}$, $R^{15}$, $R^{16}$, $R^{17}$, $R^{19}$, $R^{20}$, $R^{21}$, $R^{23}$, $R^{24}$, $R^{26}$, $R^{27}$, $R^{28}$, $R^{29}$, $R^{30}$, $R^{32}$, $R^{33}$, $R^{34}$, $R^{36A}$, $R^{36B}$, $R^{37A}$, and $R^{37B}$ include preferably hydrogen atom or $C_{1-3}$ alkyl.

$R^{12A}$ and $R^{13A}$ include preferably $C_{3-6}$ cycloalkyl optionally-substituted with 1 to 3 the same or different substituents selected from the group consisting of hydrogen atom or fluorine atom, $C_{1-3}$ alkyl, $-NR^{36A}SO_2R^{35A}$, $-SO_2NR^{36A}R^{37A}$, and cyano. It is more preferably hydrogen atom.

$R^{12B}$ and $R^{13B}$ include preferably $C_{1-3}$ alkyl.

$R^{22}$ is preferably $-CF_3$ or cyano.

In an embodiment, the present compound of formula (1) includes the following (A).

(A)

A Compound or pharmaceutically acceptable salt thereof, wherein formula (1) is formula (1a);

p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=O$ or $=CR^{12A}R^{13A}$;

M is, each independently if there are plural, $C_{1-3}$ alkylene;

Q is, each independently if there are plural, $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{12A}$ and $R^{3A}$ are each independently hydrogen atom, or $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are each attached to form 3- to 6-membered nitrogen-containing saturated heterocycle;

a and c are 1; and both b and d are either 1 or 2.

An embodiment of the present compound of formula (1) includes the following (B):

(B)

A compound or pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=O$ or $=CR^{12A}R^{13A}$;

M is, each independently if there are plural, $C_{1-3}$ alkylene;

Q is, each independently if there are plural, $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{12A}$ and $R^{13A}$ are each independently hydrogen atom, or $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are each attached to form 3- to 6-membered nitrogen-containing saturated heterocycle;

X is $-C(O)-$;

a and c are 1;

both b and d are either 1 or 2;

$R^{5A}$, $R^{5B}$, $R^{6A}$, $R^{6B}$, and $R^{6D}$ are hydrogen atom:

$R^{6C}$ is fluorine atom;

U is nitrogen atom;

Y is $-O-$; and

Z is (Z-1), (Z-2), (Z-3), (Z-4), (Z-5), (Z-6), (Z-7), (Z-8), or (Z-9).

An embodiment of the present compound of formula (1) includes the following (C):

(C)

A compound or pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=O$ or $=CR^{12A}R^{13A}$;

M is, each independently if there are plural, $C_{1-3}$ alkylene;

Q is, each independently if there are plural, $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{12A}$ and $R^{13A}$ are each independently hydrogen atom, or $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

X is $-C(O)-$;

a and c are 1;

both b and d are either 1 or 2;

$R^{5A}$, $R^{5B}$, $R^{6A}$, $R^{6B}$, and $R^{6D}$ are hydrogen atom;

$R^{6C}$ is fluorine atom;

U is $CR^{22}$;

$R^{22}$ is $-CF_3$ or cyano;

Y is $-O-$; and

Z is (Z-3).

An embodiment of the present compound of formula (1) includes the following (D):

(D)

A compound or pharmaceutically acceptable salt thereof, wherein formula (1) is formula (1a);

p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene;

Q is, each independently if there are plural, $C_{3-6}$ cycloalkyl;

a and c are 1; and both b and d is either 1 or 2.

An embodiment of the present compound of formula (1) includes the following (E):

(E)

A compound or pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene;

Q is, each independently if there are plural, $C_{3-6}$ cycloalkyl;

X is —C(O)—;

a and c are 1;

both b and d are either 1 or 2;

$R^{5A}$, $R^{5B}$, $R^{6A}$, $R^{6B}$, and $R^{6D}$ are hydrogen atom;

$R^{6C}$ is fluorine atom;

U is nitrogen atom;

Y is —O—; and

Z is (Z-1), (Z-2), (Z-3), (Z-4), (Z-5), (Z-6), (Z-7), (Z-8), or (Z-9).

An embodiment of the present compound of formula (1) includes the following (F):

(F)

A compound or pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene;

Q is, each independently, if there are plural, $C_{3-6}$ cycloalkyl;

X is —C(O)—;

a and c are 1;

both b and d are either 1 or 2;

$R^{5A}$, $R^{5B}$, $R^{6A}$, $R^{6B}$, and $R^{6D}$ are hydrogen atom;

$R^{6C}$ is fluorine atom;

U is $CR^{22}$;

$R^{22}$ is —$CF_3$ or cyano;

Y is —O—; and

Z is (Z-3).

An embodiment of the present compound of formula (1) includes the following (G):

(G)

A compound or pharmaceutically acceptable salt thereof, wherein formula (1) is formula (1a);

p is 1 or 2;

$R^1$ and $R^2$ are hydrogen atom;

$R^3$ and $R^4$ are each independently hydrogen atom or fluorine atom;

a and c are 1; and both b and d are either 1 or 2;

provided that both $R^3$ and $R^4$ are not hydrogen atom.

An embodiment of the present compound of formula (1) includes the following (H):

(H)

A compound or pharmaceutically acceptable salt thereof, wherein p is 1 or 2;

$R^1$ and $R^2$ are hydrogen atom;

$R^3$ and $R^4$ are each independently hydrogen atom or fluorine atom;

X is —C(O)—;

a and c are 1;

both b and d are either 1 or 2;

$R^{5A}$, $R^{5B}$, $R^{6A}$, $R^{6B}$, and $R^{6D}$ are hydrogen atom;

$R^{6C}$ is fluorine atom;

U is nitrogen atom;

Y is —O—; and

Z is (Z-1), (Z-2), (Z-3), (Z-4), (Z-5), (Z-6), (Z-7), (Z-8), or (Z-9);

provided that both $R^3$ and $R^4$ are not hydrogen atom.

An embodiment of the present compound of formula (1) includes the following (I):

(I)

A compound or pharmaceutically acceptable salt thereof, wherein p is 1 or 2;

$R^1$ and $R^2$ are hydrogen atom;

$R^3$ and $R^4$ are each independently hydrogen atom or fluorine atom;

X is —C(O)—;

a and c are 1;

both b and d are either 1 or 2;

$R^{5A}$, $R^{5B}$, $R^{6A}$, $R^{6B}$, and $R^{6D}$ are hydrogen atom;

$R^{6C}$ is fluorine atom;

U is $CR^{22}$;

$R^{22}$ is —$CF_3$ or cyano;

Y is —O—; and

Z is (Z-3), provided that both $R^3$ and $R^4$ are not hydrogen atom.

An embodiment of the present compound of formula (1) includes the following (J):

(J)

A compound or pharmaceutically acceptable salt thereof, wherein formula (1) is formula (1a);

p is 1 or 2;

$R^1$ and $R^2$ are each independently hydrogen atom or -M-Q;

$R^3$ and $R^4$ are each independently hydrogen atom or fluorine atom;

M is, each independently if there are plural, methylene;

Q is, each independently if there are plural, $C_{3-6}$ cycloalkyl;

a and c are 1; and both b and d are either 1 or 2;

provided that both $R^1$ and $R^2$ are not hydrogen atom.

An embodiment of the present compound of formula (1) includes the following (K):

(K)

A compound or pharmaceutically acceptable salt thereof, wherein p is 1 or 2;

$R^1$ and $R^2$ are each independently hydrogen atom or -M-Q;

$R^3$ and $R^4$ are each independently hydrogen atom or fluorine atom;

M is, each independently if there are plural, methylene;

Q is, each independently, if there are plural, $C_{3-6}$ cycloalkyl;

X is —C(O)—;

a and c are 1;

both b and d are either 1 or 2;

$R^{5A}$, $R^{5B}$, $R^{6A}$, $R^{6B}$, and $R^{6D}$ are hydrogen atom;

$R^{6C}$ is fluorine atom;

U is nitrogen atom;

Y is —O—; and

Z is (Z-1), (Z-2), (Z-3), (Z-4), (Z-5), (Z-6), (Z-7), (Z-8), or (Z-9), provided that both $R^1$ and $R^2$ are not hydrogen atom.

An embodiment of the present compound of formula (1) includes the following (L):

(L)

A compound or pharmaceutically acceptable salt thereof, wherein p is 1 or 2;

$R^1$ and $R^2$ are each independently hydrogen atom or -M-O;

$R^3$ and $R^4$ are each independently hydrogen atom or fluorine atom;

M is, each independently if there are plural, methylene;

Q is, each independently if there are plural, $C_{3-6}$ cycloalkyl,

X is —C(O)—;

a and c are 1;

both b and c are either 1 or 2;

$R^{5A}$, $R^{5B}$, $R^{6A}$, $R^{6B}$, and $R^{6D}$ are hydrogen atom;

$R^{6C}$ is fluorine atom;

U is $CR^{22}$;

$R^{22}$ is —$CF_3$ or cyano;

Y is —O—; and

Z is (Z-3);

provided that both $R^1$ and $R^2$ are not hydrogen atom.

An embodiment of the present compound of formula (1) includes the following (M):

(M)

A compound or pharmaceutically acceptable salt thereof, wherein formula (1) is formula (1a);

p is 1 or 2;

$R^1$, $R^2$, $R^3$, and $R^4$ are each independently hydrogen atom; or $R^1$ and $R^2$ and/or $R^3$ and $R^4$ may be combined together to form =$CH_2$;

a and c are 1; and both b and d are either 1 or 2;

provided that all of $R^1$, $R^2$, $R^3$, and $R^4$ are not hydrogen atom.

An embodiment of the present compound of formula (1) includes the following (N):

(N)

A compound or pharmaceutically acceptable salt thereof, wherein p is 1 or 2;

$R^1$, $R^2$, $R^3$, and $R^4$ are each independently hydrogen atom; or $R^1$ and $R^2$ and/or $R^3$ and $R^4$ may be combined together to form =$CH_2$;

X is —C(O)—;

a and c are 1;

both b and d are either 1 or 2;

$R^{5A}$, $R^{5B}$, $R^{6A}$, $R^{6B}$, and $R^{6D}$ are hydrogen atom;

$R^{6C}$ is fluorine atom;

U is nitrogen atom;

Y is —O—; and

Z is (Z-1), (Z-2), (Z-3), (Z-4), (Z-5), (Z-6), (Z-7), (Z-8), or (Z-9);

provided that all of $R^1$, $R^2$, $R^3$, and $R^4$ are not hydrogen atom.

An embodiment of the present compound of formula (1) includes the following (O):

(O)

A compound or pharmaceutically acceptable salt thereof, wherein p is 1 or 2;

$R^1$, $R^2$, $R^3$, and $R^4$ are each independently hydrogen atom; or $R^1$ and $R^2$ and/or $R^3$ and $R^4$ may be combined together to form =$CH_2$;

X is —C(O)—;

a and c are 1;

both b and d are either 1 or 2;

$R^{5A}$, $R^{5B}$, $R^{6A}$, $R^{6B}$, and $R^{6D}$ are hydrogen atom;

$R^{6C}$ is fluorine atom;

U is $CR^{22}$;

$R^{22}$ is —$CF_3$ or cyano;

Y is —O—; and

Z is (Z-3), provided that all of $R^1$, $R^2$, $R^3$, and $R^4$ are not hydrogen atom.

Hereinafter, the processes to prepare the compound of the present invention of formula (1) are exemplified along with examples, but the processes to prepare the compound of the present invention should not be limited to the examples. Compounds used in the following process may exist as their salts unless they affect reactions.

The compound of the present invention can be prepared from known compounds as starting materials, for example, by the following methods A, B, C, D, E, F, G, H, I, J, K, L, M, N, and O, or similar methods thereto, or optionally in combination with synthetic methods well-known to a person skilled in the art.

Preparation Process A

The compound of the present invention of formula (1) can be prepared, for example, by the following process:

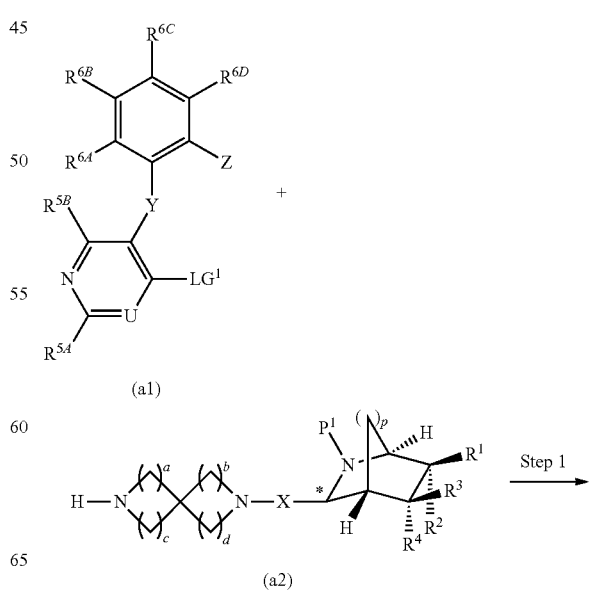

-continued

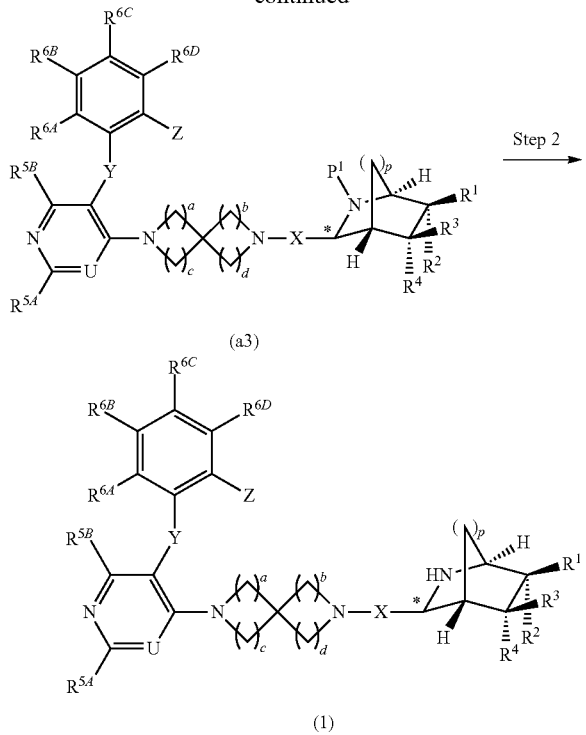

wherein a, b, c, d, p, $R^1$, $R^2$, $R^3$, $R^4$, $R^{5A}$, $R^{5B}$, $R^{6A}$, $R^{6B}$, $R^{6C}$, $R^{6D}$, U, X, Y, and Z are as defined in Item 1; $LG^1$ is a leaving group; and $P^1$ is an amino-protecting group, wherein $LG^1$ includes, for example, halogen atom, methanesulfonyloxy, p-toluenesulfonyloxy, trifluoromethanesulfonyloxy, phenoxy, trifluorophenoxy, tetrafluorophenoxy, pentafluorophenoxy, nitrophenoxy, and the like; $P^1$ includes, for example, amino-protecting groups described in T. W. Greene, and P. G. M. Wuts, "*Protective Groups in Organic Synthesis*", John Wiley & Sons, Inc., (1999), and the like; and the stereochemistry of the carbon with * is not inverted during reactions.

(Step 1)

Compound (a3) can be prepared by reacting compound (a1) obtained in the following process with compound (a2) obtained in the following procedure in the presence or absence of an appropriate base in an appropriate solvent.

Compound (a1) used herein can be obtained by the following preparation process B (as compound (a1)), by the following preparation process D (compound (D1)), or by the following preparation process E (compound (E1)). Compound (a2) used herein can be obtained by the following preparation process F (as compound (F1)), or by the following preparation process G (compound (G1)).

The base used herein includes, for example, organic bases such as triethylamine, diisopropylethylamine, tributylamine, 1.5-diazabicyclo[4.3.0]non-5-ene (DBN), 1,8-diazabicyclo[5.4.0]undec-7-ene (DBU), pyridine, 4-dimethylaminopyridine, picoline, and N-methylmorpholine (NMM), and inorganic bases such as sodium bicarbonate, potassium bicarbonate, sodium carbonate, potassium carbonate, sodium hydroxide, and potassium hydroxide. The base includes preferably triethylamine, diisopropylethylamine, potassium carbonate, sodium hydroxide, and the like.

The solvent used herein includes, for example, alcohol solvents such as methanol, ethanol, 2-propanol (isopropyl alcohol), and tert-butanol; ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate, and methyl acetate; aprotic solvents such as acetonitrile, N,N-dimethylformamide, N,N-dimethylacetamide, N-methyl-2-pyrrolidinone, 1,3-dimethyl-2-imidazolidinone, and dimethylsulfoxide; and mixtures thereof, but not specifically limited thereto unless it reacts under the reaction condition in the present processes. The solvent includes preferably 2-propanol, tetrahydrofuran, toluene, acetonitrile, N,N-dimethylformamide, and the like.

The reaction temperature is generally −80° C. to reflux temperature, preferably 25° C. to 90° C.

The reaction time is generally 30 minutes to 48 hours, preferably 6 to 12 hours.

Alternatively, compound (a1) may be coupled with compound (a2) in the presence of an appropriate metal catalyst in an appropriate solvent. The reaction condition includes, for example, Ulmann-type condition (for example, heating under reflux with a metal catalyst such as copper(II) acetate in an aprotic solvent such as DMF), Buchwald-type condition (for example, heating under reflux with alkali metal carbonate such as cesium carbonate; BINAP; a palladium catalyst such as $Pd_2(dba)_3$ and $Pd(OAc)_2$; and a ligand such as dppf and Xantphos, in an inert solvent under the reaction conditions such as toluene).

The solvent used herein includes, for example, alcohol solvents such as methanol, ethanol, 2-propanol (isopropyl alcohol), and tert-butanol; ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate and methyl acetate; aprotic solvents such as acetonitrile, N,N-dimethylformamide, N,N-dimethylacetamide, N-methyl-2-pyrrolidinone, 1,3-dimethyl-2-imidazolidinone, and dimethylsulfoxide; water; and mixtures thereof, but should not specifically limited thereto unless it reacts under the reaction condition in the present processes. The solvent includes preferably tetrahydrofuran, toluene, acetonitrile, N,N-dimethylformamide, and the like.

The reaction temperature is generally −80° C. to reflux temperature, preferably 25° C. to 90° C.

The reaction time is generally 30 minutes to 48 hours, preferably 6 to 12 hours.

(Step 2)

Compound (1) can be prepared by removing protecting group $P^1$ from compound (a3). The present step can be carried out according to a known method described, for example, in T. W. Greene, P. G. M. Wuts, "*Protective Groups in Organic Synthesis*", John Wiley & Sons, Inc., (1999), or a similar method.

Preparation process B

The compound of formula (a1) can be prepared, for example, by the following process:

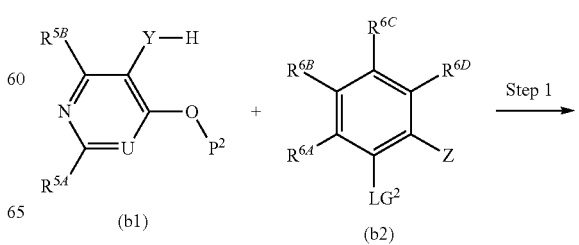

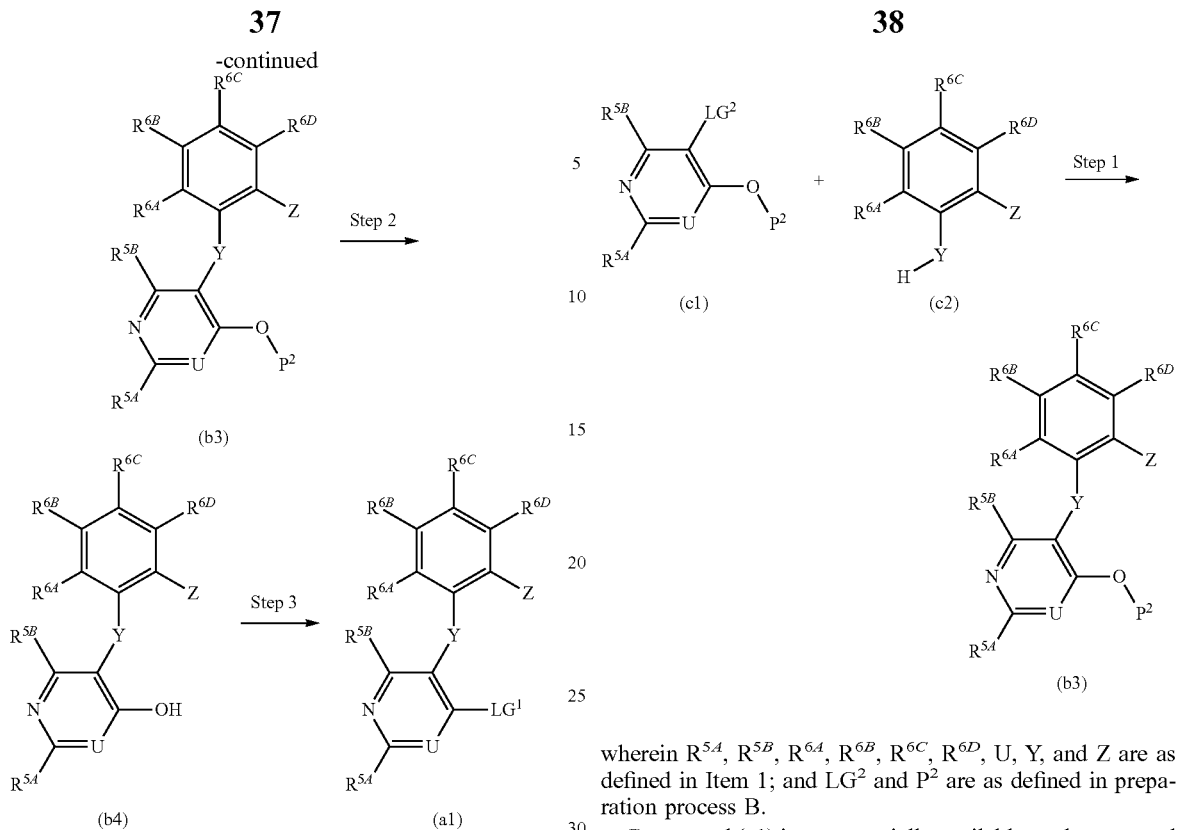

wherein $R^{5A}$, $R^{5B}$, $R^{6A}$, $R^{6B}$, $R^{6C}$, $R^{6D}$, U, Y, and Z are as defined in Item 1, $LG^1$ is as defined in preparation process A, $LG^2$ is a leaving group, and $P^2$ is a hydroxy-protecting group, wherein $LG^2$ includes, for example, halogen atom, methanesulfonyloxy, p-toluenesulfonyloxy, trifluoromethanesulfonyloxy, phenoxy, trifluorophenoxy, tetrafluorophenoxy, pentafluorophenoxy, nitrophenoxy, and the like; and $P^2$ includes, for example, hydroxy-protecting groups described in T. W. Greene, and P. G. M. Wuts, "*Protective Groups in Organic Synthesis*", John Wiley & Sons, Inc., (1999), and the like.

Compound (b1) and compound (b2) are commercially available.

(Step 1)

Compound (b3) can be prepared from compound (b1) and compound (b2) according to the process of step 1 in preparation process A or a similar method.

(Step 2)

Compound (b4) can be prepared by removing protecting group $P^2$ from compound (b3). The present step can be carried out according to a known method described, for example, in T. W. Greene, and P. G. M. Wuts, "*Protective Groups in Organic Synthesis*", John Wiley & Sons, Inc., (1999), or a similar method.

(Step 3)

Compound (a1) can be prepared from compound (b4) according to a known method described in *J. Med. Chem.*, 53(16): 6129-6152 (2010), *J. Med. Chem.*, 59(17): 7936-7949 (2016), *J. Org. Chem.*, 76(10): 4149-4153 (2011), *European Journal of Medicinal Chemistry*, 44 (10): 4179-4191 (2009), or a similar method.

Preparation Process C

The compound of formula (b3) can be prepared, for example, by the following process:

wherein $R^{5A}$, $R^{5B}$, $R^{6A}$, $R^{6B}$, $R^{6C}$, $R^{6D}$, U, Y, and Z are as defined in Item 1; and $LG^2$ and $P^2$ are as defined in preparation process B.

Compound (c1) is commercially available, and compound (c2) can be prepared according to a known method described in WO 2017/214367 or a similar method, or can be obtained as a marketed product.

(Step 1)

Compound (b3) can be prepared from compound (c1) and compound (c2) according to the method described in step 1 of preparation process A or a similar method.

Preparation Process D

In the compound of formula (a1), the compound of formula (D1) can be prepared, for example, by the following method:

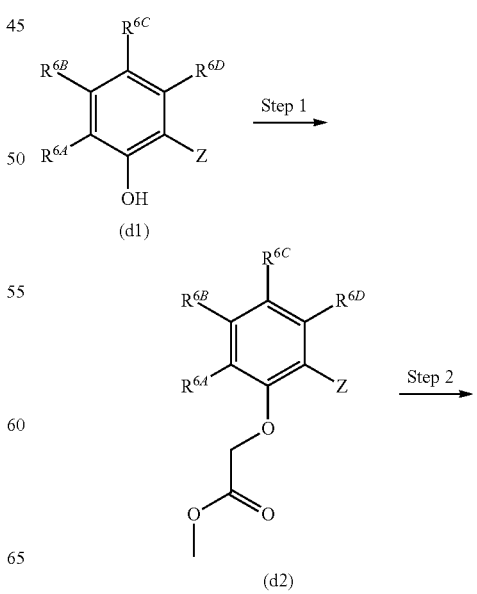

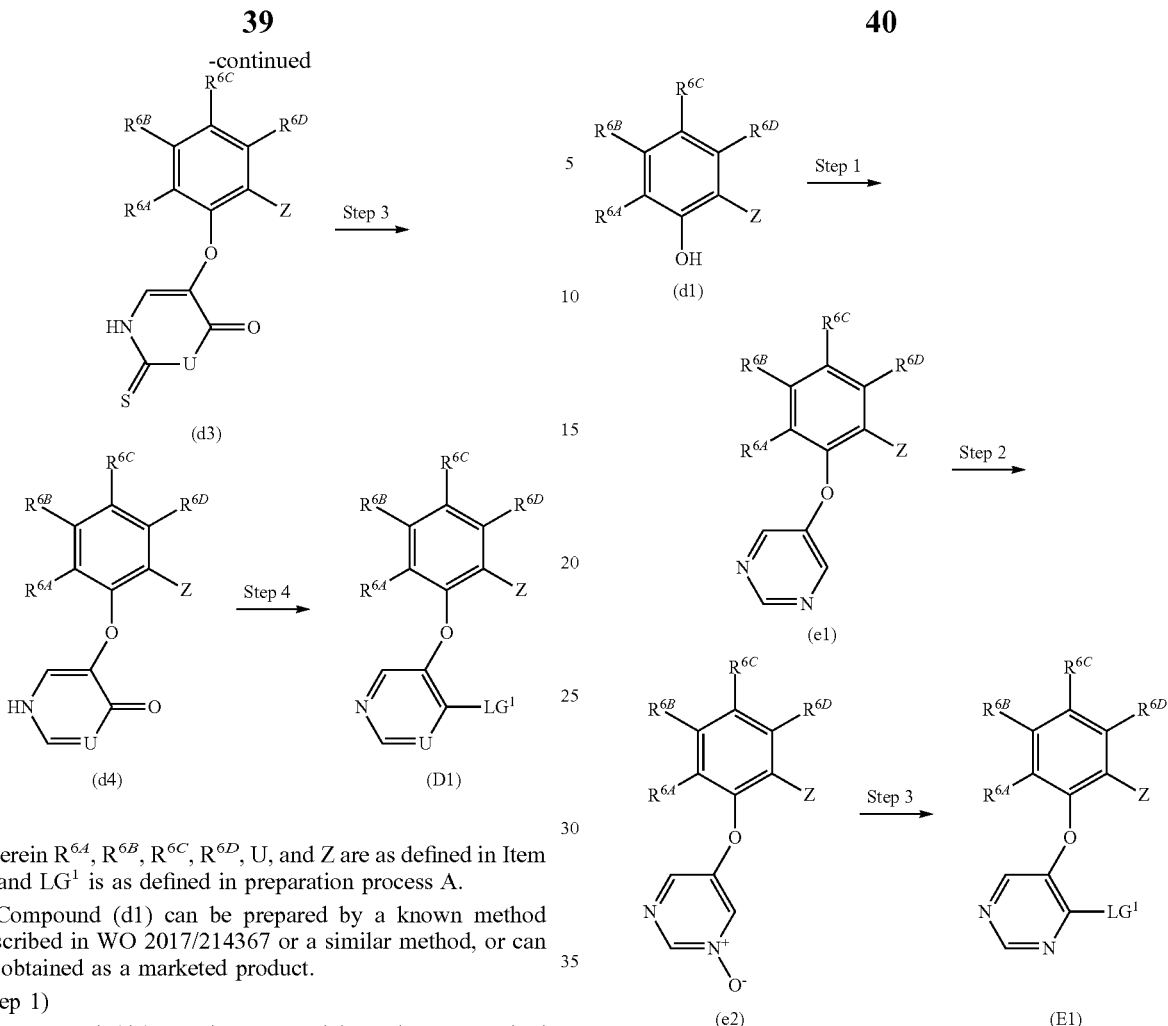

wherein $R^{6A}$, $R^{6B}$, $R^{6C}$, $R^{6D}$, U, and Z are as defined in Item 1; and $LG^1$ is as defined in preparation process A.

Compound (d1) can be prepared by a known method described in WO 2017/214367 or a similar method, or can be obtained as a marketed product.

(Step 1)

Compound (d2) can be prepared by a known method described in *Bioorganic & Medicinal Chemistry Letters*, 22 (24): 7456-7460 (2012), *Bioorganic & Medicinal Chemistry Letters*, 12 (8): 1185-1187 (2002), *Bioorganic & Medicinal Chemistry*, 23(1): 132-140 (2015), *Bioorganic & Medicinal Chemistry*, 19(1): 211-220 (2011), or a similar method.

(Step 2)

Compound (d3) can be prepared from compound (d2) by a known method described in *European Journal of Medicinal Chemistry*, 23 (1): 53-62 (1988), *Tetrahedron*, 62 (23): 5469-5473 (2006), WO 2008/092049, WO 2015/175707, or a similar method.

(Step 3)

Compound (d4) can be prepared from compound (d3) by a known method described in *J. Med. Chem.*, 23 (9): 1026-1031 (1980), WO 2003/087067, WO 2000/061562, or a similar method.

(Step 4)

Compound (D1) can be prepared from compound (d4) by a known method described in *European Journal of Medicinal Chemistry*, 44(10): 4179-4191 (2009), *J. Org. Chem.*, 76(10): 4149-4153 (2011), *J. Med. Chem.*, 53(16): 6129-6152 (2010), *J. Med. Chem.*, 59(17): 7936-7949 (2016), or a similar method.

Preparation Process E

In the compound of formula (a1), the compound of formula (E1) can be prepared, for example, by the following method:

wherein $R^{6A}$, $R^{6B}$, $R^{6C}$, $R^{6D}$, and Z are as defined in Items 1; and $LG^1$ is as defined in preparation process A.

Compound (d1) can be prepared by a known method described in WO 2017/214367 or a similar method, or can be obtained as a marketed product.

(Step 1)

Compound (e1) can be prepared from compound (d1) according to the method described in step 1 of preparation process C, or a similar method.

(Step 2)

Compound (e2) can be prepared from compound (e1) by a known method described in *J. Org. Chem.*, 82(17): 8933-8942 (2017), *Tetrahedron*, 68(29): 5845-5851 (2012), *J. Am. Chem. Soc.*, 139(16): 5998-6007 (2017), *Angewandte Chemie, International Edition*, 45(46): 7781-7786 (2006), or a similar method.

(Step 3)

Compound (E1) can be prepared from compound (e2) by a known method described in WO 2017/214367, WO 2009/137733 or a similar method.

Preparation Process F

In the compound of formula (a2), the compound of formula (F1) can be prepared, for example, by the following method:

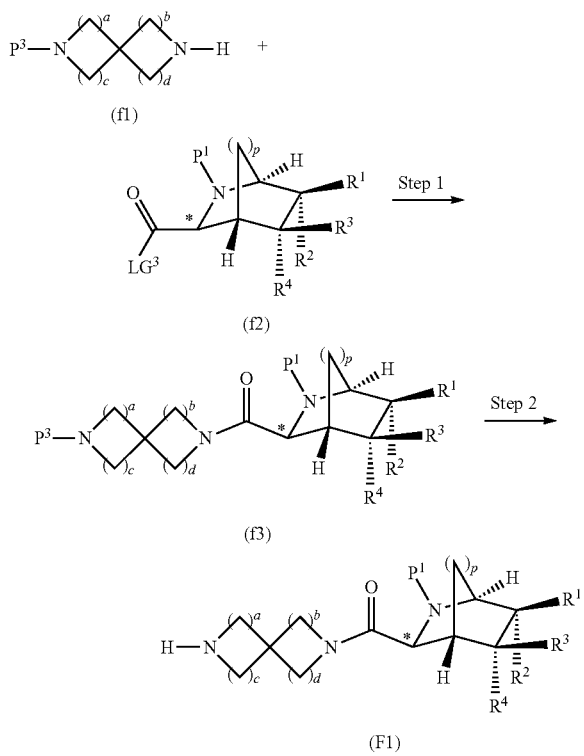

(f1)

(f2)

(f3)

(F1)

wherein a, b, c, d, p, R$^1$, R$^2$, R$^3$, and R$^4$ are as defined in Item 1; P$^1$ is as defined in preparation process A; LG$^3$ is a leaving group; and P$^3$ is an amino-protecting group, wherein LG$^3$ includes, for example, halogen atom, hydroxy, and the like; P$^3$ includes, for example, amino-protecting groups described in T. W. Greene, and P. G. M. Wuts, "*Protective Groups in Organic Synthesis*", John Wiley & Sons, Inc., (1999), and the like; and the stereochemistry of the carbon with * is not inverted during reactions.

Compound (f1) is commercially available.

Compound (f2) can be prepared by a known method described in JP-A-2007-510619, *J. Chem. Soc., Chem. Commun.*, 1599-1601 (1988), *Tetrahedron Letters*, 43: 5957-5960 (2002), *Tetrahedron Asymmetry*, 2: 1263-1282 (1991), *Tetrahedron Asymmetry*, 27: 1062-1068 (2016), Comprehensive Organic Transformation 2$^{nd}$ Edition (Larock R. C., John Wiley & Sons, Inc., (1989)) or a similar method, or can be obtained as a marketed product.

(Step 1)

Compound (f3) can be prepared by reacting compound (f1) with compound (f2) such as carboxylic acid compound or acid chloride compound in the presence of an appropriate condensing agent and/or an appropriate base in an appropriate solvent.

The base used herein includes amines such as triethylamine, diisopropylethylamine, and pyridine; carbonates of alkali metal such as potassium carbonate, sodium carbonate, and sodium bicarbonate.

The condensing agent used herein is optionally selected from condensing agents commonly-used in organic synthetic chemistry, and includes preferably 1-ethyl-3-(3-dimethylaminopropyl)carbodiimide hydrochloride, 1-hydroxybenzotriazole, and the like.

The solvent used herein includes, for example, ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate, and methyl acetate; aprotic solvents such as acetonitrile, N,N-dimethylformamide, N,N-dimethylacetamide, N-methyl-2-pyrrolidinone, 1,3-dimethyl-2-imidazolidinone, and dimethylsulfoxide; halogenated hydrocarbon solvents such as dichloromethane (methylene chloride), chloroform, and 1,2-dichloroethane; and mixtures thereof, but should not be specifically limited thereto unless it reacts under the reaction condition of the present step. The solvent includes preferably tetrahydrofuran, toluene, acetonitrile, N, N-dimethylformamide, dichloromethane, and the like.

The reaction time is generally 5 minutes to 72 hours, preferably 30 minutes to 24 hours.

The reaction temperature is generally −78° C. to 200° C., preferably −78° C. to 80° C.

(Step 2)

Compound (F1) can be prepared by removing protecting group P$^3$ from compound (f3). The present step can be carried out, for example, according to a known method described in T. W. Greene, and P. G. M. Wuts, "*Protective Groups in Organic Synthesis*", John Wiley & Sons, Inc., (1999), or a similar method.

Preparation Process G

In the compound of formula (a2), the compound of formula (G1) can be prepared, for example, by the following process:

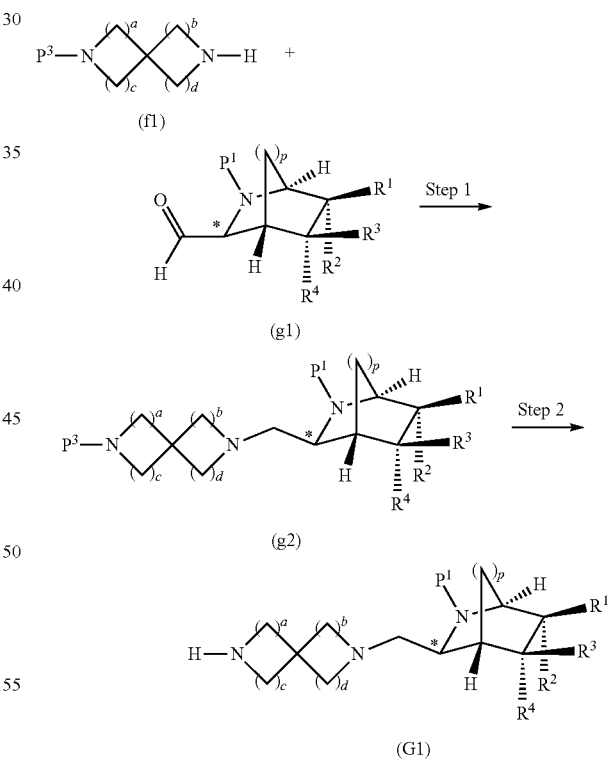

(f1)

(g1)

(g2)

(G1)

wherein a, b, c, d, p, R$^1$, R$^2$, R$^3$, and R$^4$ are as defined in Item 1; P$^1$ is as defined in preparation process A; P$^3$ is as defined in preparation process F; and the stereochemistry of the carbon with * is not inverted during reactions.

Compound (f1) is commercially available.

Compound (g1) can be obtained by a known method described in JP-A-2007-510619, *J. Chem. Soc., Chem. Commun.*, 1599-1601 (1988), *Tetrahedron Letters*, 43: 5957-

5960 (2002), *Tetrahedron Asymmetry*, 2: 1263-1282 (1991), *Tetrahedron Asymmetry*, 27: 1062-1068 (2016), R. C. Larock, "*Comprehensive Organic Transformation 2$^{nd}$ Edition*", John Wiley & Sons, Inc., (1989) or a similar method, or can be obtained as a marketed product.

(Step 1)

Compound (g2) can be prepared from compound (f1) and compound (g1) by a known method described in *J. Am. Chem. Soc.*, 93(12): 2897-2904 (1971), *J. Org. Chem.*, 37(10): 1673-1674 (1972), *J. Org. Chem.*, 61(11): 3849-3862 (1996), *Tetrahedron*, 60: 7899-7906 (2004), or a similar method.

(Step 2)

Compound (G1) can be prepared by removing protecting group P$^3$ from compound (g2). The present step can be carried out, for example, by a known method described in T. W. Greene, and P. G. M. Wuts, "*Protective Groups in Organic Synthesis*", John Wiley & Sons, Inc., (1999), or a similar method.

Preparation Process H

The compound of formula (H1) can be prepared, for example, by the following process:

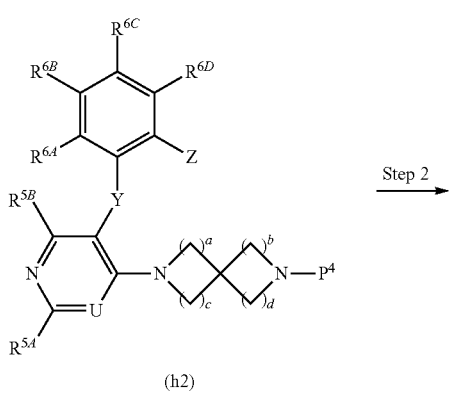

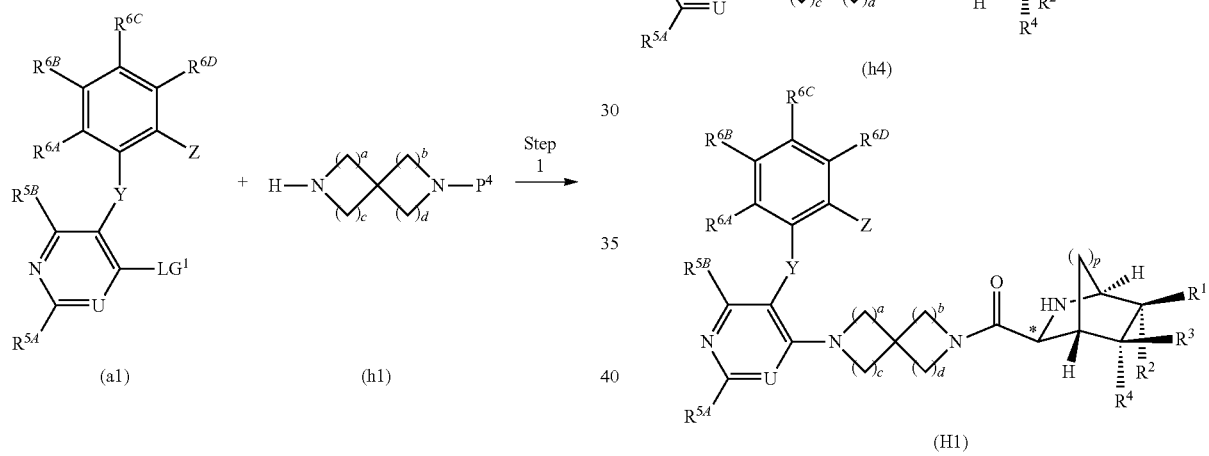

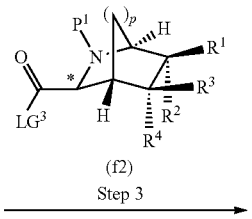

wherein a, b, c, d, p, R$^1$, R$^2$, R$^3$, R$^4$, R$^{5A}$, R$^{5B}$, R$^{6A}$, R$^{6B}$, R$^{6C}$, R$^{6D}$, U, Y, and Z are as defined in Item 1; LG$^1$ is as defined in preparation process A; LG$^3$ is as defined in preparation process F; P$^1$ is as defined in preparation process A; and P$^4$ is an amino-protecting group, wherein P$^4$ includes, for example, amino-protecting groups described in T. W. Greene, and P. G. M. Wuts, "*Protective Groups in Organic Synthesis*", John Wiley & Sons, Inc., (1999), and the like; and the stereochemistry of the carbon with * is not inverted during reactions.

Compound (h1) is commercially available.

(Step 1)

Compound (h2) can be prepared from compound (a1) and compound (h1) by the method described in step 1 of preparation process A or a similar method.

(Step 2)

Compound (h3) can be prepared by removing protecting group P$^4$ from compound (h2). The present step can be carried out, for example, by a known method described in T. W. Greene, and P. G. M. Wuts, "*Protective Groups in Organic Synthesis*", John Wiley & Sons, Inc., (1999), or a similar method.

(Step 3)

Compound (h4) can be prepared from compound (h3) and compound (f2) by the method described in step 1 of preparation process F or a similar method.

(Step 4)

Compound (H1) can be prepared by removing $P^1$ from compound (h4). The present step can be carried out, for example, by a known method described in T. W. Greene, and P. G. M. Wuts, *"Protective Groups in Organic Synthesis"*, John Wiley & Sons, Inc., (1999), or a similar method.

Preparation Process I

The compound of the present invention of formula (I1) can be prepared, for example, by the following method:

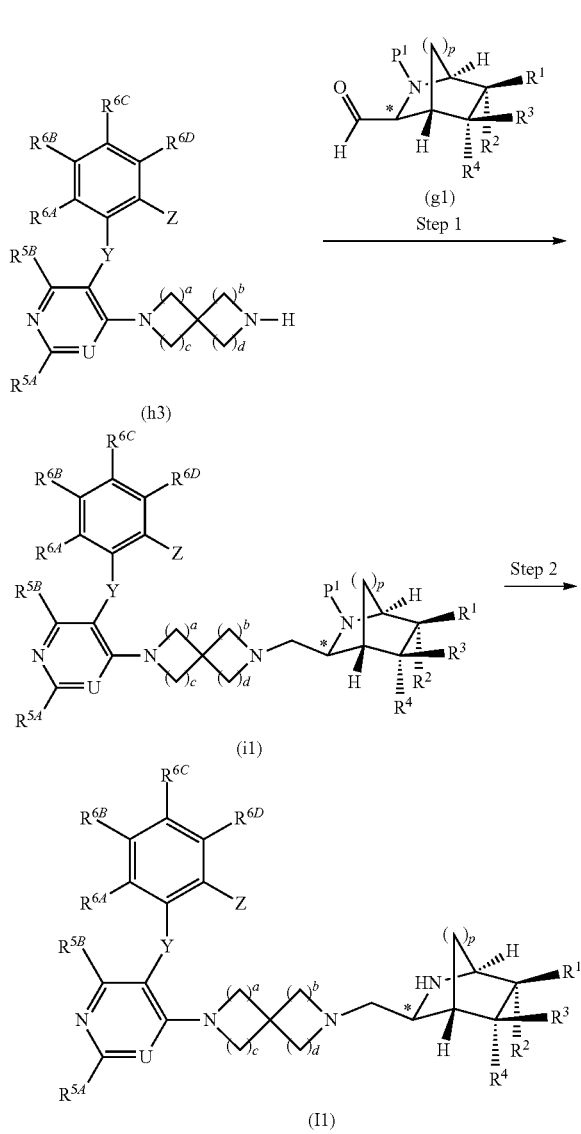

wherein a, b, c, d, p, $R^1$, $R^2$, $R^3$, $R^4$, $R^{5A}$, $R^{5B}$, $R^{6A}$, $R^{6B}$, $R^{6C}$, $R^{6D}$, U, Y, and Z are as defined in Item 1; $P^1$ is as defined in preparation process A; and the stereochemistry of the carbon with * is not inverted during reactions.

(Step 1)

Compound (i1) can be prepared from compound (h3) and compound (g1) by a known method described in step 1 of preparation process G or a similar method.

(Step 2)

Compound (I1) can be prepared by removing protecting group p from compound (i1). The present step can be carried out, for example, by a known method described in T. W. Greene, and P. G. M. Wuts, *"Protective Groups in Organic Synthesis"*, John Wiley & Sons, Inc., (1999), or a similar method.

Preparation Process J

In the compound of formula (f2), the compound of formula (J1) can be prepared, for example, by the following method:

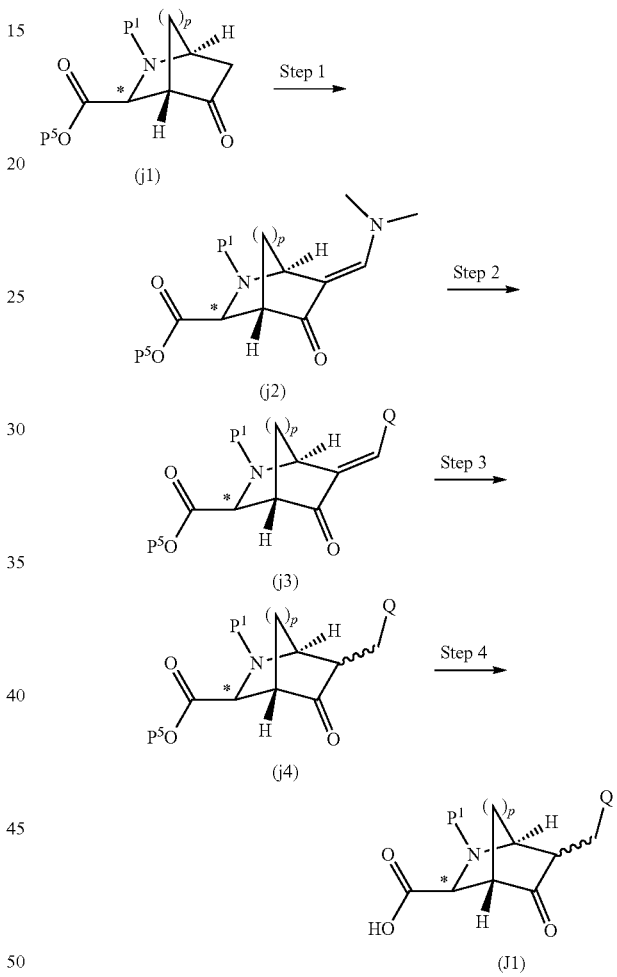

wherein p and Q are as defined in Item 1; $P^1$ is as defined in preparation process A; P5 is a protecting group of carboxylic acid, wherein $P^5$ includes, for example, carboxylic acid-protecting groups described in T. W. Greene, and P. G. M. Wuts, *"Protective Groups in Organic Synthesis"*, John Wiley & Sons, Inc., (1999), and the like; and the stereochemistry of the carbon with * is not inverted during reactions.

Compound (j1) can be prepared by a known method described in JP-A-2007-510619, *J. Chem. Soc., Chem. Commun.*, 1599-1601 (1988), *Tetrahedron Letters*, 43: 5957-5960 (2002), *Tetrahedron Asymmetry*, 2: 1263-1282 (1991), *Tetrahedron Asymmetry*, 27: 1062-1068 (2016), R. C. Larock, *"Comprehensive Organic Transformation 2nd Edition"*, John Wiley & Sons, Inc., (1989) or a similar method, or can be obtained as a marketed product.

(Step 1)

Compound (j2) can be prepared from compound (j1) by a known method described in Tetrahedron Letters, 27: 2567-2570 (1986), Synthesis, 12: 1930-1935 (2011), Bioorganic & Medicinal Chemistry Letters, 23: 4493-4500 (2013), European Journal of Organic Chemistry, 10: 2485-2490 (1999), or a similar method.

(Step 2)

Compound (j3) can be prepared from compound (j2) by a known method described in Synthetic Communications, 28: 1743-1753 (1998), Chemistry Letters, 6: 875-878 (1983), Journal of Organic Chemistry, 28: 6-16 (1963) or a similar method.

(Step 3)

Compound (j4) can be prepared from compound (j3) by a known method described in Tetrahedron Letters, 23: 477-480 (1982), Synlett, 443-444 (1995), Synlett, 96-98 (1999), Tetrahedron, 56: 2779-2788 (2000) or a similar method.

(Step 4)

Compound (J1) can be prepared by removing protecting group $P^5$ from compound (j4). The present step can be carried out, for example, by a known method described in T. W. Greene, and P. G. M. Wuts, "Protective Groups in Organic Synthesis", John Wiley & Sons, Inc., (1999), or a similar method.

Preparation Process K

In the compound of formula (f2), the compound of formula (K1) can be prepared, for example, by the following method:

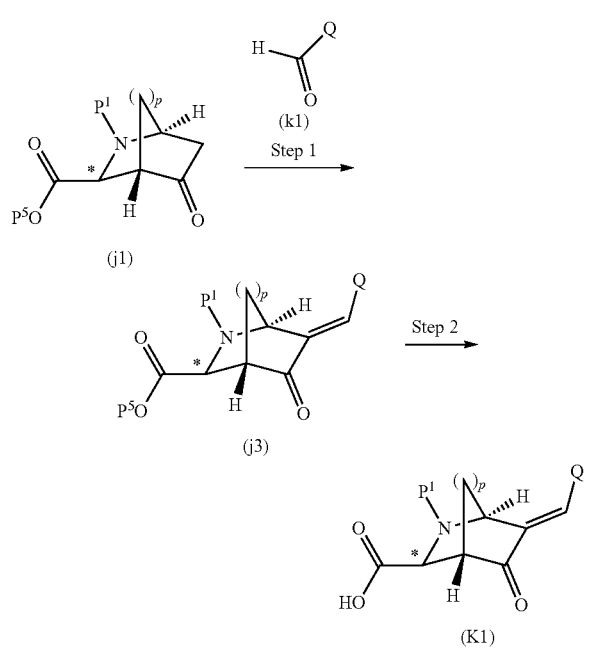

wherein p and Q are as defined in Item 1; $P^1$ is as defined in preparation process A; $P^5$ is as defined in preparation process J; and the stereochemistry of the carbon with * is not inverted during reactions.

Compound (k1) is commercially available.

(Step 1)

Compound (j3) can be prepared from compound (j1) and compound (k1) by a known method described in Journal of the American Chemical Society, 126: 14206-14216 (2004), Synthetic Communications, 20: 839-847 (1990), Synthesis, 23: 3821-3826 (2011), Advanced Synthesis & Catalysis, 352: 153-162 (2010) or a similar method.

(Step 2)

Compound (K1) can be prepared by removing protecting group $P^5$ from compound (j3). The present step can be carried out, for example, by a known method described in T. W. Greene, and P. G. M. Wuts, "Protective Groups in Organic Synthesis", John Wiley & Sons, Inc., (1999), or a similar method.

Preparation Process L

In the compound of formula (f2), the compound of formula (L1) can be prepared, for example, by the following method:

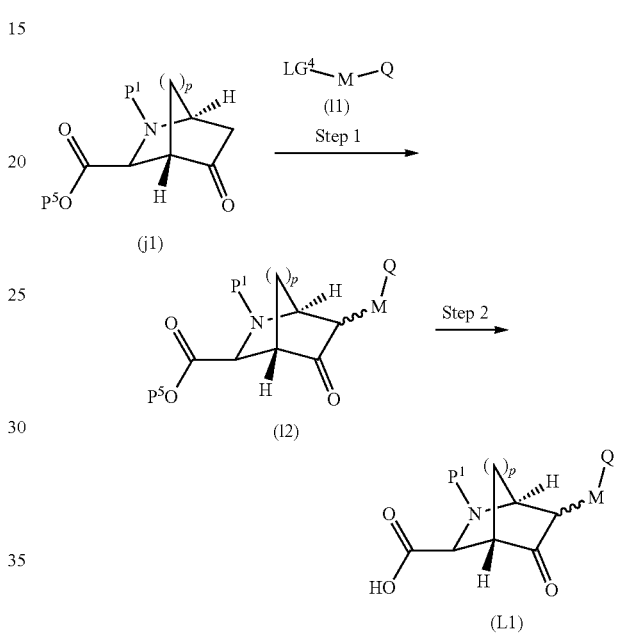

wherein p, M, and Q are as defined in Item 1; $LG^1$ is a leaving group; $P^1$ is as defined in preparation process A; $P^5$ is as defined in preparation process J, wherein $LG^1$ includes, for example, halogen atom, methanesulfonyloxy, p-toluenesulfonyloxy, trifluoromethanesulfonyloxy, phenoxy, trifluorophenoxy, tetrafluorophenoxy, pentafluorophenoxy, nitrophenoxy, and the like; and the stereochemistry of the carbon with * is not inverted during reactions.

Compound (l1) is commercially available.

(Step 1)

Compound (l2) can be prepared from compound (j1) and compound (l1) by a known method described in Journal of the American Chemical Society, 132: 1236-1237 (2010), Journal of Medicinal Chemistry, 49: 4409-4424 (2006), Advanced Synthesis & Catalysis, 357: 2803-2808 (2015), Tetrahedron Letters, 47(19): 3233-3237 (2006), Angewandte Chemie, International Edition, 44(34): 5516-5519 (2005), or a similar method.

(Step 2)

Compound (L1) can be prepared by removing protecting group $P^5$ from compound (l2). The present step can be carried out, for example, by a known method described in T. W. Greene, and P. G. M. Wuts, "Protective Groups in Organic Synthesis", John Wiley & Sons, Inc., (1999), or a similar method.

Preparation Process M

The compound of the present invention of formula (1) can be prepared, for example, by the following method:

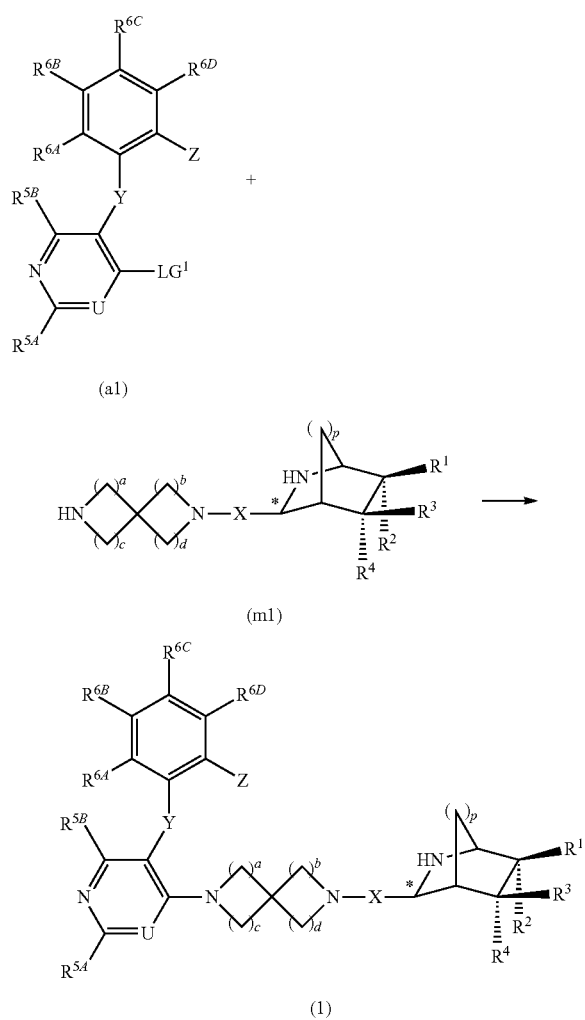

wherein a, b, c, d, p, $R^1$, $R^2$, $R^3$, $R^4$, $R^{5A}$, $R^{5B}$, $R^{6A}$, $R^{6B}$, $R^{6C}$, $R^{6D}$, U, X, Y, and Z are as defined in Item 1; $LG^1$ is as defined in preparation process A; and the stereochemistry of the carbon with * is not inverted during reactions.

Compound (1) can be prepared from compound (a1) and compound (m1) which is prepared by the following preparation process, by a known method described in step 1 of preparation process A or a similar method.

Compound (m1) used herein can be obtained by the following preparation process N (as compound (N1)), or by the following preparation process O (compound (O1)).

Preparation Process N

In the compound of formula (m1), the compound of formula (N1) can be prepared, for example, by the following method:

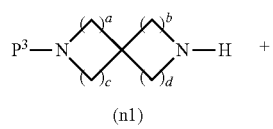

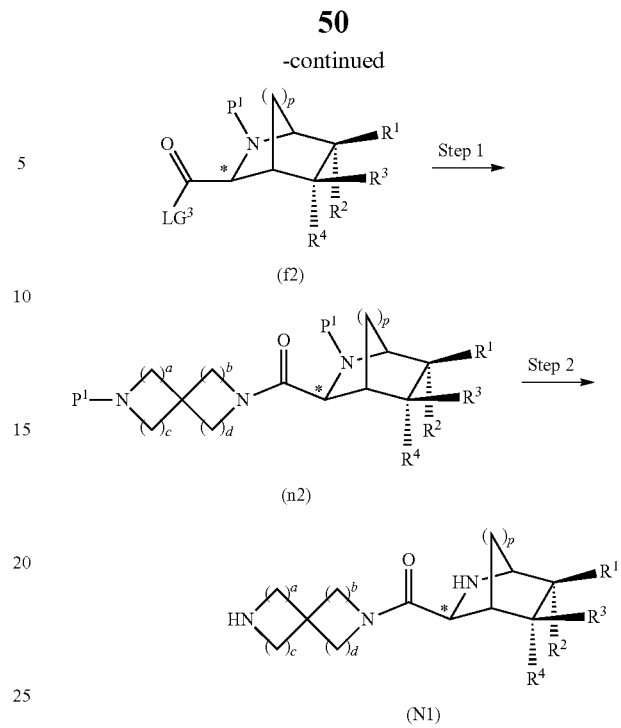

wherein a, b, c, d, p, $R^1$, $R^2$, $R^3$, and $R^4$ are as defined in Item 1; $LG^3$ is as defined in preparation process F; $P^1$ is as defined in preparation process A; and the stereochemistry of the carbon with * is not inverted during reactions.

Compound (n1) is commercially available.

(Step 1)

Compound (n2) can be prepared from compound (n1) and compound (f2) by the method described in step 1 of preparation process F or a similar method.

(Step 2)

Compound (N1) can be prepared by removing protecting group $P^1$ from compound (n2). The present step can be carried out, for example, by a known method described in T. W. Greene, and P. G. M. Wuts, "Protective Groups in Organic Synthesis", John Wiley & Sons, Inc., (1999), or a similar method.

Preparation Process O

In the compound of formula (m1), the compound of formula (O1) can be prepared, for example, by the following method:

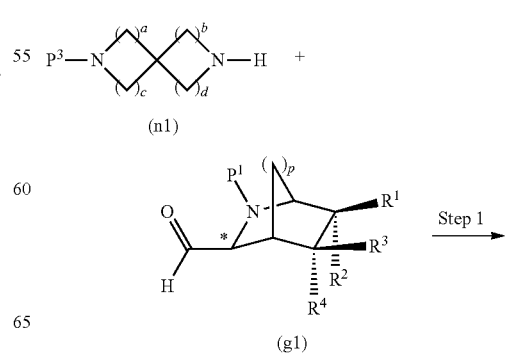

-continued

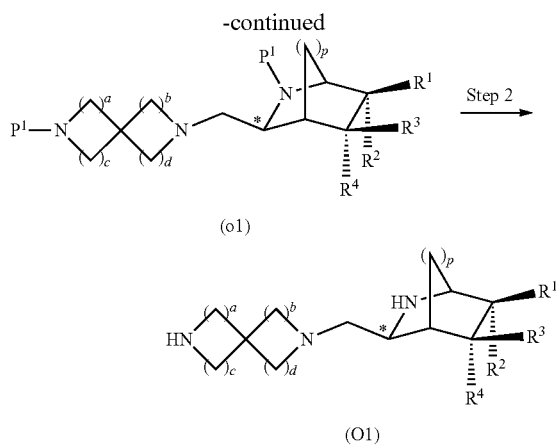

wherein a, b, c, d, p, $R^1$, $R^2$, $R^3$, and $R^4$ are as defined in Item 1; $P^1$ is as defined in preparation process A; and the stereochemistry of the carbon with * is not inverted during reactions.

(Step 1)

Compound (o1) can be prepared from compound (n1) and compound (g1) by a known method described in step 1 of preparation process G or a similar method.

(Step 2)

Compound (O1) can be prepared by removing protecting group P1 from compound (o1). The present step can be carried out, for example, by a known method described in T. W. Greene, and P. G. M. Wuts, "*Protective Groups in Organic Synthesis*", John Wiley & Sons, Inc., (1999), or a similar method.

In the above preparation processes, starting materials or intermediates which are not described for preparation processes can be obtained as marketed products, or can be prepared from marketed products by a method well-known to those skilled in the art.

In each reaction described above, protecting groups can be used as necessary, even if the use of protecting groups is not explicitly stated. For example, when any one or more functional groups other than reaction sites are converted to undesired forms under the reaction condition, or the process described above cannot be carried out properly without protecting groups, protecting groups can be used to protect groups other than reaction sites as necessary, and can be deprotected after the reaction is completed or a series of reactions have been carried out to obtain the desired compound.

As such protecting groups, for example, the groups described in T. W. Greene, and P. G. M. Wuts, "*Protective Groups in Organic Synthesis*", John Wiley & Sons, Inc., (1999), and the like may be used. Examples of amino-protecting groups include, for example, benzyloxycarbonyl, tert-butoxycarbonyl, acetyl, benzyl, and the like. Examples of hydroxy-protecting groups include, for example, trialkylsilyl such as trimethylsilyl and tert-butyldimethylsilyl, acetyl, benzyl, and the like.

The introduction and elimination of protecting groups can be carried out by a method commonly-used in synthetic organic chemistry (for example, see "Protective Groups in Organic Synthesis" described above), or a similar method.

In the present specification, protecting groups, condensing agents and the like may be described in an abbreviated form according to IUPAC-IUB (Biochemical nomenclature committee) commonly-used herein. It should be understood that the names of compounds used in the present specification do not necessarily follow the IUPAC nomenclature.

The intermediates or the desired compounds which are described in the above preparation processes can be transformed to other compounds which fall within the present invention by optionally converting their functional groups to other groups (for example, the conversion from amino, hydroxy, carbonyl, halogen atom, and the like, while protecting or deprotecting other functional groups as necessary). The conversion of functional groups can be carried out by a general method which are commonly used (see, for example, R. C. Larock, "*Comprehensive Organic Transformations*", John Wiley & Sons Inc. (1999)).

The intermediates and the desired compounds described above can be isolated and purified by a purification method commonly-used in organic synthetic chemistry (for example, neutralization, filtration, extraction, washing, drying, enrichment, recrystallization, various chromatography, and the like). In addition, intermediates may be used in next reaction without further purification.

The "pharmaceutically acceptable salt" includes acid addition salts and base addition salts. For example, the acid addition salt includes inorganic acid salts such as hydrochloride, hydrobromide, sulfate, hydroiodide, nitrate, and phosphate; or organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, and camphorsulfonate. The base addition salt includes inorganic base salts such as sodium salts, potassium salts, calcium salts, magnesium salts, barium salts, and aluminum salts; and organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N,N-dibenzylethylamine. The "pharmaceutically acceptable salt" also includes amino acid salts of basic or acidic amino acids such as arginine, lysine, ornithine, aspartate, and glutamate.

The suitable salts of starting materials and intermediates and acceptable salts of drug substances are conventional non-toxic salts. The suitable salt includes, for example, acid addition salts such as organic acid salts (including acetate, trifluoroacetate, maleate, fumarate, citrate, tartrate, methanesulfonate, benzenesulfonate, formate, and p-toluenesulfonate) and inorganic acid salts (including hydrochloride, hydrobromide, hydroiodide, sulfate, nitrate, and phosphate); salts with amino acids (including arginine, aspartate, and glutamate); alkali metal salts (including sodium salts, and potassium salts); alkaline earth metal salts (including calcium salts, and magnesium salts); ammonium salts; organic base salts (including trimethylamine salts, triethylamine salts, pyridine salts, picolinate, dicyclohexylamine salts, and N,N'-dienzylethylenediamine salts); and other salts which a person skilled in the art can optionally select.

In the present invention, the "hydrogen atom" includes 1H and $^2$H (D), and the compound of formula (1) encompasses deuterated compounds in which any one or more 1H in the compound of formula (1) are replaced with $^2$H (D).

The present invention encompasses compounds of formula (1) or pharmaceutically acceptable salts thereof. The compound of the present invention may exist in a form of hydrate and/or solvate of various solvents, including ethanolate, and these hydrate and/or solvate are included in the compound of the present invention.

The compound of the present invention encompasses optical isomers based on an optically active center, atropisomers based on axial or planar chirality caused by restriction of intramolecular rotation, and all other isomers which can exist as stereoisomers, tautomers, and geometric isomers, and crystalline forms in various states, and mixtures thereof.

Especially, each optical isomer and atropisomer can be obtained as a racemate, or as an optically active substance when an optically active starting material or intermediate is used. Racemates of corresponding starting materials, intermediates, or final products can also be physically or chemically resolved into optical enantiomers by a known isolating method such as a method with an optically active column and a fractional crystallization method, at an appropriate step in the above preparation processes, if necessary. These methods for resolving enantiomers include a diastereomer method in which, for example, a racemate is reacted with an optically active resolving agent to synthesize 2 kinds of diastereomers, which are resolved by fractional crystallization or a similar method through different physical properties.

If the compound of the present invention should be obtained as a pharmaceutically acceptable salt thereof, when the compound of formula (1) is obtained as a pharmaceutically acceptable salt, it may be purified without further reaction, and when it is obtained in a free form, it may be dissolved or suspended in an appropriate organic solvent and an acid or base may be added therein to form a salt by a common method.

In the present invention, the "agent used in combination" is an antitumor medicament which can be used in combination with the compound of the present invention or can be combined with the compound of the present invention in a pharmaceutical composition. The "combination drug" includes, for example, an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, an biological response modifier, a hormone preparation, an immune checkpoint inhibitor, an epigenetics-associated molecular inhibitor, a protein post-translational modification inhibitor, and other antitumor medicaments. Examples of the "combination drug" include, for example, azacytidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans retinoic acid, tamibarotene, cisplatin, carboplatin, oxaliplatin, irinotecan, bleomycin, mitomycin C, methotrexate, paclitaxel, docetaxel, gemcitabine, tamoxifen, thiotepa, tegafur, fluorouracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, atezolizumab, mogamulizumab, alemtuzumab, ofatumumab, ipilimumab, ramucirumab, brentuximab vedotin, Gemtuzumab ozogamicin, inotuzumab ozogamicin, and the like.

The administration route of the compound of the present invention may be oral, parenteral, intrarectal, or ophthalmic administration, and the daily dose depends on the type of compounds, administration methods, the condition or age of patients, and the like. For example, in the case of oral administration, about 0.01 to 1000 mg, more preferably about 0.1 to 500 mg per kg body weight of a human or mammal can be usually administered in one to several portions. In the case of parenteral administration such as intravenous injection, for example, about 0.01 mg to 300 mg, more preferably about 1 mg to 100 mg per kg body weight of a human or mammal can be usually administrated.

The compound of the present invention can be orally or parenterally administrated directly or as a suitable drug formulation. The dosage form includes, for example, a tablet, a capsule, a powder, a granule, a liquid, a suspension, an injection, a patch, a poultice, and the like, but it is not limited to them. The drug formulation is prepared by a common method using pharmaceutically acceptable additives.

As the additive, an excipient, a disintegrant, a binder, a fluidizer, a lubricant, a coating agent, a solubilizer, a solubilizing adjuvant, a thickener, a dispersant, a stabilizing agent, a sweetening agent, a flavor, and the like may be used, depending on purpose. The additive used herein includes, for example, lactose, mannitol, crystalline cellulose, low-substituted hydroxypropylcellulose, corn starch, partially-pregelatinized starch, carmellose calcium, croscarmellose sodium, hydroxypropylcellulose, hydroxypropylmethylcellulose, polyvinyl alcohol, magnesium stearate, sodium stearyl fumarate, polyethylene glycol, propylene glycol, titanium oxide, talc, and the like.

EXAMPLES

The present invention is explained in more detail in the following by referring to Reference examples, Examples, and Tests; however, the technical scope of the present invention should not be limited thereto.

In the present specification, the abbreviations shown below may be used.
THF: tetrahydrofuran
TFA: trifluoroacetic acid
DMF: N,N-dimethylformamide
DMSO: dimethylsulfoxide
MeCN: acetonitrile
Me: methyl
Et: ethyl
Ph: phenyl
Bn: benzyl
Boc: tert-butoxycarbonyl
n-: normal-
tert-: tertiary-
p-: para-
BINAP: 2,2'-bis(diphenylphosphino)-1,1'-binaphthyl
$Pd_2(dba)_3$: tris(dibenzylideneacetone)dipalladium(0)
Ac: acetyl
dppf: 1,1'-bis(diphenylphosphino)ferrocene
Xantphos: 4,5-bis(diphenylphosphino)-9,9-dimethylxanthene
Dess-Martin reagent: Dess-Martin periodinane (1,1,1-triacetoxy-1,1-dihydro-1,2-benziodoxol-3-(1H)-one)
Petasis reagent: bis(cyclopentadienyl)dimethyltitanium
Bredereck reagent: tert-butoxy-bis(dimethylamino)methane
HATU: 1-[bis(dimethylamino)methylene]-1H-1,2,3-triazolo[4,5-b]pyridinium 3-oxide hexafluorophosphate
WSCI.HCl: 1-(3-dimethylaminopropyl)-3-ethylcarbodiimide hydrochloride
HOBt: 1-hydroxybenzotriazole NMR (Nuclear Magnetic Resonance) data used for identification of compounds were obtained with a JNM-ECS400 type nuclear magnetic resonance instrument (400 MHz) from JEOL Ltd.

The symbols used in NMR are defined as follows, s: singlet, d: doublet, dd: doublet of doublet, t: triplet, td: triplet of doublet, q: quartet, m: multiplet, br: broad, brs: broad singlet, brm: broad multiplet, and J: coupling constant.

Analytical conditions of LC/MS (Liquid Chromatography-Mass Spectrometry) used for identification of compounds are shown below. In observed mass spectrometry values, monoisotopic mass (exact mass consisting of only main isotope) is shown in $[M+H]^+$, $[M-H]^-$, or $[M+2H]^{2+}$, etc., and retention time is shown as Rt (minutes).

The analytical conditions of LC/MS:
Analytical Condition A
Detection apparatus: ACQUITY™ SQ detector (Waters Corporation)
HPLC: ACQUITY™ UPLC system
Column: Waters ACQUITY™ UPLC BEH C18 (1.7 μm, 2.1 mm×30 mm)
Solvent: A: 0.06% formic acid/$H_2O$, B: 0.06% formic acid/MeCN
Gradient condition: 0.0 to 1.3 minutes Linear gradient of B 2% to B 96%
Flow rate: 0.8 mL/min
UV: 220 nm and 254 nm
Column temperature: 40° C.
Analytical Condition B
Detection apparatus: LCMS-2020 (Shimadzu Corporation)
HPLC: Nexera X2
Column: Phenomenex Kinetex™ 1.7 μm C18 (50 mm×2.1 mm)
Solvent: A: 0.05% TFA/$H_2O$, B: MeCN
Gradient condition: 0.0 to 1.7 minutes Linear gradient of B 10% to B 99%
Flow rate: 0.5 mL/min
UV: 220 nm and 254 nm
Column temperature: 40° C.

Powder X-ray diffraction measurements in Examples were carried out in the following conditions. The obtained diffraction patterns (XRD spectra) are shown in FIG. 1 to FIG. 5.

Crystalline forms may be identified based on distinctive diffraction peaks of each crystal shown in diffraction diagrams of FIG. 1 to FIG. 5.

Main diffraction peaks and distinctive diffraction peaks which are identified from diffraction patterns of FIG. 1 to FIG. 5 are respectively shown below. Diffraction peak values in diffraction angle 2θ (°) described in the following Examples include some measurement errors depending on detection apparatus or measurement conditions etc. Specifically, measurement errors may be within ±0.2, preferably within ±0.1.

Measurement Method for Powder X-Ray Diffraction:
Detection apparatus: Spectris Power X-ray diffraction system Empyrian
X-Ray tube: CuKα (wavelength: 1.54 angstrom)
Tube voltage: 45 kV
Tube current: 40 mA
Measurement range: 40 to 400 (2θ)

Step width: 0.013°
Integrated time: 100 sec/step

Reference Example 1

2-[(4-Chloropyrimidin-5-yl)oxy]-5-fluoro-N,N-di(propan-2-yl)benzamide

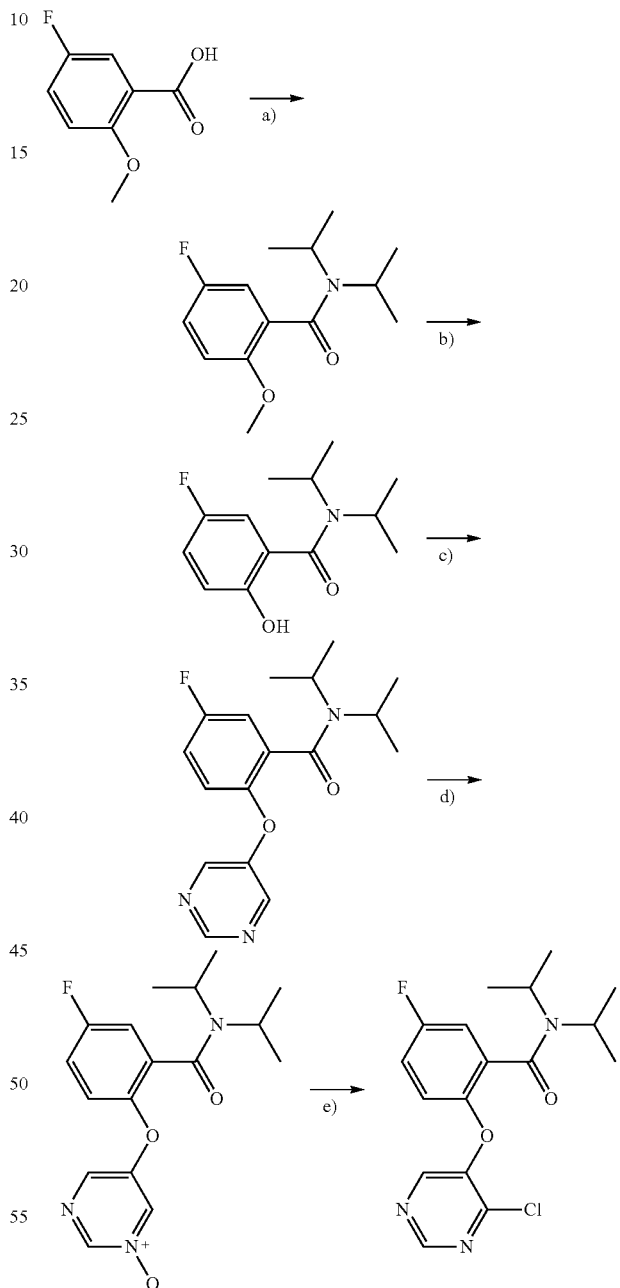

Reference example 1 a) Preparation of 5-fluoro-2-methoxy-N,N-di(propan-2-yl)benzamide

5-Fluoro-2-methoxybenzoic acid (100 g) was dissolved in dichloromethane (1.0 L), and diisopropylamine (251 mL) and HATU (235 g) were added thereto at 0° C. The mixture was stirred at room temperature for a day. The reaction mixture was quenched with 5 mol/L aqueous hydrochloric acid. The resulting solution was extracted twice with ethyl acetate. The resulting organic layer was washed with brine, dried over magnesium sulfate, and filtrated, and the solvent was removed under reduced pressure to yield a crude product of the titled compound (200 g).

LC-MS; [M+H]$^+$ 254.0/Rt (minutes) 0.96 (Analytical condition A)

b) Preparation of 5-fluoro-2-hydroxy-N,N-di(propan-2-yl)benzamide

5-Fluoro-2-methoxy-N,N-di(propan-2-yl)benzamide (70.0 g) was dissolved in dichloromethane (400 mL), and boron tribromide (39.2 mL) were added thereto at 0° C. The mixture was stirred at 0° C. for a day. The mixture was quenched with 8 mol/L aqueous ammonia. The resulting solution was extracted twice with chloroform. The resulting organic layer was washed with brine, dried over magnesium sulfate, and filtered, and the solvent was removed under reduced pressure to yield the titled compound (56.0 g).

LC-MS; [M+H]$^+$ 240.0/Rt (minutes) 0.85 (Analytical condition A)

c) Preparation of 5-fluoro-N,N-di(propan-2-yl)-2-[(pyrimidin-5-yl)oxy]benzamide

5-Fluoro-2-hydroxy-N,N-di(propan-2-yl)benzamide (118.0 g) was suspended in DMF (250 mL), and 5-bromopyrimidine (35.9 g) and cesium carbonate (73.5 g) were added thereto at room temperature. The mixture was stirred with heating under reflux for a day. After cooling, the reaction mixture was concentrated under reduced pressure, and the residue was quenched by addition of saturated aqueous sodium bicarbonate. The resulting solution was extracted twice with ethyl acetate. The resulting organic layer was washed with brine, dried over magnesium sulfate, and filtered, and the solvent was removed under reduced pressure. The residue was purified by silica gel column chromatography (hexane/ethyl acetate) to yield the titled compound (20.0 g).

LC-MS; [M+H]$^+$ 317.7/Rt (minutes) 0.86 (Analytical condition A)

d) Preparation of 5-fluoro-2-[(1-oxo-1λ$^5$-pyrimidin-5-yl)oxy]-N,N-di(propan-2-yl)benzamide 5-Fluoro-N,N-di(propan-2-yl)-2-[(pyrimidin-5-yl)oxy]benzamide (72.1 g) is dissolved in dichloromethane (900 mL), and meta-chloroperoxybenzoic acid (112 g) was added thereto at 0° C. The mixture was stirred at 0° C. for 2 days. The reaction was quenched with tributylphosphine (56.7 mL) and saturated aqueous sodium bicarbonate. After cooling, dichloromethane was removed under reduced pressure, and the resulting solution was extracted twice with ethyl acetate. The resulting organic layer was washed with brine, dried over magnesium sulfate, and filtered, and the solvent was removed under reduced pressure. The residue was purified by silica gel column chromatography (chloroform/methanol) to yield the titled compound (42.3 g).

LC-MS; [M+H]$^+$ 334.0/Rt (minutes) 0.76 (Analytical condition A)

e) Preparation of 2-[(4-chloropyrimidin-5-yl)oxy]-5-fluoro-N,N-di(propan-2-yl)benzamide (Reference Example 1)

5-Fluoro-2-[(1-oxo-1λ$^5$-pyrimidin-5-yl)oxy]-N,N-di(propan-2-yl)benzamide (36.0 g) was dissolved in chloroform (300 mL), and N,N-diisopropylethylamine (37.6 mL) and phosphoryl chloride (40 mL) were added thereto at 0° C. The mixture was stirred at 0° C. for 6 hours. After cooling, the reaction mixture was concentrated under reduced pressure, and quenched by addition of saturated aqueous sodium bicarbonate. The resulting solution was extracted twice with ethyl acetate. The resulting organic layer was washed with brine, dried over magnesium sulfate, and filtered, and the solvent was removed under reduced pressure. The residue was purified by silica gel column chromatography (hexane/ethyl acetate) to yield the titled compound (27.8 g).

$^1$H-NMR (DMSO-D$_6$) δ: 8.77 (1H, s), 8.24 (1H, s), 7.53-7.30 (3H, m), 3.68-3.61 (1H, m), 3.54-3.48 (1H, m), 1.37 (3H, d, J=6.7 Hz), 1.19 (3H, d, J=7.3 Hz), 1.08 (6H, d, J=6.7 Hz).

LC-MS; [M+H]$^+$ 351.9/Rt (minutes) 1.00 (Analytical condition A)

Reference Example 2

2-{[4-(2,7-Diazaspiro[3.5]nonan-2-yl)pyrimidin-5-yl]oxy}-5-fluoro-N,N-di(propan-2-yl)benzamide

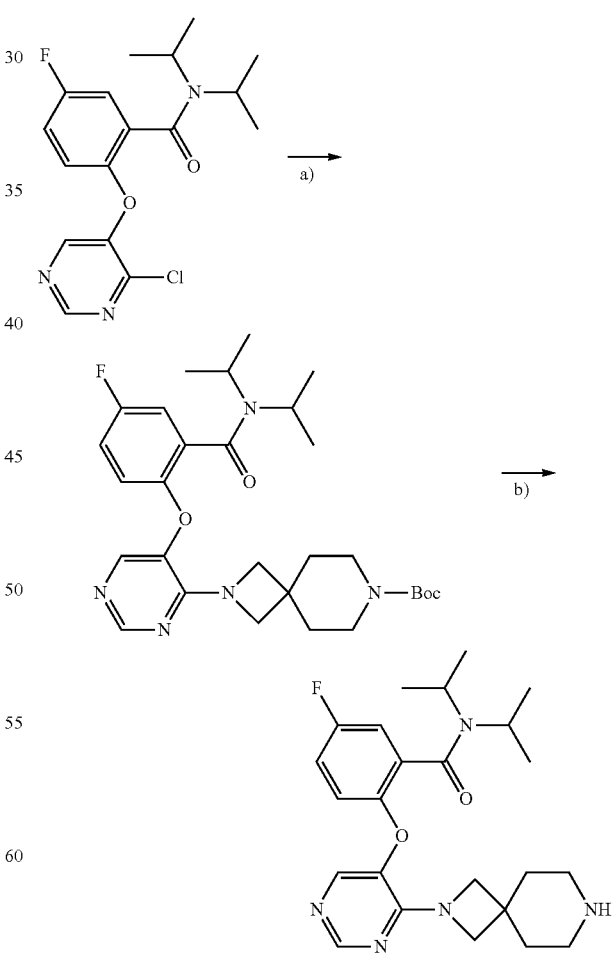

Reference example 2 a) Preparation of tert-butyl 2-(5-{2-[di(propan-2-yl) carbamoyl]-4-fluorophenoxy}pyrimidin-4-yl)-2,7-diazaspiro[3.5]nonane-7-carboxylate 2-[(4-Chloropyrimidin-5-yl)oxy]-5-fluoro-N,N-di(propan-2-yl)benzamide (27.0 g) was dissolved in 2-propanol (500 mL), and N,N-diisopropylethylamine (40.1 mL) and tert-butyl 2,7-diazaspiro[3.5]nonane-7-carboxylate hydrochloride (30.3 g) were added thereto at 0° C. The mixture was stirred at room temperature for 6 hours. The reaction mixture was concentrated under reduced pressure, and the residue was purified by silica gel column chromatography (hexane/ethyl acetate) to yield the titled compound (33.0 g).

LC-MS; [M+H]+ 542.1/Rt (minutes) 1.23 (Analytical condition A)

b) Preparation of 2-{[4-(2,7-diazaspiro[3.5]nonan-2-yl)pyrimidin-5-yl]oxy}-5-fluoro-N,N-di(propan-2-yl)benzamide (Reference Example 2)

tert-Butyl 2-(5-{2-[di(propan-2-yl)carbamoyl]-4-fluorophenoxy}pyrimidin-4-yl)-2,7-diazaspiro[3.5]nonane-7-carboxylate (44.0 g) was dissolved in dichloromethane (500 mL), and TFA (65 mL) was added thereto at 0° C. The mixture was stirred at room temperature for 12 hours. The reaction mixture was concentrated under reduced pressure, and the residue was purified by amine-silica gel column chromatography (chloroform/methanol) to yield the titled compound (35.0 g).

1H-NMR (DMSO-D6) δ: 8.26 (1H, s), 7.73 (1H, s), 7.24-7.19 (2H, m), 7.03-7.00 (1H, m), 3.87-3.78 (4H, m), 3.71-3.67 (1H, m), 3.54-3.51 (1H, m), 2.58-2.55 (4H, m), 1.59-1.56 (4H, m), 1.44 (3H, d, J=6.7 Hz), 1.35 (3H, d, J=6.7 Hz), 1.09 (3H, d, J=6.7 Hz), 1.00 (3H, d, J=6.7 Hz).

LC-MS; [M+H]+ 442.3/Rt (minutes) 1.33 (Analytical condition B)

Reference Example 3

2-{[4-(2,6-Diazaspiro[3.3]heptan-2-yl)pyrimidin-5-yl]oxy}-5-fluoro-N,N-di(propan-2-yl)benzamide

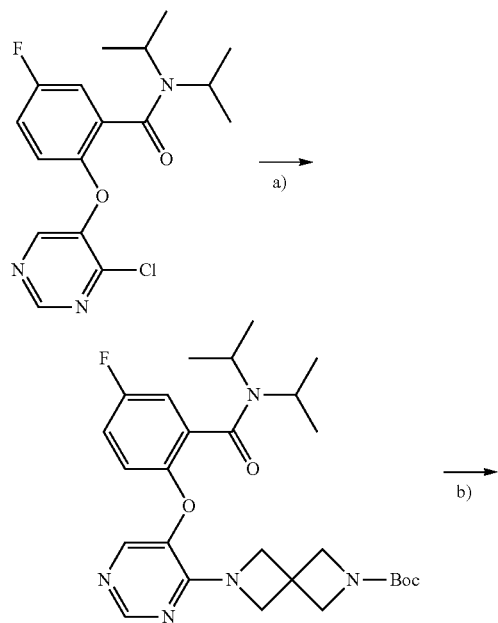

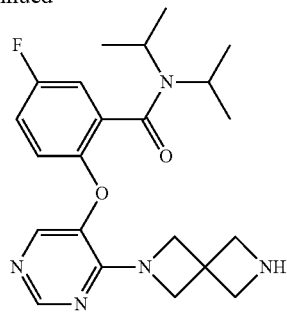

Reference example 3 a) Preparation of tert-butyl 6-(5-{2-[di(propan-2-yl) carbamoyl]-4-fluorophenoxy}pyrimidin-4-yl)-2,6-diazaspiro[3.3]heptane-2-carboxylate The titled compound (1.4 g) was prepared according to a similar procedure to step a) of Reference example 2 by using 2-[(4-chloropyrimidin-5-yl)oxy]-5-fluoro-N,N-di(propan-2-yl)benzamide (1.0 g) and 2,6-diazaspiro[3.3]heptane-2-carboxylic acid tert-butyl ester hemioxalate (1.0 g).

LC-MS; [M+H]+ 514.1/Rt (minutes) 0.96 (Analytical condition A)

b) Preparation of 2-{[4-(2,6-diazaspiro[3.3]heptan-2-yl)pyrimidin-5-yl]oxy}-5-fluoro-N,N-di(propan-2-yl)benzamide (Reference Example 3)

The titled compound (1.0 g) was prepared according to a similar procedure to step b) of Reference example 2 by using tert-butyl 6-(5-{2-[di(propan-2-yl)carbamoyl]-4-fluorophenoxy}pyrimidin-4-yl)-2,6-diazaspiro[3.3]heptane-2-carboxylate (1.4 g).

1H-NMR (DMSO-D6) δ: 8.26 (1H, s), 7.74 (1H, s), 7.23-7.17 (2H, m), 6.99-6.96 (1H, m), 4.25-4.23 (2H, m), 4.15-4.12 (2H, m), 3.69-3.66 (1H, m), 3.52-3.50 (5H, m), 1.43 (3H, d, J=6.7 Hz), 1.33 (3H, d, J=6.7 Hz), 1.07 (3H, d, J=6.7 Hz), 0.99 (3H, d, J=6.7 Hz).

LC-MS; [M+2H]2+ 207.5/Rt (minutes) 0.64 (Analytical condition A)

Reference Example 4

2-{[4-(2,7-Diazaspiro[4.4]nonan-2-yl)pyrimidin-5-yl]oxy}-5-fluoro-N,N-di(propan-2-yl)benzamide

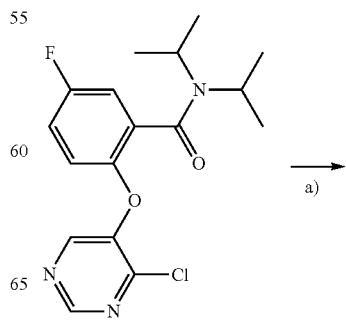

-continued

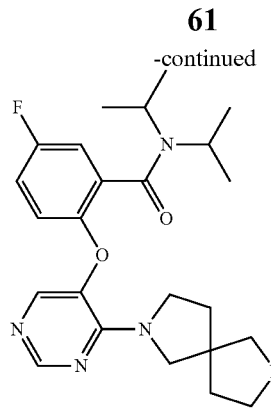

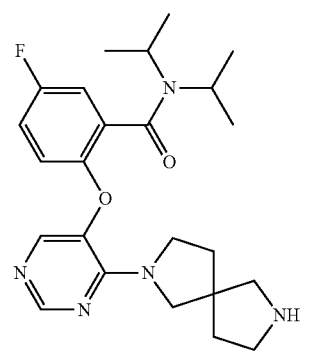

Reference example 4 a) Preparation of tert-butyl 7-(5-{2-[di(propan-2-yl) carbamoyl]-4-fluorophenoxy}pyrimidin-4-yl)-2,7-diazaspiro[4.4]nonane-2-carboxylate 2-[(4-Chloropyrimidin-5-yl)oxy]-5-fluoro-N,N-di(propan-2-yl)benzamide (150 mg) was dissolved in 2-propanol (10 mL), and triethylamine (0.2 mL) and tert-butyl 2,7-diazaspiro[4.4]nonane-2-carboxylate (193 mg) were added thereto at 0° C. The mixture was stirred at room temperature for 6 hours. The reaction mixture was concentrated under reduced pressure, and the residue was purified by silica gel column chromatography (hexane/ethyl acetate) to yield the titled compound (169 mg).

LC-MS; [M+H]$^+$ 542.1/Rt (minutes) 1.22 (Analytical condition A)

b) Preparation of 2-{[4-(2,7-diazaspiro[4.4]nonan-2-yl)pyrimidin-5-yl]oxy}-5-fluoro-N,N-di(propan-2-yl)benzamide (Reference Example 4)

tert-Butyl 7-(5-{2-[di(propan-2-yl)carbamoyl]-4-fluorophenoxy}pyrimidin-4-yl)-2,7-diazaspiro[4.4]nonane-2-carboxylate (169 mg) was dissolved in dichloromethane (10 mL), and TFA (2.0 mL) was added thereto at 0° C. The mixture was stirred at room temperature for 12 hours. The reaction mixture was concentrated under reduced pressure, and the residue was purified by amine-silica gel column chromatography (chloroform/methanol) to yield the titled compound (122 mg).

LC-MS; [M+H]$^+$ 442.3/Rt (minutes) 1.12 (Analytical condition A)

Reference Example 5

(1S,3S,4S,5R)-2-(tert-Butoxycarbonyl)-5-hydroxy-2-azabicyclo[2.2.2]octane-3-carboxylic Acid Reference Example 6

(1S,3S,4R,6S)-2-(tert-Butoxycarbonyl)-6-hydroxy-2-azabicyclo[2.2.2]octane-3-carboxylic acid

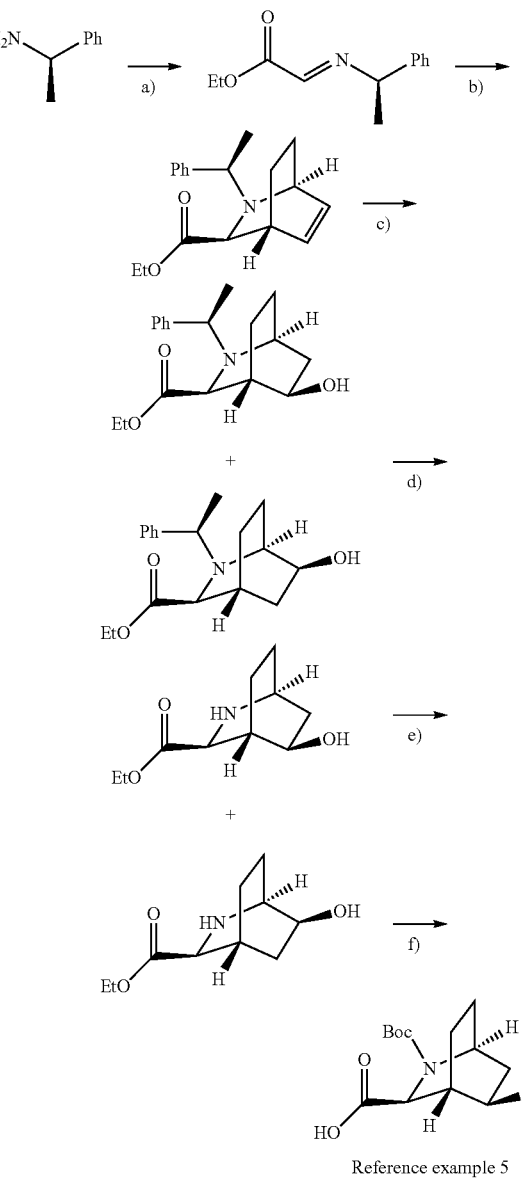

Reference example 5

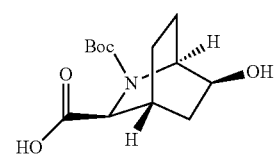

Reference example 6 a) Preparation of ethyl (2E)-{[(1R)-1-phenylethyl]imino}acetate

To (R)-1-phenylethylamine (63 mL) was added ethyl oxoacetate (100 mL), and the mixture was stirred at room temperature for an hour, and concentrated under reduced pressure to yield a crude produce of the titled compound. The resulting compound was used without purification in the next reaction.

b) Preparation of ethyl (1S,3S,4R)-2-[(1R)-1-phenylethyl]-2-azabicyclo[2.2.2]oct-5-ene-3-carboxylate To a solution of crude ethyl (2E)-{[(R)-1-phenylethyl]imino}acetate obtained in the above step a) in dichloromethane (475 mL) were added molecular sieves 4A (powder, 10 g), and the reaction mixture was cooled to −70° C. Trifluoroacetic acid (32 mL) and boron trifluoride-diethyl ether complex (53 mL) were added dropwise to the reaction mixture, and the mixture was stirred for 15 minutes, and 1,3-cyclohexadiene (42 mL) was added dropwise thereto. The reaction mixture was warmed to room temperature, and stirred overnight. To the reaction mixture was added saturated aqueous sodium bicarbonate, and the mixture was extracted with ethyl acetate. The organic layer was washed with saturated aqueous sodium bicarbonate. To the organic layer was added sodium sulfate, and the mixture was dried and filtered. The solvent was removed under reduced pressure. The residue was purified by silica gel column chromatography (hexane/ethyl acetate) to yield the titled compound (59.4 g).
LC-MS; [M+H]$^+$ 286.2/Rt (minutes) 0.53 (Analytical condition A)

c) Preparation of a mixture of ethyl (1S,3S,4S,5R)-5-hydroxy-2-[(1R)-1-phenylethyl]-2-azabicyclo[2.2.]octane-3-carboxylate and ethyl (1S,3S,4R,6S)-6-hydroxy-2-[(1R)-1-phenylethyl]-2-azabicyclo[2.2.2]octane-3-carboxylate To a solution of ethyl (1S,3S,4R)-2-[(1R)-1-phenylethyl]-2-azabicyclo[2.2.2]oct-5-ene-3-carboxylate (85.5 g) in THF (500 mL) was added dropwise 1.0 mol/L borane-THF complex (300 mL) at 0 to 5° C., and the mixture was stirred at room temperature overnight. To the reaction mixture were added 3 mol/L aqueous sodium hydroxide (62 mL) and 30% aqueous hydrogen peroxide (62 mL) under ice-cooling, and the mixture was stirred for 30 minutes. Aqueous sodium thiosulfate was added thereto, and the mixture was stirred for an hour. To the reaction mixture was added ethyl acetate/chloroform, and the mixture was separated with a separating funnel. The organic layer was washed with brine. The organic layer was dried over sodium sulfate and filtered, and the solvent was removed under reduced pressure. The residue was purified by silica gel column chromatography (hexane/ethyl acetate) to yield a crude product of the titled compound (51.7 g) as a mixture of regioisomers.
LC-MS; [M+H]$^+$ 304.2/Rt (minutes) 0.53 (Analytical condition A)

d) Preparation of ethyl (1S,3S,4S,5R)-5-hydroxy-2-azabicyclo[2.2.2]octane-3-carboxylate and ethyl (1S,3S,4R,6S)-6-hydroxy-2-azabicyclo[2.2.2]octane-3-carboxylate To a solution of the mixed product (51.7 g) obtained in the above step c) in ethanol (500 mL) was added 10% palladium hydroxide (10.2 g), and the mixture was stirred at room temperature under a pressurized hydrogen gas atmosphere (0.3 to 0.4 MPa) for 6 hours. The reaction mixture was filtered, and the filtrate was concentrated under reduced pressure. The residue was purified by silica gel column chromatography (chloroform/methanol) to yield the titled compounds, ethyl (1S,3S,4S,5R)-5-hydroxy-2-azabicyclo[2.2.2]octane-3-carboxylate (19.0 g) and ethyl (1S,3S,4R,6S)-6-hydroxy-2-azabicyclo[2.2.2]octane-3-carboxylate (5.05 g).

Ethyl (1S,3S,4S,5R)-5-hydroxy-2-azabicyclo[2.2.2]octane-3-carboxylate

LC-MS; [M+H]$^+$ 200.2/Rt (minutes) 0.27 (Analytical condition A)

Ethyl (1S,3S,4R,6S)-6-hydroxy-2-azabicyclo[2.2.2]octane-3-carboxylate

LC-MS; [M+H]$^+$ 200.1/Rt (minutes) 0.36 (Analytical condition A)

e) Preparation of (1S,3S,4S,5R)-2-(tert-butoxycarbonyl)-5-hydroxy-2-azabicyclo[2.2.2]octane-3-carboxylic Acid (Reference Example 5)

To a solution of ethyl (1S,3S,4S,5R)-5-hydroxy-2-azabicyclo[2.2.2]octane-3-carboxylate (10.48 g) in 1,4-dioxane (153 mL) was added 1 mol/L aqueous sodium hydroxide (238 mL), and the mixture was stirred at room temperature for an hour, cooled to 0° C. Di-tert-butyl dicarbonate (11.48 g) was added thereto. After stirring for an hour, 1 mol/L hydrochloric acid was added thereto to acidify the reaction mixture. Brine was added thereto, and the mixture was extracted with a mixed solvent of 10% ethanol/chloroform. The organic layer was dried over sodium sulfate. After filtration, the solvent was removed under reduced pressure. The residue was washed with diisopropyl ether, and the mixture was filtered out and dried to yield the titled compound (8.40 g).
$^1$H-NMR (DMSO-D$_6$) δ: 12.55 (1H, br s), 4.86 (1H, br s), 3.96-3.81 (3H, m), 2.09-1.69 (4H, m), 1.59-1.49 (1H, m), 1.36 (3H, s), 1.31 (6H, s), 1.29-1.17 (2H, m).

f) Preparation of (1S,3S,4R,6S)-2-(tert-butoxycarbonyl)-6-hydroxy-2-azabicyclo[2.2.2]octane-3-carboxylic Acid (Reference Example 6)

The titled compound (1.60 g) was prepared according to a similar procedure to step e) by using ethyl (1S,3S,4R,6S)-6-hydroxy-2-azabicyclo[2.2.2]octane-3-carboxylate (5.05 g).
$^1$H-NMR (DMSO-D$_6$) δ: 4.09-4.05 (3H, m), 2.28-2.20 (1H, m), 2.18-2.05 (2H, m), 1.91-1.80 (1H, m), 1.63-1.50 (3H, m), 1.45 (3H, s), 1.40 (6H, s).

Reference Example 7

(1S,3S,4S,5R)-2-(tert-Butoxycarbonyl)-5-hydroxy-2-azabicyclo[2.2.1]heptane-3-carboxylic Acid

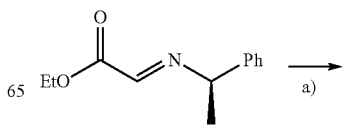

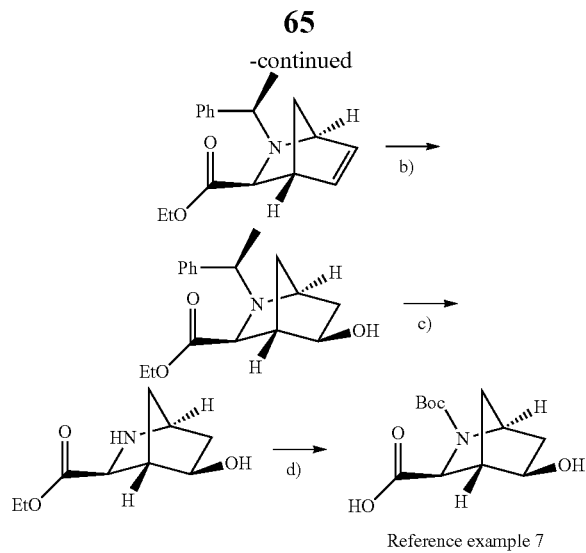

Reference example 7 a) Preparation of ethyl (1S,3S,4R)-2-[(1R)-1-phenylethyl]-2-azabicyclo[2.2.1]hept-5-ene-3-carboxylate The titled compound (10.8 g) was prepared according to a similar method to step b) of Reference example 5 by using ethyl (2E)-{[(1R)-1-phenylethyl]imino}acetate (12.0 g) and cyclopentadiene (4.92 mL).

LC-MS; [M+H]$^+$ 272.2/Rt (minutes) 0.54 (Analytical condition A)

b) Preparation of ethyl (1S,3S,4S,5R)-5-hydroxy-2-[(1R)-1-phenylethyl]-2-azabicyclo[2.2.1]heptane-3-carboxylate The titled compound (7.49 g) was prepared according to a similar method to step c) of Reference example 5 by using ethyl (1S,3S,4R)-2-[(1R)-1-phenylethyl]-2-azabicyclo[2.2.1]hept-5-ene-3-carboxylate (10.8 g).

LC-MS; [M+H]$^+$ 290.2/Rt (minutes) 0.46 (Analytical condition A)

c) Preparation of ethyl (1S,3S,4S,5R)-5-hydroxy-2-azabicyclo[2.2.1]heptane-3-carboxylate The titled compound (2.89 g) was obtained by a similar method to step d) of Reference example 5 by using ethyl (1S,3S,4S,5R)-5-hydroxy-2-[(1R)-1-phenylethyl]-2-azabicyclo[2.2.1]heptane-3-carboxylate (7.49 g).

LC-MS; [M+H]$^+$ 186.1/Rt (minutes) 0.27 (Analytical condition A)

d) Preparation of (1S,3S,4S,5R)-2-(tert-butoxycarbonyl)-5-hydroxy-2-azabicyclo[2.2.1]heptane-3-carboxylic Acid (Reference Example 7)

The titled compound (980 mg) was prepared according to a similar method to step e) of Reference example 5 by using ethyl (1S,3S,4S,5R)-5-hydroxy-2-azabicyclo[2.2.1]heptane-3-carboxylate (2.88 g).

$^1$H-NMR (DMSO-D$_6$) δ: 4.99 (1H, br s), 4.11-3.95 (1H, m), 3.95-3.82 (1H, m), 3.48-3.40 (1H, m), 2.41-2.31 (1H, m), 1.90-1.75 (1H, m), 1.69-1.49 (2H, m), 1.45-1.19 (10H, m).

Reference Example 8

3-Benzyl 2-tert-butyl (1S,3S,4S)-5-oxo-2-azabicyclo[2.2.2]octane-2,3-dicarboxylate

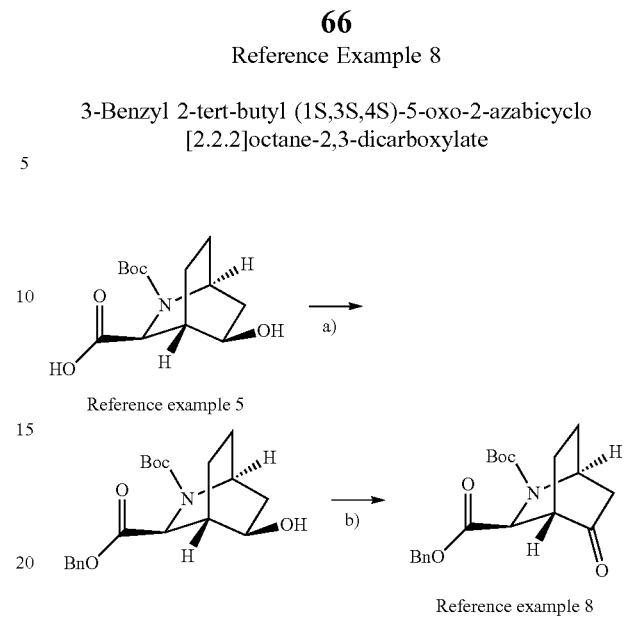

Reference example 8 a) Preparation of 3-benzyl 2-tert-butyl (1S,3S,4S,5R)-5-hydroxy-2-azabicyclo[2.2.2]octane-2,3-dicarboxylate To a solution of (1S,3S,4S,5R)-2-(tert-butoxycarbonyl)-5-hydroxy-2-azabicyclo[2.2.2]octane-3-carboxylic acid (28.0 g) and potassium carbonate (28.5 g) in acetonitrile (300 mL) was added benzyl bromide at room temperature, and the mixture was stirred overnight. The reaction mixture was concentrated under reduced pressure, and water was added to the residue. The mixture was extracted with ethyl acetate. The organic layer was dried over sodium sulfate and filtered, and the solvent was removed under reduced pressure. The residue was purified by silica gel column chromatography (hexane/ethyl acetate) to yield the titled compound (33.1 g).

LC-MS; [M+H]$^+$ 362.3/Rt (minutes) 0.95 (Analytical condition A)

b) Preparation of 3-benzyl 2-tert-butyl (1S,3S,4S)-5-oxo-2-azabicyclo[2.2.2]octane-2,3-dicarboxylate (Reference Example 8)

To a solution of 3-benzyl 2-tert-butyl (1S,3S,4S,5R)-5-hydroxy-2-azabicyclo[2.2.2]octane-2,3-dicarboxylate (33.0 g) in dichloromethane (400 mL) was added Dess-Martin reagent (46.5 g) at room temperature, and the mixture was stirred at room temperature overnight. To the reaction mixture was added aqueous sodium thiosulfate and aqueous sodium bicarbonate, and the mixture was extracted with chloroform. The organic layer was dried over sodium sulfate and filtered, and the solvent was removed under reduced pressure. The residue was purified by silica gel column chromatography (hexane/ethyl acetate) to yield a crude product (33.8 g) of the titled compound.

LC-MS; [M+H]$^+$ 360.2/Rt (minutes) 1.02 (Analytical condition A)

$^1$H-NMR (CDCl$_3$) δ: 7.38-7.28 (5H, m), 5.33-5.05 (2H, m), 4.66-4.42 (2H, m), 2.80-2.69 (1H, m), 2.59-2.45 (1H, m), 2.36-2.16 (2H, m), 1.82-1.62 (3H, m), 1.45 (2.5H, s), 1.31 (6.5H, s).

Reference Example 9

(1S,3S,4S)-2-(tert-Butoxycarbonyl)-5-oxo-2-azabicyclo[2.2.2]octane-3-carboxylic Acid

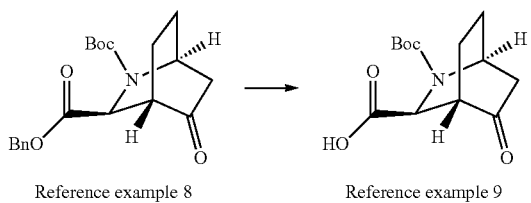 [SMILES: CC(C)(C)OC(=O)N1[C@H]2CC[C@H](C(=O)C2)[C@H]1C(=O)OCc1ccccc1 ; CC(C)(C)OC(=O)N1[C@H]2CC[C@H](C(=O)C2)[C@H]1C(=O)O]

Reference example 8 → Reference example 9

To a solution of 3-benzyl 2-tert-butyl (1S,3S,4S)-5-oxo-2-azabicyclo[2.2.2]octane-2,3-dicarboxylate (1.0 g) in methanol (30 mL) was added 5 mol/L aqueous sodium hydroxide (2.7 mL), and the mixture was stirred under heat at 50° C. for 5 hours. After the reaction mixture was cooled to room temperature, it was neutralized with 1 mol/L hydrochloric acid and extracted with chloroform. The organic layer was dried over sodium sulfate and filtered, and the solvent was removed under reduced pressure. The residue was purified by silica gel column chromatography (chloroform/methanol) to yield the titled compound (0.42 g).

LC-MS; [M+H]$^+$ 270.0/Rt (minutes) 0.59 (Analytical condition A)

Reference Example 10

(1S,3S,4R)-2-(tert-Butoxycarbonyl)-5-methylidene-2-azabicyclo[2.2.2]octane-3-carboxylic Acid

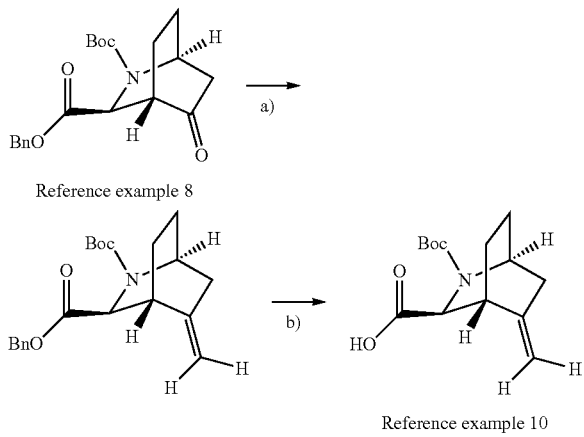

Reference example 10 a) Preparation of 3-benzyl 2-tert-butyl (1S,3S,4R)-5-methylidene-2-azabicyclo[2.2.2]octane-2,3-dicarboxylate To a solution of 3-benzyl 2-tert-butyl (1S,3S,4S)-5-oxo-2-azabicyclo[2.2.2]octane-2,3-dicarboxylate (3.0 g) in THF (30 mL) was added Petasis reagent (5% solution of THF/toluene, 35 g) at room temperature, and the mixture was stirred at 95° C. for 5 hours. The temperature was backed to room temperature, and Petasis reagent (5% solution of THF/toluene, 10 g) was added. The mixture was heated under reflux at 130° C. After cooling, diethyl ether was added thereto, a precipitated orange solid was filtered off, and the eluent was concentrated. The residue was purified by silica gel column chromatography (hexane/ethyl acetate) to yield the titled compound (1.9 g).

LC-MS; [M+H]$^+$ 358.0/Rt (minutes) 1.21 (Analytical condition A)

b) Preparation of (1S,3S,4R)-2-(tert-butoxycarbonyl)-5-methylidene-2-azabicyclo[2.2.2]octane-3-carboxylic Acid (Reference Example 10)

The titled compound (0.99 g) was prepared according to a similar method to Reference example 9 by using 3-benzyl 2-tert-butyl (1S,3S,4R)-5-methylidene-2-azabicyclo[2.2.2]octane-2,3-dicarboxylate (1.9 g).

LC-MS; [M+H]$^+$ 268.0/Rt (minutes) 0.83 (Analytical condition A)

Reference Example 11

(1S,3S,4R)-2-(tert-Butoxycarbonyl)-6-methylidene-2-azabicyclo[2.2.2]octane-3-carboxylic Acid

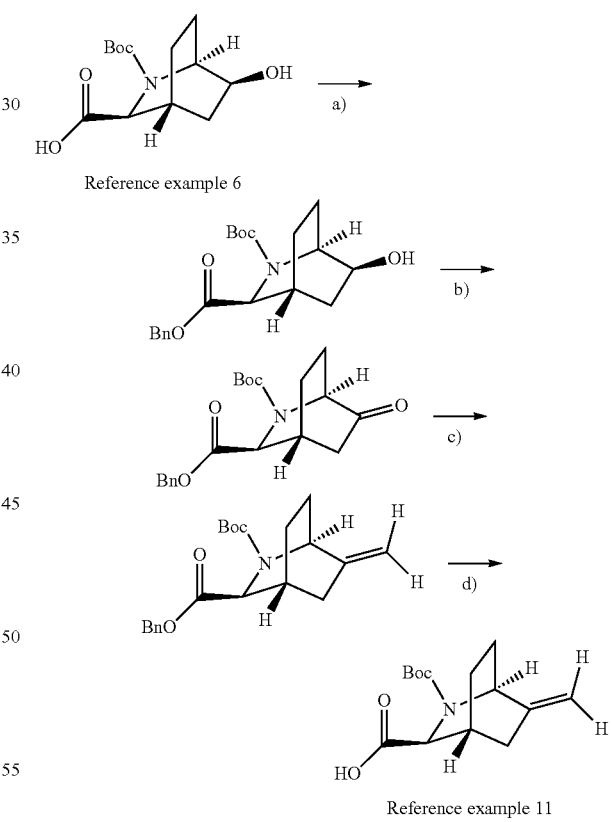

Reference example 11 a) Preparation of 3-benzyl 2-tert-butyl (1S,3S,4R,6S)-6-hydroxy-2-azabicyclo[2.2.2]octane-2,3-dicarboxylate The titled compound (65.5 g) was prepared according to a similar method to step a) of Reference example 8 by using (1S,3S,4R,6S)-2-(tert-butoxycarbonyl)-6-hydroxy-2-azabicyclo[2.2.2]octane-3-carboxylic acid (80.0 g).

LC-MS; [M+H]+ 362.1/Rt (minutes) 0.95 (Analytical condition A)

b) Preparation of 3-benzyl 2-tert-butyl (1S,3S,4R)-6-oxo-2-azabicyclo[2.2.2]octane-2,3-dicarboxylate The titled compound (6.0 g) was prepared according to a similar method to step b) of Reference example 8 by using 3-benzyl 2-tert-butyl (1S,3S,4R,6S)-6-hydroxy-2-azabicyclo[2.2.2]octane-2,3-dicarboxylate (10.0 g).
LC-MS; [M+H]+ 360.1/Rt (minutes) 1.02 (Analytical condition A)

c) Preparation of 3-benzyl 2-tert-butyl (1S,3S,4R)-6-methylidene-2-azabicyclo[2.2.2]octane-2,3-dicarboxylate The titled compound (2.12 g) was prepared according to a similar method to step a) of Reference example 10 by using 3-benzyl 2-tert-butyl (1S,3S,4R)-6-oxo-2-azabicyclo[2.2.2]octane-2,3-dicarboxylate (4.0 g).
LC-MS; [M+H]+ 358.0/Rt (minutes) 1.29 (Analytical condition A)

d) Preparation of (1S,3S,4R)-2-(tert-butoxycarbonyl)-6-methylidene-2-azabicyclo[2.2.2]octane-3-carboxylic Acid (Reference Example 11)

The titled compound (1.4 g) was prepared according to a similar method to Reference example 9 by using 3-benzyl 2-tert-butyl (1S,3S,4R)-6-methylidene-2-azabicyclo[2.2.2]octane-2,3-dicarboxylate (2.1 g).
LC-MS; [M+H]+ 268.0/Rt (minutes) 0.82 (Analytical condition A)

Reference Example 12

3-Benzyl 2-tert-butyl (1S,3S,4S)-5-oxo-2-azabicyclo[2.2.1]heptane-2,3-dicarboxylate

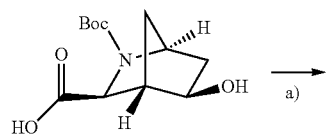

Reference example 7

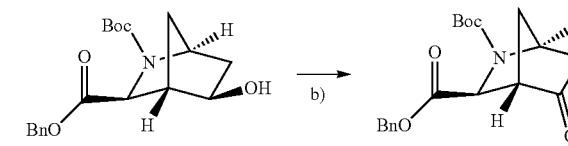

Reference example 12 a) Preparation of 3-benzyl 2-tert-butyl (1S,3S,4S,5R)-5-hydroxy-2-azabicyclo[2.2.1]heptane-2,3-dicarboxylate The titled compound (1.73 g) was prepared according to a similar method to step a) of Reference example 8 by using (1S,3S,4S,5R)-2-(tert-butoxycarbonyl)-5-hydroxy-2-azabicyclo[2.2.1]heptane-3-carboxylic acid (1.5 g).

LC-MS; [M+H]+ 348.2/Rt (minutes) 0.92 (Analytical condition A)

b) Preparation of 3-benzyl 2-tert-butyl (1S,3S,4S)-5-oxo-2-azabicyclo[2.2.1]heptane-2,3-dicarboxylate (Reference Example 12)

The titled compound (1.40 g) was obtained according to a similar method to step b) of Reference example 8 by using 3-benzyl 2-tert-butyl (1S,3S,4S,5R)-5-hydroxy-2-azabicyclo[2.2.1]heptane-2,3-dicarboxylate (1.73 g).
LC-MS; [M+H]+ 346.2/Rt (minutes) 1.01 (Analytical condition A)

Reference Example 13

(1S,3S,4R)-2-(tert-Butoxycarbonyl)-5-methylidene-2-azabicyclo[2.2.1]heptane-3-carboxylic Acid

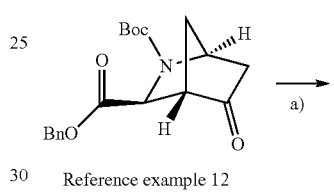

Reference example 12

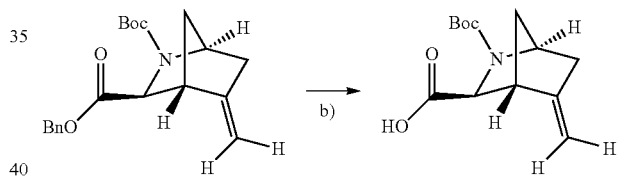

Reference example 13 a) Preparation of 3-benzyl 2-tert-butyl (1S,3S,4R)-5-methylidene-2-azabicyclo[2.2.1]heptane-2,3-dicarboxylate The titled compound (1.10 g) was prepared according to a similar method to step a) of Reference example 10 by using 3-benzyl 2-tert-butyl (1S,3S,4S)-5-oxo-2-azabicyclo[2.2.1]heptane-2,3-dicarboxylate (1.40 g).
LC-MS; [M+H]+ 344.2/Rt (minutes) 1.18 (Analytical condition A)

b) Preparation of (1S,3S,4R)-2-(tert-butoxycarbonyl)-5-methylidene-2-azabicyclo[2.2.1]heptane-3-carboxylic Acid (Reference Example 13)

The titled compound (0.69 g) was prepared according to a similar method to Reference example 9 by using 3-benzyl 2-tert-butyl (1S,3S,4R)-5-methylidene-2-azabicyclo[2.2.1]heptane-2,3-dicarboxylate (1.10 g).
LC-MS; [M+H]+ 254.3/Rt (minutes) 0.82 (Analytical condition A)

Reference Example 14

3-Benzyl 2-tert-butyl (1S,3S,4S,6E)-6-(cyclopropyl-methylidene)-5-oxo-2-azabicyclo[2.2.2]octane-2,3-dicarboxylate

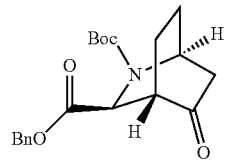

Reference example 8

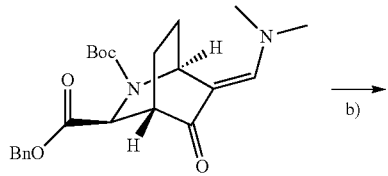

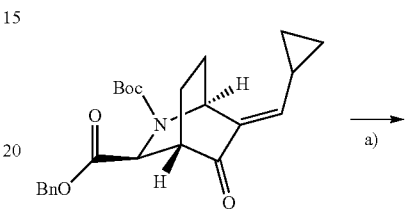

Reference example 14 a) Preparation of 3-benzyl 2-tert-butyl (1S,3S,4S, 6E)-6-[(dimethylamino)methylidene]-5-oxo-2-azabi-cyclo[2.2.2]octane-2,3-dicarboxylate To a solution of 3-benzyl 2-tert-butyl (1S,3S,4S)-5-oxo-2-azabicyclo[2.2.2]octane-2,3-dicarboxylate (33.8 g) in N,N-dimethylformamide (180 mL) was added Bredereck reagent (32.8 g), and the mixture was stirred with heating at 100° C. for 2 hours. The reaction mixture was concentrated under reduced pressure, and the residue was purified by silica gel column chromatography (hexane/ethyl acetate) to yield a crude product of the titled compound (39.0 g).

LC-MS; [M+H]$^+$ 415.4/Rt (minutes) 0.95 (Analytical condition A)

b) Preparation of 3-benzyl 2-tert-butyl (1S,3S,4S, 6E)-6-(cyclopropylmethylidene)-5-oxo-2-azabicyclo [2.2.2]octane-2,3-dicarboxylate (Reference Example 14)

A solution of 3-benzyl 2-tert-butyl (1S,3S,4S,6E)-6-[(dimethylamino)methylidene]-5-oxo-2-azabicyclo[2.2.2]oc-tane-2,3-dicarboxylate (39.0 g) in tetrahydrofuran (300 mL) was cooled to 0° C., and cyclopropylmagnesium bromide (0.5 mol/L aqueous tetrahydrofuran, 245 mL) was added dropwise thereto. The mixture was stirred at room temperature for 6 hours. To the reaction mixture was added saturated aqueous ammonium chloride, and the mixture was extracted with ethyl acetate. The organic layer was dried over sodium sulfate and filtered, and the solvent was removed under reduced pressure. The residue was purified by silica gel column chromatography (hexane/ethyl acetate) to yield the titled compound (32.3 g).

LC-MS; [M+H]$^+$ 412.4/Rt (minutes) 1.16 (Analytical condition A)

$^1$H-NMR (CDCl$_3$) δ: 7.39-7.27 (5H, m), 5.91 (1H, t, J=11.0 Hz), 5.38-5.04 (3H, m), 4.50-4.36 (1H, m), 2.90-2.76 (1H, m), 2.37-2.22 (1H, m), 1.82-1.59 (4H, m), 1.44 (3H, s), 1.31 (6H, s), 1.09-0.95 (2H, m), 0.73-0.58 (2H, m).

Reference Example 15

3-Benzyl 2-tert-butyl (1S,3S,4S)-6-(cyclopropylm-ethyl)-5-hydroxy-2-azabicyclo[2.2.2]octane-2,3-dicarboxylate

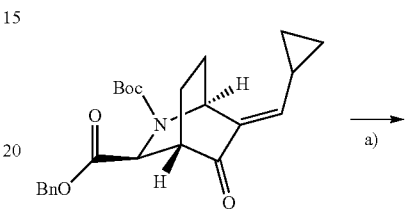

Reference example 14

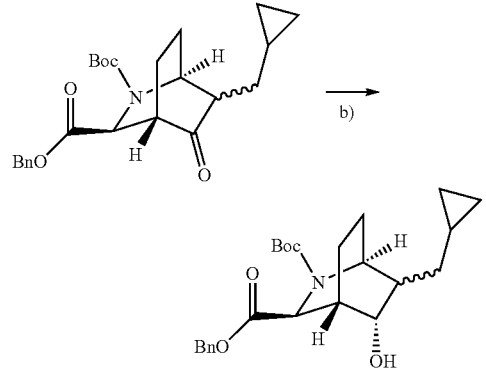

Reference example 15
Low polarity

+

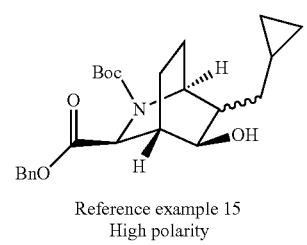

Reference example 15
High polarity a) Preparation of 3-benzyl 2-tert-butyl (1S,3S,4S)-6-(cyclopropylmethyl)-5-oxo-2-azabicyclo[2.2.2] octane-2,3-dicarboxylate To a solution of 3-benzyl 2-tert-butyl (1S,3S,4S,6E)-6-(cyclopropylmethylidene)-5-oxo-2-azabicyclo[2.2.2]oc-tane-2,3-dicarboxylate (32.3 g) in tetrahydrofuran (300 mL) was added copper(I) hydride triphenylphosphine hexamer (38.5 g), and the mixture was stirred at room temperature for 12 hours. The reaction mixture was filtered through Celite, and the filtrate was concentrated under reduced pressure. The residue was purified by silica gel column chromatography (hexane/ethyl acetate) to yield the titled compound (23.2 g) as a mixture of stereoisomers.

LC-MS; [M+H]⁺ 414.1/Rt (minutes) 1.22 (Analytical condition A)

b) Preparation of 3-benzyl 2-tert-butyl (1S,3S,4S)-6-(cyclopropylmethyl)-5-hydroxy-2-azabicyclo[2.2.2]octane-2,3-dicarboxylate (Reference Example 15)

A solution of 3-benzyl 2-tert-butyl (1S,3S,4S)-6-(cyclopropylmethyl)-5-oxo-2-azabicyclo[2.2.2]octane-2,3-dicarboxylate (23.2 g) in methanol (200 mL) was cooled to 0° C., sodium borohydride (2.12 g) was added thereto, and the mixture was stirred for an hour. The reaction mixture was concentrated under reduced pressure, and the residue was purified by silica gel column chromatography (hexane/ethyl acetate) to yield the titled compound as a stereoisomer mixture in low polarity (9.3 g) and a stereoisomer mixture in high polarity (10.2 g).

The stereoisomer mixture in low polarity: 3-benzyl 2-tert-butyl (1S,3S,4S,5S)-6-(cyclopropylmethyl)-5-hydroxy-2-azabicyclo[2.2.2]octane-2,3-dicarboxylate
LC-MS; [M+H]⁺ 416.1/Rt (minutes) 1.13 (Analytical condition A)

The stereoisomer mixture in high polarity: 3-benzyl 2-tert-butyl (1S,3S,4S,5R)-6-(cyclopropylmethyl)-5-hydroxy-2-azabicyclo[2.2.2]octane-2,3-dicarboxylate
LC-MS; [M+H]⁺ 416.1/Rt (minutes) 1.01 (Analytical condition A)

Reference Example 16

(1S,3S,4S,5R,6R)-2-(tert-Butoxycarbonyl)-6-(cyclopropylmethyl)-5-fluoro-2-azabicyclo[2.2.2]octane-3-carboxylic Acid Reference Example 17

(1S,3S,4S,5R,6S)-2-(tert-Butoxycarbonyl)-6-(cyclopropylmethyl)-5-fluoro-2-azabicyclo[2.2.2]octane-3-carboxylic Acid Reference Example 18

(1S,3S,4S,5S,6R)-2-(tert-Butoxycarbonyl)-6-(cyclopropylmethyl)-5-fluoro-2-azabicyclo[2.2.2]octane-3-carboxylic Acid Reference Example 19

(1S,3S,4S,5S,6S)-2-(tert-Butoxycarbonyl)-6-(cyclopropylmethyl)-5-fluoro-2-azabicyclo[2.2.2]octane-3-carboxylic Acid

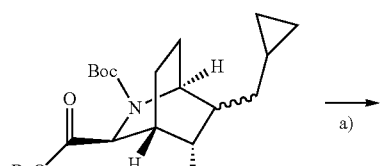

Reference example 15
Low polarity

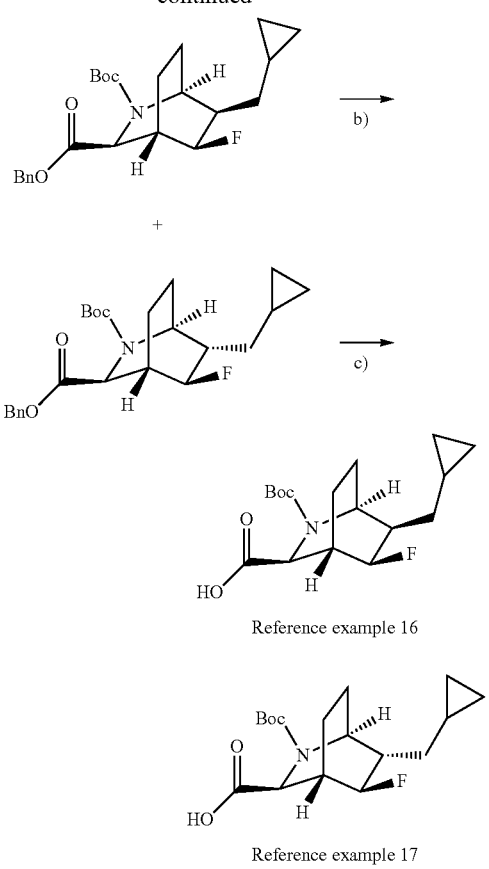

Reference example 16

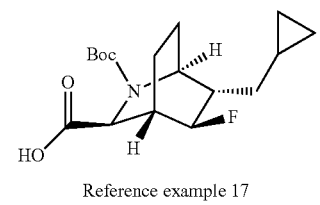

Reference example 17

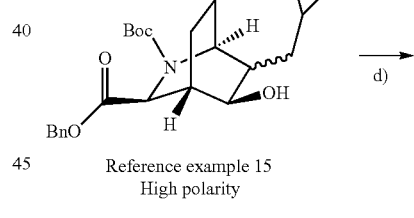

Reference example 15
High polarity

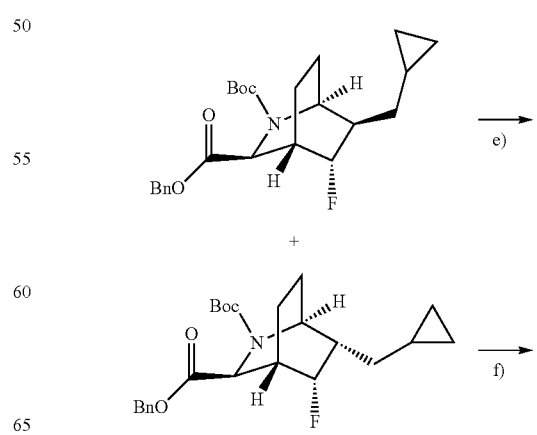

-continued

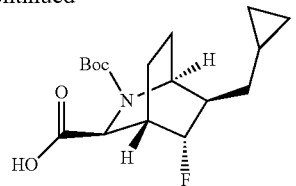

Reference example 18

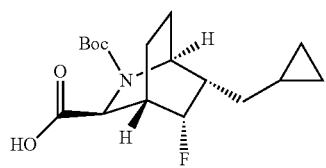

Reference example 19 a) Preparation of 3-benzyl 2-tert-butyl (1S,3S,4S, 5R,6R)-6-(cyclopropylmethyl)-5-fluoro-2-azabicyclo[2.2.2]octane-2,3-dicarboxylate and 3-benzyl 2-tert-butyl (1S,3S,4S,5R,6S)-6-(cyclopropylmethyl)-5-fluoro-2-azabicyclo[2.2.2]octane-2,3-dicarboxylate A solution of 3-benzyl 2-tert-butyl (1S,3S,4S,5S)-6-(cyclopropylmethyl)-5-hydroxy-2-azabicyclo[2.2.2]octane-2,3-dicarboxylate (9.3 g) which is the stereoisomer mixture in high polarity in Reference example 15, in dichloromethane (80 mL) was cooled to 0° C., and diethylaminosulfur trifluoride (5.91 mL) was added thereto. The mixture was stirred at room temperature overnight. To the reaction mixture was added saturated aqueous sodium bicarbonate, and the mixture was extracted with chloroform. The organic layer was dried over sodium sulfate and filtered, and the solvent was removed under reduced pressure. The residue was purified by silica gel column chromatography (hexane/ ethyl acetate) to yield 3-benzyl 2-tert-butyl (1S,3S,4S,5R, 6R)-6-(cyclopropylmethyl)-5-fluoro-2-azabicyclo[2.2.2]octane-2,3-dicarboxylate (3.6 g) and 3-benzyl 2-tert-butyl (1S, 3S,4S,5R,6S)-6-(cyclopropylmethyl)-5-fluoro-2-azabicyclo [2.2.2]octane-2,3-dicarboxylate (3.7 g).

3-Benzyl 2-tert-butyl (1S,3S,4S,5R,6R)-6-(cyclopropylmethyl)-5-fluoro-2-azabicyclo[2.2.2]octane-2, 3-dicarboxylate LC-MS; [M+H]+ 418.4/Rt (minutes) 1.29 (Analytical condition A)

3-Benzyl 2-tert-butyl (1S,3S,4S,5R,6S)-6-(cyclopropylmethyl)-5-fluoro-2-azabicyclo[2.2.2]octane-2,3-dicarboxylate LC-MS; [M+H]+ 418.4/Rt (minutes) 1.35 (Analytical condition A)

b) Preparation of (1S,3S,4S,5R,6R)-2-(tert-butoxycarbonyl)-6-(cyclopropylmethyl)-5-fluoro-2-azabicyclo[2.2.2]octane-3-carboxylic Acid (Reference Example 16)

To a solution of 3-benzyl 2-tert-butyl (1S,3S,4S,5R,6R)-6-(cyclopropylmethyl)-5-fluoro-2-azabicyclo[2.2.2]octane-2,3-dicarboxylate (3.6 g) and ammonium formate (5.4 g) in tetrahydrofuran (50 mL) was added palladium hydroxide/ carbon (1.2 g), and the mixture was heated under reflux for 3 hours. The reaction mixture was cooled to room temperature, filtered through Celite, and the filtrate was concentrated under reduced pressure to yield the titled compound (2.8 g).

LC-MS; [M−H]− 326.4/Rt (minutes) 0.95 (Analytical condition A)

c) Preparation of (1S,3S,4S,5R,6S)-2-(tert-butoxycarbonyl)-6-(cyclopropylmethyl)-5-fluoro-2-azabicyclo[2.2.2]octane-3-carboxylic Acid (Reference Example 17)

A crude product (108 mg) of the titled compound was prepared according to a similar method to step b) of Reference example 16 by using 3-benzyl 2-tert-butyl (1S,3S,4S, 5R,6S)-6-(cyclopropylmethyl)-5-fluoro-2-azabicyclo[2.2.2] octane-2,3-dicarboxylate (108 mg).

LC-MS; [M−H]− 326.4/Rt (minutes) 0.95 (Analytical condition A)

d) Preparation of 3-benzyl 2-tert-butyl (1S,3S,4S, 5S,6R)-6-(cyclopropylmethyl)-5-fluoro-2-azabicyclo [2.2.2]octane-2,3-dicarboxylate and 3-benzyl 2-tertbutyl (1S,3S,4S,5S,6S)-6-(cyclopropylmethyl)-5-fluoro-2-azabicyclo[2.2.2]octane-2,3-dicarboxylate 3-Benzyl 2-tert-butyl (1S,3S,4S,5S,6R)-6-(cyclopropylmethyl)-5-fluoro-2-azabicyclo[2.2.2]octane-2,3-dicarboxylate (86 mg) and 3-benzyl 2-tert-butyl (1S,3S,4S,5S,6S)-6-(cyclopropylmethyl)-5-fluoro-2-azabicyclo[2.2.2]octane-2, 3-dicarboxylate (152 mg) were prepared according to a similar method to step a) of Reference example 16 by using 3-benzyl 2-tert-butyl (1S,3S,4S,5R)-6-(cyclopropylmethyl)-5-hydroxy-2-azabicyclo[2.2.2]octane-2,3-dicarboxylate (363 mg), which is the stereoisomer mixture in high polarity in Reference example 15.

3-Benzyl 2-tert-butyl (1S,3S,4S,5S,6R)-6-(cyclopropylmethyl)-5-fluoro-2-azabicyclo[2.2.2]octane-2,3-dicarboxylate LC-MS; [M+H]+ 418.4/Rt (minutes) 1.27 (Analytical condition A)

3-Benzyl 2-tert-butyl (1S,3S,4S,5S,6S)-6-(cyclopropylmethyl)-5-fluoro-2-azabicyclo[2.2.2]octane-2,3-dicarboxylate LC-MS; [M+H]+ 418.4/Rt (minutes) 1.29 (Analytical condition A)

e) Preparation of (1S,3S,4S,5S,6R)-2-(tert-butoxycarbonyl)-6-(cyclopropylmethyl)-5-fluoro-2-azabicyclo[2.2.2]octane-3-carboxylic Acid (Reference Example 18)

A crude product (73 mg) of the titled compound was prepared according to a similar method to step b) of Reference example 16 by using 3-benzyl 2-tert-butyl (1S,3S,4S, 5S,6R)-6-(cyclopropylmethyl)-5-fluoro-2-azabicyclo[2.2.2] octane-2,3-dicarboxylate (82 mg).

LC-MS; [M−H]− 326.4/Rt (minutes) 0.94 (Analytical condition A)

f) Preparation of (1S,3S,4S,5S,6S)-2-(tert-butoxycarbonyl)-6-(cyclopropylmethyl)-5-fluoro-2-azabicyclo[2.2.2]octane-3-carboxylic Acid (Reference Example 19)

A crude product (140 mg) of the titled compound was prepared according to a similar method to step b) of Reference example 16 by using 3-benzyl 2-tert-butyl (1S,3S,4S,5S,6S)-6-(cyclopropylmethyl)-5-fluoro-2-azabicyclo[2.2.2]octane-2,3-dicarboxylate (147 mg).

LC-MS; [M−H]⁻ 326.3/Rt (minutes) 0.95 (Analytical condition A)

Reference Example 20

(1S,3S,4R,6S)-2-(tert-Butoxycarbonyl)-6-(cyclopropylmethyl)-2-azabicyclo[2.2.2]octane-3-carboxylic Acid Reference Example 21

(1S,3S,4R,6R)-2-(tert-Butoxycarbonyl)-6-(cyclopropylmethyl)-2-azabicyclo[2.2.2]octane-3-carboxylic Acid

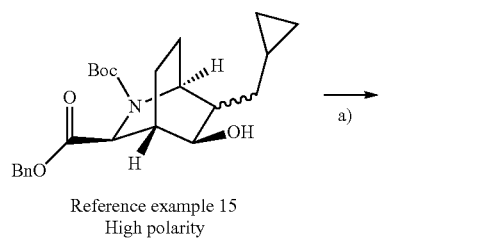

Reference example 15
High polarity

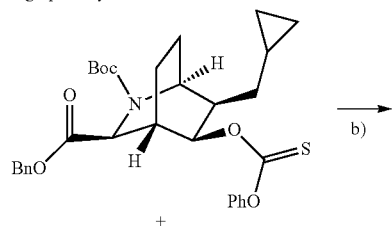

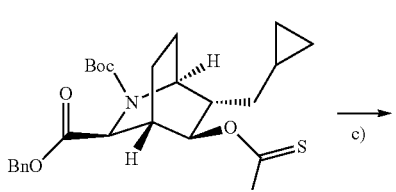

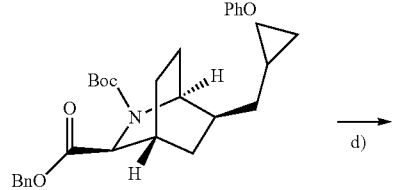

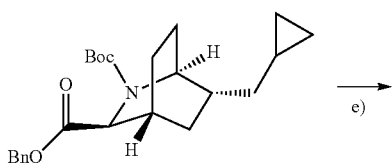

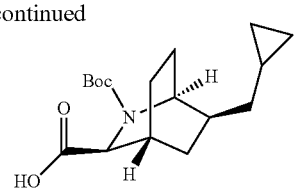

Reference example 20

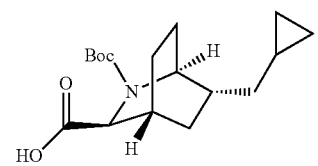

Reference example 21 a) Preparation of 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate and 3-benzyl 2-tert-butyl (1S,3S,4S,5R,6S)-6-(cyclopropylmethyl)-5-[(phenoxycarbonothioyl)oxy]-2-azabicyclo[2.2.2]octane-2,3-dicarboxylate A solution of 3-benzyl 2-tert-butyl (1S,3S,4S,5R)-6-(cyclopropylmethyl)-5-hydroxy-2-azabicyclo[2.2.2]octane-2,3-dicarboxylate (7.3 g) which is the stereoisomer mixture in high polarity in Reference example 15, in acetonitrile (50 mL) was cooled to 0° C., and 4-(dimethylamino)pyridine (8.6 g) and phenyl chlorothionoformate (4.74 mL) were added thereto. The mixture was stirred at 50° C. for 12 hours. The reaction mixture was cooled to room temperature, brine was added thereto, and the mixture was extracted with ethyl acetate. The organic layer was dried over magnesium sulfate and filtered, and the solvent was removed under reduced pressure. The residue was purified by silica gel column chromatography (hexane/ethyl acetate) to yield a crude product (1.80 g) of 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate, and a crude product (7.90 g) of 3-benzyl 2-tert-butyl (1S,3S,4S,5R,6S)-6-(cyclopropylmethyl)-5-[(phenoxycarbonothioyl)oxy]-2-azabicyclo[2.2.2]octane-2,3-dicarboxylate.

3-Benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate LC-MS; [M+H]⁺ 552.2/Rt (minutes) 1.42 (Analytical condition A)

3-Benzyl 2-tert-butyl (1S,3S,4S,5R,6S)-6-(cyclopropylmethyl)-5-[(phenoxycarbonothioyl)oxy]-2-azabicyclo[2.2.2]octane-2,3-dicarboxylate LC-MS; [M+H]⁺ 552.2/Rt (minutes) 1.45 (Analytical condition A)

b) Preparation of 3-benzyl 2-tert-butyl (1S,3S,4R,6S)-6-(cyclopropylmethyl)-2-azabicyclo[2.2.2]octane-2,3-dicarboxylate A solution of 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate (1.80 g) in toluene (50 mL) was cooled to 0° C., and tris(trimethylsilyl)

silane (5.03 mL) and 2,2′-azobis(2-methylpropionitrile) (0.11 g) were added thereto. The mixture was stirred with heating at 50° C. for 5 hours. The reaction mixture was cooled to room temperature, brine was added thereto, and the mixture was extracted with ethyl acetate. The organic layer was dried over magnesium sulfate and filtered, and the solvent was removed under reduced pressure. The residue was purified by silica gel column chromatography (hexane/ethyl acetate) to yield the titled compound (0.80 g).

LC-MS; [M+H]+ 400.2/Rt (minutes) 1.38 (Analytical condition A)

c) Preparation of 3-benzyl 2-tert-butyl (1S,3S,4R,6R)-6-(cyclopropylmethyl)-2-azabicyclo[2.2.2]octane-2,3-dicarboxylate The titled compound (5.50 g) was prepared according to a similar method to step b) of Reference example 20 by using 3-benzyl 2-tert-butyl (1S,3S,4S,5R,6S)-6-(cyclopropylmethyl)-5-[(phenoxycarbonothioyl)oxy]-2-azabicyclo[2.2.2]octane-2,3-dicarboxylate (7.90 g).

LC-MS; [M+H]+ 400.2/Rt (minutes) 1.40 (Analytical condition A)

d) Preparation of (1S,3S,4R,6S)-2-(tert-butoxycarbonyl)-6-(cyclopropylmethyl)-2-azabicyclo[2.2.2]octane-3-carboxylic Acid (Reference Example 20)

The titled compound (3.90 g) was prepared according to a similar method to step b) of Reference example 16 by using 3-benzyl 2-tert-butyl (1S,3S,4R,6S)-6-(cyclopropylmethyl)-2-azabicyclo[2.2.2]octane-2,3-dicarboxylate (5.50 g).

LC-MS; [M+H]+ 310.2/Rt (minutes) 1.02 (Analytical condition A)

e) Preparation of (1S,3S,4R,6R)-2-(tert-butoxycarbonyl)-6-(cyclopropylmethyl)-2-azabicyclo[2.2.2]octane-3-carboxylic Acid (Reference Example 21)

The titled compound (980 mg) was prepared according to a similar method to step b) of Reference example 16 by using 3-benzyl 2-tert-butyl (1S,3S,4R,6R)-6-(cyclopropylmethyl)-2-azabicyclo[2.2.2]octane-2,3-dicarboxylate (1.20 g).

LC-MS; [M+H]+ 310.2/Rt (minutes) 1.04 (Analytical condition A)

Reference Example 22 tert-Butyl (1S,3S,4S)-3-[2-(5-{2-[di(propan-2-yl)carbamoyl]-4-fluorophenoxy}pyrimidin-4-yl)-2,7-diazaspiro[3.5]nonane-7-carbonyl]-5-oxo-2-azabicyclo[2.2.2]octane-2-carboxylate

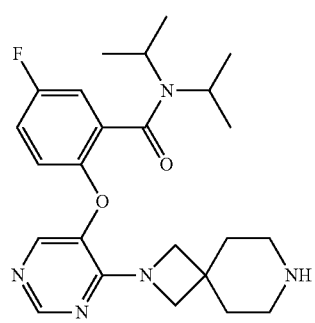

Reference example 2

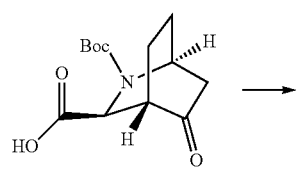

Reference example 9

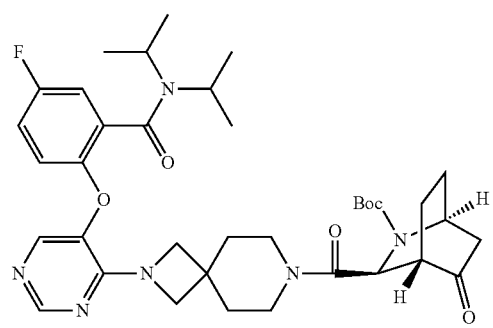

Reference example 22

To a solution of 2-{[4-(2,7-diazaspiro[3.5]nonan-2-yl)pyrimidin-5-yl]oxy}-5-fluoro-N,N-di(propan-2-yl)benzamide (164 mg) obtained in Reference example 2 in chloroform (2 mL) were added (1S,3S,4S)-2-(tert-butoxycarbonyl)-5-oxo-2-azabicyclo[2.2.2]octane-3-carboxylic acid (100 mg) obtained in Reference example 9, WSCI.HCl (85 mg), HOBt (68 mg), and N,N-diisopropylethylamine (0.13 mL), and the mixture was stirred at room temperature for 2 hours. To the reaction mixture was added water, and the mixture was extracted with chloroform. The resulting organic layer was dried over sodium sulfate and filtered, and the solvent was removed under reduced pressure. The residue was purified by silica gel column chromatography (hexane/ethyl acetate) to yield the titled compound (245 mg).

LC-MS; [M+H]+ 693.2/Rt (minutes) 0.97 (Analytical condition A)

Reference Example 23 tert-Butyl (1S,3S,4S)-3-[2-(5-{2-[di(propan-2-yl)carbamoyl]-4-fluorophenoxy}pyrimidin-4-yl)-2,7-diazaspiro[3.5]nonane-7-carbonyl]-5-(methoxyimino)-2-azabicyclo[2.2.2]octane-2-carboxylate

Reference Example 24 tert-Butyl (1R,3S,4R)-3-[7-(5-{2-[di(propan-2-yl)carbamoyl]-4-fluorophenoxy}pyrimidin-4-yl)-2,7-diazaspiro[4.4]nonane-2-carbonyl]-2-azabicyclo[2.2.2]octane-2-carboxylate

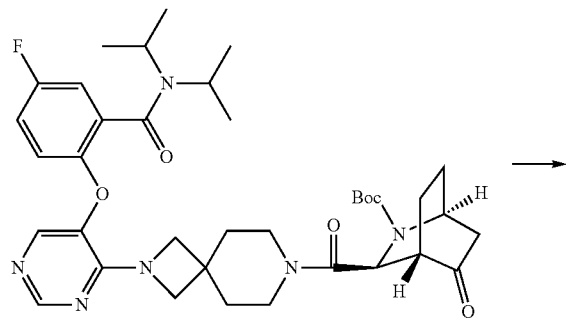

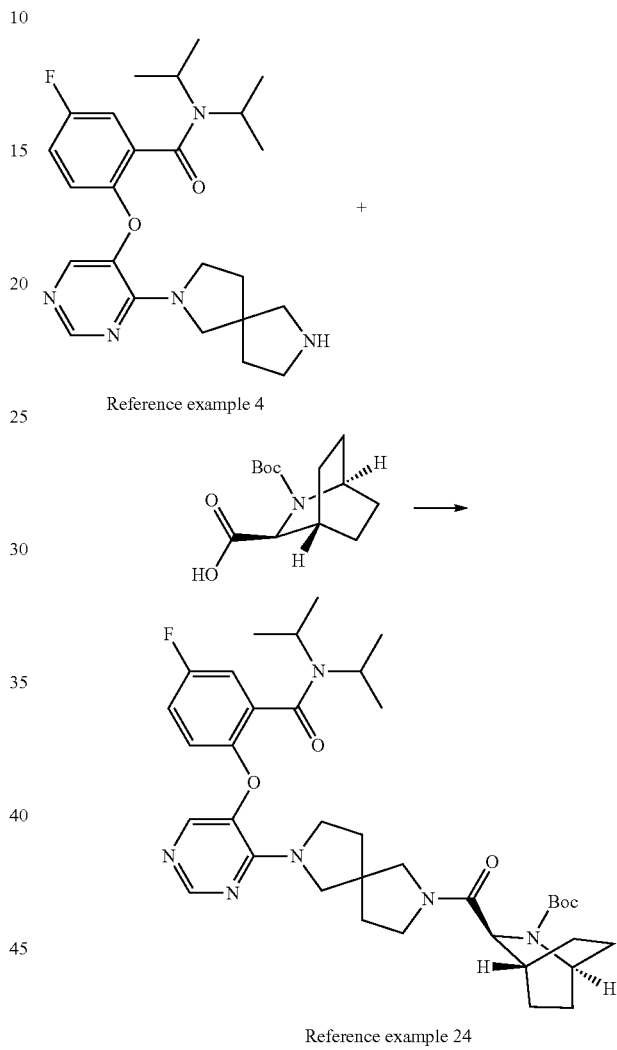

To a solution of tert-butyl (1S,3S,4S)-3-[2-(5-{2-[di(propan-2-yl)carbamoyl]-4-fluorophenoxy}pyrimidin-4-yl)-2,7-diazaspiro[3.5]nonane-7-carbonyl]-5-oxo-2-azabicyclo[2.2.2]octane-2-carboxylate (100 mg) obtained in Reference example 22 in ethanol (1 mL) and water (2 mL) were added O-methylhydroxylamine hydrochloride (24 mg) and sodium acetate (35 mg), and the mixture was stirred at 75° C. for 3 hours. To the reaction mixture was added water, and the mixture was extracted with ethyl acetate. The resulting organic layer was dried over sodium sulfate and filtered, and the solvent was removed under reduced pressure to yield the titled compound (89 mg).

LC-MS; [M+H]$^+$ 722.6/Rt (minutes) 0.98 (Analytical condition A)

The titled compound (100 mg) was prepared according to a similar method to Reference example 22 by using 2-{[4-(2,7-diazaspiro[4.4]nonan-2-yl)pyrimidin-5-yl]oxy}-5-fluoro-N,N-di(propan-2-yl)benzamide (122 mg) obtained in Reference example 4 and (1S,3S,4R)-2-(tert-butoxycarbonyl)-2-azabicyclo[2.2.2]octane-3-carboxylic acid (85 mg) which is commercially available.

LC-MS; [M+H]$^+$ 679.0/Rt (minutes) 1.89 (Analytical condition B)

Reference Example 25 to 40

The following Reference examples 25 to 40 were prepared according to similar methods to Reference example 22 by using each corresponding starting compound.

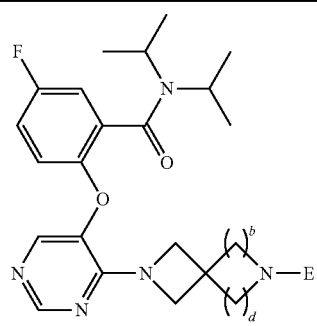

| Ref. Example | b | d | E | LC-MS; [M + H]+/Rt (min) (Analytical condition) |
|---|---|---|---|---|
| 25 | 2 | 2 | (Boc-piperidine with cyclopropylmethyl, wedge up) | 733.4/2.07 (Analytical condition B) |
| 26 | 1 | 1 | (Boc-piperidine with cyclopropylmethyl, wedge up) | 705.3/1.11 (Analytical condition A) |
| 27 | 2 | 2 | (Boc-piperidine with cyclopropylmethyl, wedge down) | 733.2/1.19 (Analytical condition A) |
| 28 | 1 | 1 | (Boc-piperidine with cyclopropylmethyl, wedge down) | 705.2/1.11 (Analytical condition A) |
| 29 | 2 | 2 | (Boc-piperidine with exo-methylene) | 691.2/1.18 (Analytical condition A) |
| 30 | 1 | 1 | (Boc-piperidine with exo-methylene) | 663.2/1.03 (Analytical condition A) |
| 31 | 2 | 2 | (Boc-piperidine with exo-methylene) | 691.3/1.02 (Analytical condition A) |

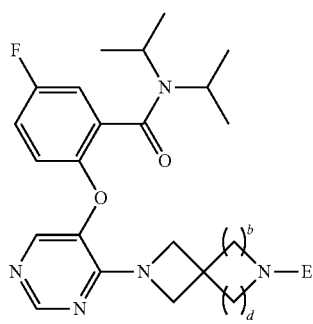
| Ref. Example | b | d | E | LC-MS; [M + H]+/Rt (min) (Analytical condition) |
|---|---|---|---|---|
| 32 | 1 | 1 | | 663.3/1.04 (Analytical condition A) |
| 33 | 1 | 1 | | 669.4/1.09 (Analytical condition A) |
| 34 | 1 | 1 | | 651.3/1.00 (Analytical condition A) |
| 35 | 2 | 2 | | 751.3/1.45 (Analytical condition A) |
| 36 | 1 | 1 | | 637.2/1.15 (Analytical condition A) |
| 37 | 2 | 2 | | 665.3/1.15 (Analytical condition A) |
| 38 | 2 | 2 | | 695.3/0.92 (Analytical condition A) |
| 39 | 2 | 2 | | 677.2/1.63 (Analytical condition B) |
| 40 | 2 | 2 | | 751.4/2.06 (Analytical condition B) |

Reference Example 41 tert-Butyl (1S,3S,4R)-3-[2-(5-{2-[di(propan-2-yl)carbamoyl]-4-fluorophenoxy}pyrimidin-4-yl)-2,7-diazaspiro[3.5]nonane-7-carbonyl]-5-($^2$H$_2$)methylidene-2-azabicyclo[2.2.2]octane-2-carboxylate

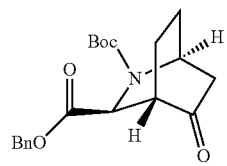

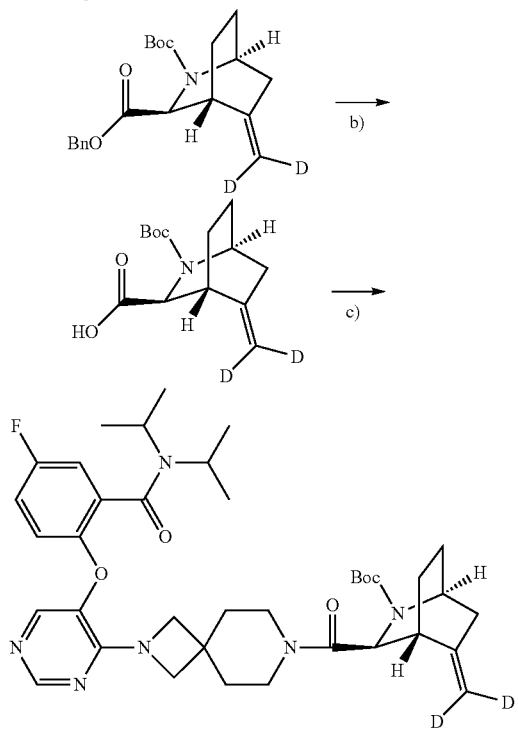

Reference example 41 a) Preparation of 3-benzyl 2-tert-butyl (1S,3S,4R)-5-($^2$H$_2$)methylidene-2-azabicyclo[2.2.2]octane-2,3-dicarboxylate To a suspension of ($^2$H$_3$)methyl(triphenyl)phosphonium iodide (2.83 g) in THF (14 mL) was added dropwise n-butyllithium (1.57 mol/L hexane solution, 3.54 mL), and the mixture was stirred at 0° C. for 1.5 hours. The reaction was cooled again to −78° C., and 3-benzyl 2-tert-butyl (1S,3S,4S)-5-oxo-2-azabicyclo[2.2.2]octane-2,3-dicarboxylate (1.0 g) was added portionwise. The mixture was stirred for 5 hours. The reaction was backed to room temperature, quenched by addition of saturated aqueous ammonium chloride, and the mixture was extracted with ethyl acetate. The resulting organic layer was washed with water and brine, dried over anhydrous sodium sulfate, and filtered. The solvent was removed under reduced pressure. The residue was purified by silica gel column chromatography (hexane/ethyl acetate) to yield the titled compound (0.46 g).

LC-MS; [M+H]$^+$ 360.4/Rt (minutes) 1.22 (Analytical condition A)

b) Preparation of (1S,3S,4R)-2-(tert-butoxycarbonyl)-5-($^2$H$_2$)methylidene-2-azabicyclo[2.2.2]octane-3-carboxylic Acid To a solution of 3-benzyl 2-tert-butyl (1S,3S,4R)-5-($^2$H$_2$)methylidene-2-azabicyclo[2.2.2]octane-2,3-dicarboxylate in methanol (10 mL) were added aqueous sodium hydroxide (5 mol/L, 1.8 mL) and water (2 mL), and the mixture was stirred at 50° C. for 4 hours. The reaction mixture was cooled to room temperature, and the methanol was removed under reduced pressure. The resulting solution was extracted with chloroform. The aqueous layer was acidified with 1 mol/L hydrochloric acid, and extracted with chloroform. The organic layer was washed with brine, dried over anhydrous sodium sulfate, and filtered. The solvent was removed under reduced pressure to yield the titled compound (0.31 g). The resulting compound was used in the next reaction without purification.

LC-MS; [M+H]$^+$ 270.2/Rt (minutes) 0.89 (Analytical condition A) $^1$H-NMR (DMSO-D$_6$) δ: 12.60 (1H, br s), 4.17-3.95. (total 2H, m), 2.74-2.60 (total 1H, m), 2.60-2.43 (total 1H, m), 2.34-2.23 (total 1H, m), 1.94-1.54 (total 3H, m), 1.54-1.41 (total 1H, m), 1.41-1.19 (total 9H, m).

c) Preparation of tert-butyl (1S,3S,4R)-3-[2-(5-{2-[di(propan-2-yl)carbamoyl]-4-fluorophenoxy}pyrimidin-4-yl)-2,7-diazaspiro[3.5]nonane-7-carbonyl]-5-($^2$H$_2$)methylidene-2-azabicyclo[2.2.2]octane-2-carboxylate (Reference Example 41)

The title compound (80 mg) was obtained according to a similar method to Reference example 22 by using (1S,3S,4R)-2-(tert-butoxycarbonyl)-5-($^2$H$_2$)methylidene-2-azabicyclo[2.2.2]octane-3-carboxylic acid (36 mg).

LC-MS; [M+H]$^+$ 693.6/Rt (minutes) 0.99 (Analytical condition A)

Reference Example 42 tert-Butyl 7-[(1S,3S,4R)-2-(tert-butoxycarbonyl)-5-methylidene-2-azabicyclo[2.2.2]octane-3-carbonyl]-2,7-diazaspiro[3.5]nonane-2-carboxylate

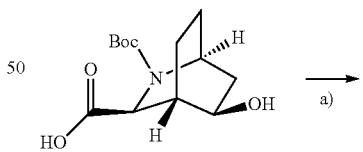

Reference example 5

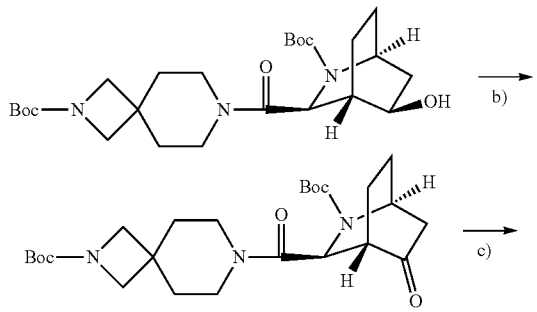

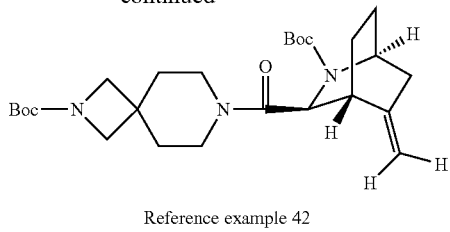

Reference example 42 a) Preparation of tert-butyl 7-[(1S,3S,4S,5R)-2-(tert-butoxycarbonyl)-5-hydroxy-2-azabicyclo[2.2.2]octane-3-carbonyl]-2,7-diazaspiro[3.5]nonane-2-carboxylate To a solution of the compound (20.0 g) obtained in Reference example 5 in dichloromethane (200 mL) were added tert-butyl 2,7-diazaspiro[3.5]nonane-2-carboxylate (18.4 g), WSCl.HCl (18.4 g), HOBt (13.0 g), and N,N-diisopropylethylamine (16.7 mL) at room temperature, and the mixture was stirred at room temperature overnight. To a reaction mixture was added chloroform, and the mixture was washed sequentially with saturated aqueous ammonium chloride, water, and brine. The mixture was dried over anhydrous sodium sulfate, and filtrated. The solvent was removed from the filtrate under reduced pressure, and the resulting residue was crystallized with diisopropyl ether/hexane (1/1) to yield the titled compound (33.9 g).

LC-MS; [M+H]$^+$ 480.1/Rt (mixture) 0.83 (Analytical condition A)

$^1$H-NMR (DMSO-D$_6$) δ: 4.48 and 4.39 (total 1H, each m), 4.27-4.302 (total 2H, m), 3.73-3.25 (total 9H, m), 2.41 and 2.32 (total 1H, each m), 2.15 (1H, br m), 1.98-1.51 (total 10H, m), 1.46-1.42 (total 13H, m), 1.39-1.36 (5H, m).

b) Preparation of tert-butyl 7-[(1S,3S,4S)-2-(tert-butoxycarbonyl)-5-oxo-2-azabicyclo[2.2.2]octane-3-carbonyl]-2,7-diazaspiro[3.5]nonane-2-carboxylate To a solution of oxalyl chloride (8.94 mL) in dichloromethane (300 mL) was added dropwise dimethylsulfoxide (11.1 mL) under a nitrogen atmosphere at −78° C., and the mixture was stirred at −78° C. for 30 minutes. A solution of tert-butyl 7-[(1S,3S,4S,5R)-2-(tert-butoxycarbonyl)-5-hydroxy-2-azabicyclo[2.2.2]octane-3-carbonyl]-2,7-diazaspiro[3.5]nonane-2-carboxylate (25.0 g) in dichloromethane (100 mL) was added dropwise thereto at −65° C. or below, and the mixture was stirred at −78° C. for another hour. Triethylamine (36.3 mL) was added dropwise thereto at −78° C., and the mixture was backed to room temperature and stirred for additional 30 minutes. The reaction mixture was diluted with chloroform, and washed sequentially with saturated aqueous ammonium chloride, water, and brine. The resulting organic layer was dried over anhydrous sodium, and filtrated. The solvent was removed from the filtrate under reduced pressure, and the residue was crystallized with hexane to yield the titled compound (22.5 g).

LC-MS; [M+H]$^+$ 478.1/Rt (minutes) 0.90 (Analytical condition A)

$^1$H-NMR (CDCl$_3$) δ: 4.79 and 4.73 (total 1H, each m), 4.70 and 4.55 (total 1H, each m), 3.74-3.25 (total 8H, m), 2.67-2.29 (total 4H, m), 2.01-1.50 (total 7H, m), 1.50-1.41 (total 12H, m), 1.39 (6H, s).

c) Preparation of tert-butyl 7-[(1S,3S,4R)-2-(tert-butoxycarbonyl)-5-methylidene-2-azabicyclo[2.2.2]octane-3-carbonyl]-2,7-diazaspiro[3.5]nonane-2-carboxylate (Reference Example 42)

To a suspension of methyl(triphenyl)phosphonium bromide (25.2 g) in THF (300 mL) was added potassium tert-butoxide (7.9 g) with ice-cooling, and the mixture was stirred for an hour. To the reaction mixture was added tert-butyl 7-[(1S,3S,4S)-2-(tert-butoxycarbonyl)-5-oxo-2-azabicyclo[2.2.2]octane-3-carbonyl]-2,7-diazaspiro[3.5]nonane-2-carboxylate (22.5 g), and the mixture was stirred at room temperature for 2 hours. Methyl(triphenyl)phosphonium bromide (8.4 g) and potassium tert-butoxide (2.6 g) were further added thereto, and the mixture was stirred at room temperature for another hour. The reaction mixture was diluted with ethyl acetate, and washed with water and brine. The resulting organic layer was dried over anhydrous sodium sulfate, and filtrated. The solvent was removed from the filtrate under reduced pressure, and the residue was purified by silica gel column chromatography (hexane/ethyl acetate) to yield the titled compound (24.2 g).

LC-MS; [M+H]$^+$ 476.1/Rt (minutes) 1.09 (Analytical condition A)

$^1$H-NMR (CDCl$_3$) δ: 4.94 (1H, br s), 4.78 (1H, m), 4.57 and 4.50 (total 1H, each m), 4.38 and 4.23 (total 1H, each br s), 3.77-3.26 (total 8H, m), 2.67-2.49 (total 1H, m), 2.47 and 2.41 (total 1H, each m), 2.38-2.27 (total 1H, m), 2.26-2.13 (total 1H, m), 1.98-1.47 (total 7H, m), 1.47-1.39 (total 12H, m), 1.37 (6H, s).

Example 1

2-[(4-{7-[(1S,3S,4R,6S)-6-(Cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide

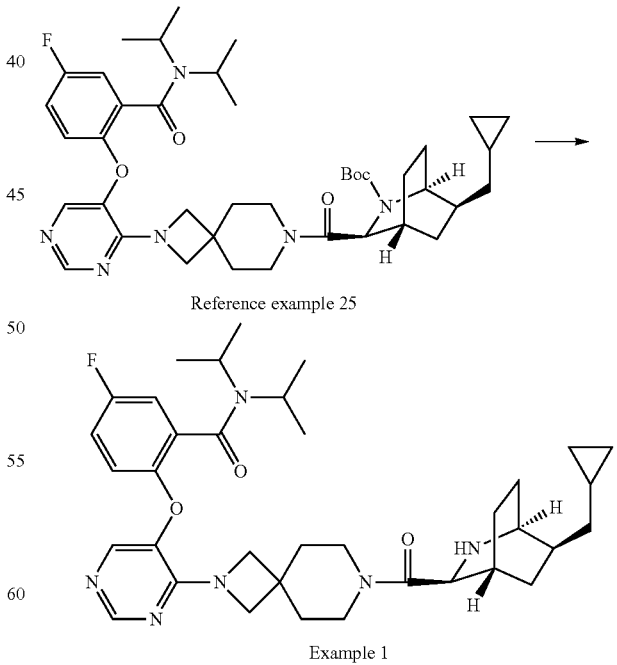

Reference example 25

Example 1

To a solution of tert-butyl (1S,3S,4R,6S)-6-(cyclopropylmethyl)-3-[2-(5-{2-[di(propan-2-yl)carbamoyl]-4-fluorophenoxy}pyrimidin-4-yl)-2,7-diazaspiro[3.5]nonane-7-carbonyl]-2-azabicyclo[2.2.2]octane-2-carboxylate (62 mg) obtained in Reference example 25 in dichloromethane (1 mL) was added TFA (1 mL) at room temperature, and the mixture was stirred at room temperature for an hour. The solvent was removed under reduced pressure, and the residue was purified by amine-silica gel column chromatography (ethyl acetate/methanol) to yield the titled compound (28 mg).

LC-MS; [M+H]$^+$ 633.4/Rt (minutes) 1.64 (Analytical condition B)

$^1$H-NMR (CDCl$_3$) δ: 8.39 (1H, s), 7.80 (1H, d, J=3.1 Hz), 7.02-6.95 (2H, m), 6.74 (1H, m), 4.03 (2H, m), 3.96-3.86 (3H, m), 3.79 (1H, m), 3.67-3.46 (3H, m), 3.30 (2H, brs), 2.85 (1H, brs), 2.16 (1H, m), 2.03 (1H, m), 1.80-1.59 (6H, m), 1.53 (3H, d, J=6.7 Hz), 1.48 (3H, d, J=6.7 Hz), 1.39-1.23 (4H, m), 1.16-1.08 (7H, m), 0.88 (1H, m), 0.68 (1H, m), 0.45-0.37 (2H, m), 0.08-0.03 (2H, m).

Example 2

2-[(4-{7-[(1R,3S,4R)-2-Azabicyclo[2.2.2]octane-3-carbonyl]-2,7-diazaspiro[4.4]nonan-2-yl}pyrimidin-5-yl)oxy]-5-fluoro-N,N-di(propan-2-yl)benzamide

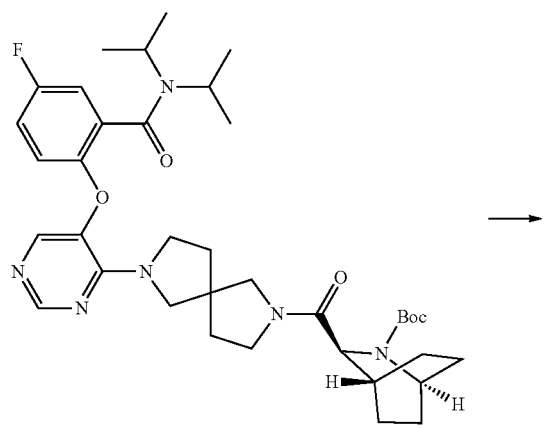

Reference example 24

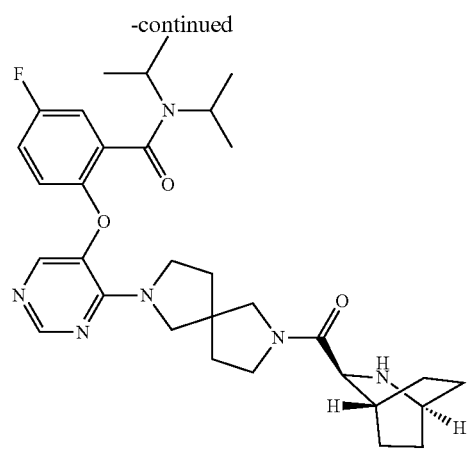

Example 2

The titled compound (89 mg) was prepared according to a similar method to Example 1 by using tert-butyl (1R,3S,4R)-3-[7-(5-{2-[di (propan-2-yl)carbamoyl]-4-fluorophenoxy}pyrimidin-4-yl)-2,7-diazaspiro[4.4]nonane-2-carbonyl]-2-azabicyclo[2.2.2]octane-2-carboxylate (100 mg) obtained in Reference example 24.

LC-MS; [M+H]$^+$ 579.0/Rt (minutes) 1.50 (Analytical condition B)

$^1$H-NMR (CDCl$_3$) δ: 8.34-8.30 (1H, m), 7.85-7.79 (1H, m), 7.22-7.18 (2H, m), 6.89-6.80 (2H, m), 3.72-3.23 (11H, m), 2.87-2.69 (1H, m), 1.87-1.54 (8H, m), 1.44-1.43 (4H, m), 1.35-1.24 (6H, m), 1.08-1.02 (8H, m), 0.88-0.85 (1H, m).

Example 3 to 19

The following compounds of Examples 3 to 19 were prepared according to a similar method to Example 1 by using each corresponding starting compound.

| Example | b | d | E | LC-MS; [M + H]$^+$ or [M + 2H]$^{2+}$/Rt (min) (Analytical condition) $^1$H-NMR: Chemical Shift |
|---|---|---|---|---|
| 3 | 1 | 1 | 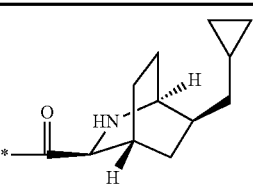 | 605.3/1.60 (Analytical condition B) $^1$H-NMR (DMSO-D$_6$)δ: 8.28 (1H, s), 7.75 (1H, s), 7.23-7.19 (2H, m), 7.03-6.99 (1H, m), 4.36-4.24 (5H, m), 4.04-4.01 (2H, m), 3.67-3.50 (3H, m), 3.31 (4H, brs), 2.62 (1H, brs), 1.93-1.90 (2H, m), 1.67 |

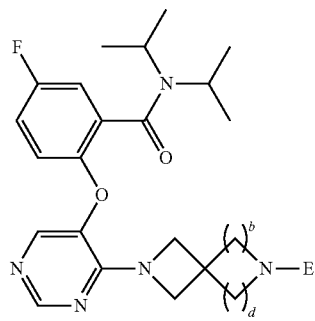

| Example | b | d | E | | LC-MS; [M + H]⁺ or [M + 2H]²⁺/Rt (min) (Analytical condition) $^1$H-NMR: Chemical Shift |
|---|---|---|---|---|---|
| | | | | | (1H, brs), 1.44-1.23 (4H, m), 1.43 (3H, d, J = 6.7 Hz), 1.33 (3H, d, J = 6.7 Hz), 1.08 (3H, d, J = 6.7 Hz), 1.03 (3H, d, J = 6.0 Hz), 0.99 (3H, d, J = 6.7 Hz), 0.67-0.61 (1H, m), 0.38-0.36 (2H, m), 0.01-0.00 (2H, m). |
| 4 | 2 | 2 | 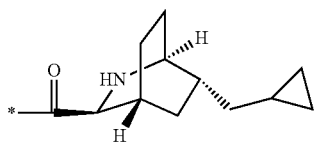 [SMILES: *C(=O)[C@H]1N[C@H]2CC[C@@H]1C[C@H]2CC1CC1] | | 633.4/1.62 (Analytical condition B) $^1$H-NMR (CDCl$_3$)δ: 8.39 (1H, d, J = 1.2 Hz), 7.80 (1H, d, J = 3.7 Hz), 7.01-6.96 (2H, m), 6.74 (1H, m), 4.03 (2H, m), 3.93-3.88 (2H, m), 3.82-3.75 (2H, m), 3.67-3.45 (3H, m), 3.30 (2H, brs), 2.88 (1H, brs), 1.95-1.83 (2H, m), 1.78-1.26 (16H, m), 1.14-1.08 (6H, m), 0.90-0.85 (2H, m), 0.70 (1H, m), 0.43-0.37 (2H, m), 0.08-0.03 (2H, m). |
| 5 | 1 | 1 | 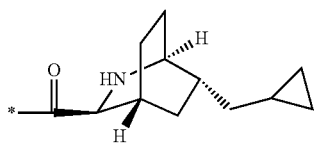 [SMILES: *C(=O)[C@H]1N[C@H]2CC[C@@H]1C[C@H]2CC1CC1] | | 605.4/1.60 (Analytical condition B) $^1$H-NMR (CDCl$_3$)δ: 8.40 (1H, d, J = 1.8 Hz), 7.82 (1H, d, J = 3.7 Hz), 7.00-6.96 (2H, m), 6.69 (1H, m), 4.47-4.06 (8H, m), 3.77 (1H, m), 3.51-3.45 (2H, m), 2.80 (1H, m), 1.96-1.26 (16H, m), 1.14-1.08 (6H, m), 0.89-0.85 (2H, m), 0.68 (1H, m), 0.43-0.37 (2H, m), 0.04 (2H, m). |
| 6 | 2 | 2 | 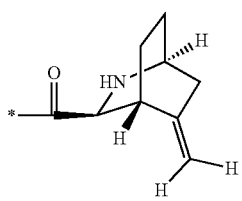 [SMILES: *C(=O)[C@H]1N[C@H]2CC[C@@H]1C(=C)C2] | | 591.2/0.73 (Analytical condition A) $^1$H-NMR (DMSO-D6) δ: 8.25 (1H, s), 7.71 (1H, d, J = 4.3 Hz), 7.22-7.17 (2H, m), 7.01 (1H, m), 4.89 (1H, s), 4.69 (1H, s), 3.93 (2H, brs) 3.85 (1H, brs), 3.83 (2H, brs), 3.66 (1H, m), 3.57-3.46 (2H, m), 3.37 (1H, m), 3.26 (2H, brs), 2.97 (1H, d, J = 3.0 Hz), 2.43 (1H, brm), 2.33 (1H, brm), 2.27 (1H, brs), 2.22 (1H, dd, J = 2.1, 16.8 Hz), 1.70 (2H, brm), 1.63 (3H, brm), 1.57-1.49 (1H, m), 1.41-1.37 (5H, m), 1.31 (3H, d, J = 6.7 Hz), 1.06 (3H, d, J = 6.7 Hz), 0.97 (3H, d, J = 6.7 Hz). |

-continued

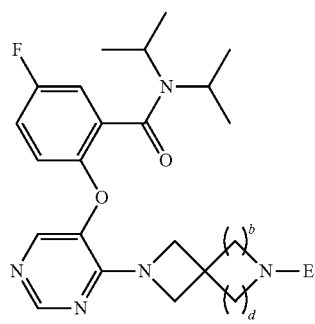

| Example | b | d | E | | LC-MS; [M + H]+ or [M + 2H]²+/Rt (min) (Analytical condition) ¹H-NMR: Chemical Shift |
|---|---|---|---|---|---|
| 7 | 1 | 1 | 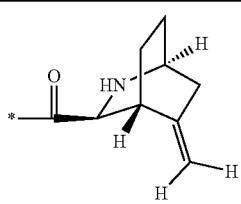 | | 282.6/0.87 (Analytical condition A) ¹H-NMR (DMSO-D$_6$)δ: 8.29 (1H, d, J = 2.4 Hz), 7.76 (1H, d, J = 7.3 Hz), 7.24-7.20 (2H, m), 7.05-7.02 (1H, m), 4.89 (1H, s), 4.69 (1H, s), 4.37-4.26 (5H, m), 4.10-4.05 (2H, m), 3.70-3.66 (1H, m), 3.55-3.51 (2H, m), 3.32 (4H, brs), 2.96 (1H, s), 2.42-2.22 (2H, m), 1.68-1.61 (2H, m), 1.44 (3H, d, J = 6.7 Hz), 1.40-1.25 (2H, m), 1.34 (3H, d, J = 6.7 Hz), 1.09 (3H, d, J = 6.7 Hz), 0.99 (3H, d, J = 6.7 Hz), 0.88-0.84 (1H, m). |
| 8 | 2 | 2 | 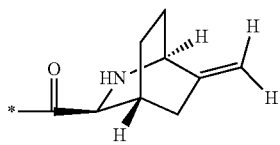 [SMILES: *C(=O)[C@H]1N[C@H]2CC[C@@H]1CC2=C] | | 591.2/0.73 (Analytical condition A) ¹H-NMR (DMSO-D$_6$)δ: 8.26 (1H, s), 7.72 (1H, s), 7.26-7.17 (2H, m), 7.07-6.99 (1H, m), 4.80 (1H, d, J = 1.8 Hz), 4.64 (1H, d, J = 1.8 Hz), 4.04-3.90 (2H, m), 3.90-3.81 (2H, m), 3.79 (1H, s), 3.72-3.60 (1H, m), 3.55-3.27 (5H, m), 3.19 (1H, d, J = 1.8 Hz), 2.55-2.42 (3H, m), 2.36-2.24 (1H, m), 1.87 (1H, s), 1.81-1.55 (5H, m), 1.53-1.37 (5H, m), 1.32 (3H, d, J = 6.1 Hz), 1.07 (3H, d, J = 6.7 Hz), 0.98 (3H, d, J = 6.7 Hz). |
| 9 | 1 | 1 | 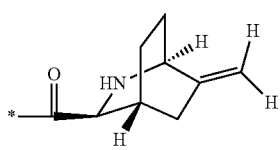 [SMILES: *C(=O)[C@H]1N[C@H]2CC[C@@H]1CC2=C] | | 563.6/1.51 (Analytical condition B) ¹H-NMR (DMSO-D$_6$)δ: 8.29 (1H, s), 7.76 (1H, s), 7.24-7.19 (2H, m), 7.04-7.00 (1H, m), 4.77 (1H, s), 4.62 (1H, s), 4.43-4.23 (5H, m), 4.06-4.02 (2H, m), 3.70-3.49 (3H, m), 3.32 (4H, brs), 3.13 (1H, s), 2.38-2.28 (2H, m), 1.96 (1H, s), 1.80-1.72 (1H, m), 1.54-1.34 (3H, m), 1.44 (3H, d, J = 6.7 Hz), 1.34 (3H, d, J = 6.7 Hz), 1.09 (3H, d, J = 6.0 Hz), 1.03 (1H, d, J = 8.5 Hz), 1.00 (3H, d, J = 6.7 Hz). |

-continued

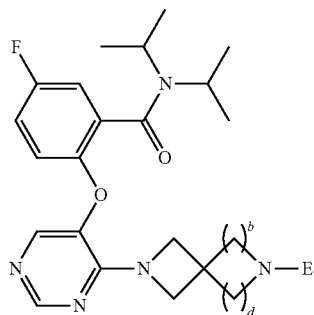

| Example | b | d | E | LC-MS; [M + H]$^+$ or [M + 2H]$^{2+}$/Rt (min) (Analytical condition) $^1$H-NMR: Chemical Shift |
|---|---|---|---|---|
| 10 | 1 | 1 | (structure with F) | 285.2/0.70 (Analytical condition A) $^1$H-NMR (DMSO-D$_6$)δ: 8.27 (1H, s), 7.74 (1H, s), 7.23-7.19 (2H, m), 7.04-7.00 (1H, m), 5.00-4.96 (0.5H, m), 4.85-4.80 (0.5H, m), 4.34-4.24 (5H, m), 4.09-4.03 (2H, m), 3.75 (1H, s), 3.69-3.50 (2H, m), 3.31 (2H, brs), 2.88 (1H, s), 2.06-1.98 (2H, m), 1.77-1.64 (1H, m), 1.52-1.24 (4H, m), 1.43 (3H, d, J = 6.7 Hz), 1.33 (3H, d, J = 6.7 Hz), 1.08 (3H, d, J = 6.7 Hz), 1.03 (1H, d, J = 6.1 Hz), 0.99 (3H, d, J = 4.9 Hz). |
| 11 | 1 | 1 | (structure) | 276.7/0.66 (Analytical condition A) $^1$H-NMR (DMSO-D$_6$)δ: 8.28 (1H, s), 7.76 (1H, s), 7.24-7.20 (2H, m), 7.04-7.00 (1H, m), 4.39-4.23 (6H, m), 4.08-4.02 (2H, m), 3.70-3.66 (1H, m), 3.54-3.51 (2H, m), 3.41-3.32 (2H, m), 2.74 (1H, s), 1.70-1.33 (9H, m), 1.43 (3H, d, J = 6.7 Hz), 1.33 (3H, d, J = 6.7 Hz), 1.11-1.08 (1H, m), 1.08 (3H, d, J = 6.7 Hz), 0.99 (3H, d, J = 6.7 Hz) |
| 12 | 2 | 2 | (structure with =O) | 297.1/0.46 (Analytical condition A) $^1$H-NMR (CDCl$_3$) δ: 8.33 (1H, s), 7.75 (1H, s), 6.95-6.90 (2H, m), 6.72-6.65 (1H, m), 4.40-4.26 (1H, m), 4.11-3.53 (7H, m), 3.50-3.37 (2H, m), 3.29-3.12 (2H, m), 3.05-2.84 (1H, m), 2.50-2.21 (3H, m), 2.11-1.97 (1H, m), 1.90-1.54 (7H, m), 1.47 (3H, d, J = 6.1 Hz), 1.42 (3H, d, J = 6.1 Hz), 1.16-0.99 (6H, m). |
| 13 | 2 | 2 | (structure with =N-OMe) | 622.4/0.53 (Analytical condition A) $^1$H-NMR (CDCl$_3$) δ: 8.37 (1H, s), 7.78 (1H, s), 7.02-6.92 (2H, m), 6.76-6.68 (1H, m), 4.21 (1H, s), 4.13-3.65 (9H, m), 3.56-3.41 (3H, m), 3.39-3.22 (2H, m), 2.93-2.82 (1H, m), 2.58-2.41 (2H, m), 2.02-1.89 (1H, m), 1.89-1.59 (7H, m), 1.59-1.40 (7H, m), 1.20-1.04 (6H, m). |

-continued

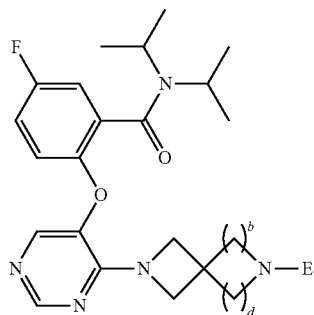

| Example | b | d | E | | LC-MS; [M + H]+ or [M + 2H]²⁺/Rt (min) (Analytical condition) ¹H-NMR: Chemical Shift |
|---|---|---|---|---|---|
| 14 | 2 | 2 | 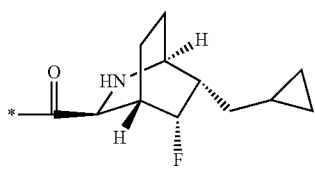 [SMILES: *C(=O)[C@H]1N[C@H]2CC[C@@H]1[C@@H](F)[C@H]2CC1CC1] | | 651.5/0.57 (Analytical condition A) ¹H-NMR (DMSO-D₆) δ: 8.31 (1H, s), 7.77 (1H, s), 7.31-7.23 (2H, m), 7.12-7.05 (1H, m), 5.09-4.89 (1H, m), 4.11-3.85 (5H, m), 3.77-3.65 (1H, m), 3.61-3.44 (3H, m), 3.41-3.23 (3H, m), 2.92 (1H, s), 2.10-1.95 (2H, m), 1.86-1.26 (15H, m), 1.12 (3H, d, J = 6.7 Hz), 1.03 (3H, d, J = 6.7 Hz), 0.82-0.71 (1H, m), 0.51-0.36 (2H, m), 0.18-0.01 (2H, m). |
| 15 | 1 | 1 | 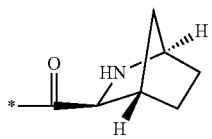 [SMILES: *C(=O)[C@H]1N[C@@H]2CC[C@H]1C2] | | 537.4/1.48 (Analytical condition B) ¹H-NMR (DMSO-D₆)δ: 8.28 (1H, s), 7.75 (1H, s), 7.23-7.19 (2H, m), 7.03-7.00 (1H, m), 4.39-4.22 (5H, m), 4.01-3.98 (2H, m), 3.69-3.51 (2H, m), 3.35-3.31 (4H, m), 3.06 (1H, s), 2.42 (1H, s), 1.47-0.99 (8H, m), 1.43 (3H, d, J = 6.7 Hz), 1.33 (3H, d, J = 6.7 Hz), 1.08 (3H, d, J = 6.7 Hz), 1.03 (3H, d, J = 6.7 Hz) |
| 16 | 2 | 2 | 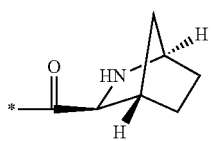 | | 565.7/1.58 (Analytical condition B) ¹H-NMR (DMSO-D₆)δ: 8.28 (1H, s), 7.75 (1H, s), 7.26-7.21 (2H, m), 7.05-7.02 (1H, m), 3.98-3.38 (12H, m), 2.53 (1H, s), 1.78-1.58 (8H, m), 1.43 (3H, d, J = 6.7 Hz), 1.35-1.33 (2H, s), 1.34 (3H, d, J = 6.7 Hz), 1.08 (3H, d, J = 6.7 Hz), 0.98 (3H, d, J = 6.7 Hz) |
| 17 | 2 | 2 | 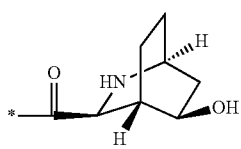 [SMILES: *C(=O)[C@H]1N[C@H]2CC[C@@H]1[C@H](O)C2] | | 595.2/1.47 (Analytical condition B) ¹H-NMR (DMSO-D₆)δ: 8.28 (1H, s), 7.74 (1H, s), 7.25-7.22 (2H, m), 7.06-7.04 (1H, m), 4.67 (s, 1H), 4.01-3.86 (5H, m), 3.74 (1H, s), 3.73-3.62 (1H, m), 3.32-3.30 (4H, m), 2.78 (1H, s), 2.10-2.04 (1H, m), 1.80-1.48 (6H, m), 1.44-1.40 (1H, m), 1.43 (3H, d, J = 6.7 Hz), 1.34 (3H, d, J = 6.7 Hz), 1.26-1.18 (2H, s), 1.08 (3H, d, J = 6.7 Hz), 0.98 (3H, d, J = 6.7 Hz) |

-continued

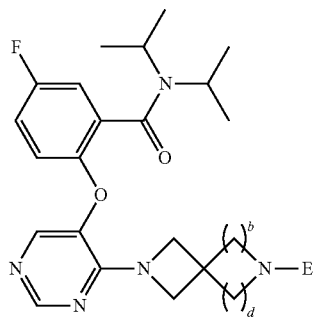

| Example | b | d | E | LC-MS; [M + H]+ or [M + 2H]2+/Rt (min) (Analytical condition) 1H-NMR: Chemical Shift |
|---|---|---|---|---|
| 18 | 2 | 2 | 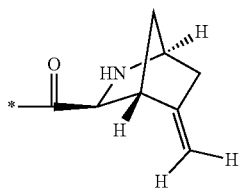 [SMILES: *C(=O)[C@H]1N[C@@H]2CC(=C)[C@H]1C2] | 577.0/1.56 (Analytical condition B) 1H-NMR (DMSO-D6)δ: 8.28 (1H, s), 7.74 (1H, s), 7.25-7.21 (2H, m), 7.05-7.04 (1H, m), 5.01 (s, 1H), 4.67 (s, 1H), 3.87-3.85 (2H, m), 3.71-3.64 (1H, m), 3.55-3.48 (3H, m), 3.39-3.31 (5H, m), 2.86 (1H, s), 2.14-1.98 (2H, m), 1.77-1.65 (4H, m), 1.43 (3H, d, J = 6.7 Hz), 1.35-1.32 (3H, m), 1.34 (3H, d, J = 6.7 Hz), 1.08 (3H, d, J = 6.7 Hz), 0.98 (3H, d, J = 6.7 Hz), 0.86-0.85 (1H, m). |
| 19 | 2 | 2 | | 651.4/1.67 (Analytical condition 8) 1H-NMR (DMSO-D6)δ: 8.27 (1H, s), 7.73 (1H, s), 7.25-7.21 (2H, m), 7.07-7.03 (1H, m), 4.55 (s, 1H), 4.42 (s, 1H), 4.03-3.85 (5H, m), 3.70-3.65 (1H, m), 3.53-3.49 (1H, m), 3.26-3.24 (2H, m), 2.81 (1H, s), 2.04-1.94 (2H, m), 1.71-1.65 (2H, m), 1.43 (3H, d, J = 6.7 Hz), 1.42-1.32 (2H, m), 1.34 (3H, d, J = 6.7 Hz), 1.19-1.17 (1H, m), 1.08 (3H, d, J = 6.7 Hz), 0.98 (3H, d, J = 6.7 Hz), 0.86-0.85 (1H, m), 0.44-0.42 (2H, m), 0.08-0.04 (2H, m). |

Example 20
5-Fluoro-2-[(4-{7-[(1S,3S,4R)-5-($^2$H$_2$)methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide

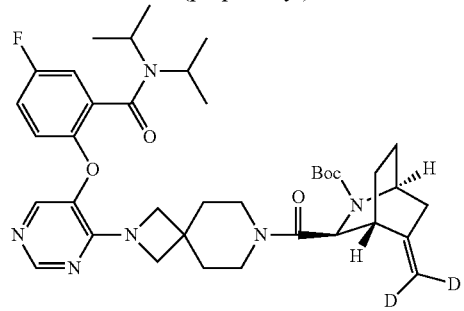

Reference example 41

→

-continued

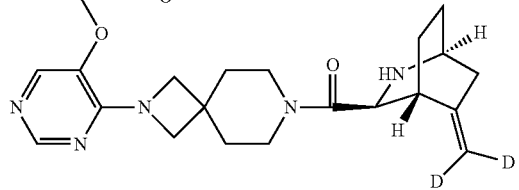

Example 20

The titled compound (23 mg) was prepared according to a similar method to Example 1 by using tert-butyl (1S,3S,4R)-3-[2-(5-{(2-[di(propan-2-yl)carbamoyl]-4-fluorophenoxy}pyrimidin-4-yl)-2,7-diazaspiro[3.5]nonane-7-carbonyl]-5-($^{2}$H$_{2}$)methylidene-2-azabicyclo[2.2.2]octane-2-carboxylate (80 mg) obtained in Reference example 41.

LC-MS; [M+H]$^{+}$ 593.6/Rt (minutes) 0.70 (Analytical condition A)

$^{1}$H-NMR (DMSO-D6) δ: 8.27 (1H, s), 7.73 (1H, d, J=4.1 Hz), 7.26-7.16 (2H, m), 7.03 (1H, m), 4.05-3.90 (total 3H, brs), 3.87 (2H, m), 3.67 (1H, m), 3.57-3.45 (2H, m), 3.45-3.19 (total 3H, m), 3.07 (1H, s), 2.52 (1H, brs), 2.33 (1H, brs), 2.27 (1H, dd, J=2.5, 17.1 Hz), 1.79-1.60 (total 5H, brm), 1.55 (1H, m), 1.48-1.37 (5H, m), 1.33 (3H, d, J=6.9 Hz), 1.07 (3H, d, J=6.4 Hz), 0.98 (3H, d, J=6.4 Hz).

Example 21

2-[(4-{7-[(1S,3S,4R,6R)-6-(Cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide mono-L-(+)-tartrate Example 22

2-[(4-{7-[(1S,3S,4R,6R)-6-(Cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide Monohydrochloride Example 22

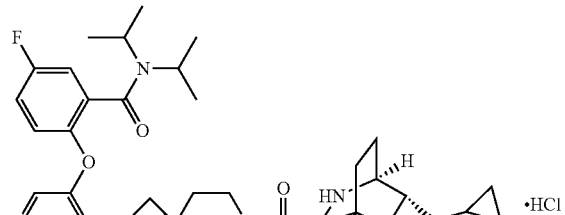

Example 21

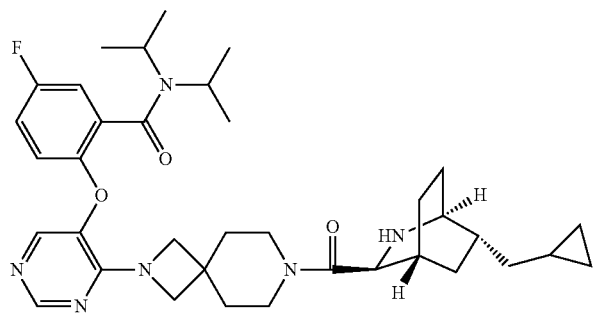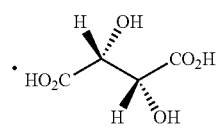

To a solution of the compound (0.50 g) of Example 4 in ethyl acetate/ethanol (10/1, 11 mL) was added L(+)-tartaric acid (0.11 g), and the mixture was stirred at room temperature for 3 days. The precipitated solid was filtered, washed with ethyl acetate, and dried under reduced pressure to yield the titled compound (0.54 g) as a crystal (crystal form I).

$^{1}$H-NMR (400 MHz, DMSO-d$_{6}$) δ: 8.27 (1H, s), 7.74 (1H, s), 7.26-7.18 (2H, m), 7.04 (1H, m), 4.27 (1H, br s), 3.96 (2H, br s), 3.91-3.80 (total 4H, m), 3.67 (1H, m), 3.57-3.43 (3H, m), 3.38 (2H, br s), 3.29 (1H, br s), 1.94 (1H, br s), 1.91-1.78 (3H, m), 1.70 (4H, br m), 1.62-1.20 (total 12H, m), 1.07 (3H, d, J=6.1 Hz), 0.97 (3H, d, J=6.1 Hz), 0.68 (1H, m), 0.40 (2H, m), 0.07 (2H, m).

(Crystal form I) A powder X-ray diffraction pattern was shown in FIG. 1.

Main diffraction peak: 2θ (°)=5.3, 8.0, 11.2, 13.0, 13.5, 15.9, 16.4, 17.5, 17.9, 18.2, 20.0

Distinctive diffraction peak: 2θ (°)=5.3, 11.2, 13.0, 15.9, 17.9, 18.2

To a solution of the compound (50 mg) of Example 4 in ethyl acetate (1 mL) was added 4 mol/L hydrochloric acid/ethyl acetate (19 μL), and the mixture was stirred at room temperature for 4 hours. The precipitated solid was filtered, washed with ethyl acetate, and dried under reduced pressure to yield the titled compound (30 mg) as a crystal (crystal form II).

$^{1}$H-NMR (400 MHz, DMSO-d$_{6}$) δ: 8.27 (1H, s), 7.75 (1H, d, J=1.8 Hz), 7.26-7.19 (2H, m), 7.04 (1H, m), 4.36 (1H, br s), 4.07-3.92 (2H, br s), 3.92-3.81 (2H, m), 3.67 (1H, m), 3.61-3.46 (3H, m), 3.45-3.36 (3H, m), 2.00 (1H, br s), 1.96-1.80 (3H, m), 1.79-1.21 (total 16H, m), 1.08 (3H, d, J=6.9 Hz), 0.97 (3H, d, J=6.4 Hz), 0.68 (1H, m), 0.41 (2H, m), 0.09 (2H, m).

Figure 2:
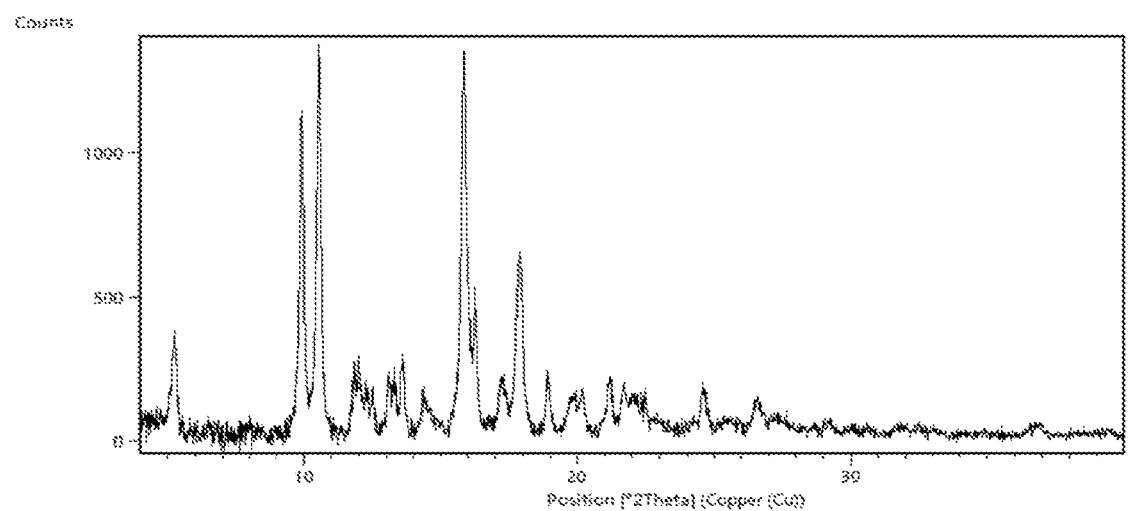
FIG. 2 shows a powder X-ray diffraction pattern of crystal form II of the compound of Example 22.

(Crystal form II) A powder X-ray diffraction pattern is shown in FIG. 2.

Main diffraction peak: 2θ (°)=5.3, 9.9, 10.6, 11.9, 13.1, 13.6, 15.9, 16.3, 17.9, 18.9, 21.2

Distinctive diffraction peak: 2θ (°)=5.3, 9.9, 10.6, 15.9, 16.3, 17.9

Example 23

2-[(4-{7-[(1S,3S,4R,6R)-6-(Cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide Dihydrochloride Example 23

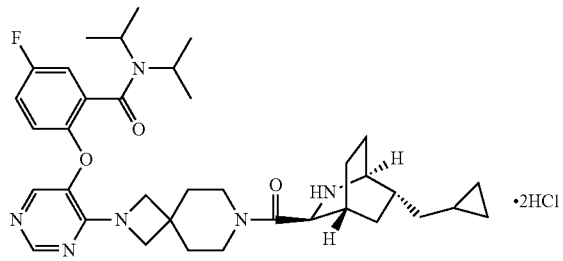

·2HCl

To a solution of the compound (0.50 g) of Example 4 in ethyl acetate/ethanol (10/1, 11 mL) was added 4 mol/L hydrochloric acid/ethyl acetate (0.38 mL), and the mixture was stirred at room temperature for 3 days. The precipitated solid was filtered, washed with ethyl acetate, and dried under reduced pressure to yield dihydrochloride of the compound of Example 4 (0.49 g) as a crystal (crystal form III).

$^1$H-NMR (400 MHz, DMSO-$d_6$) δ: 9.22 (1H, br s), 8.53 (1H, s), 8.03 (1H, br d, J=12.8 Hz), 7.85 (1H, br s), 7.36-7.25 (3H, m), 4.40 (1H, br s), 4.34-3.97 (total 4H, br m), 3.67 (1H, m), 3.59-3.47 (3H, m), 3.46-3.37 (3H, m), 2.01 (1H, br s), 1.96-1.82 (3H, m), 1.75 (4H, br s), 1.66-1.27 (total 12H, m), 1.09 (3H, d, J=6.7 Hz), 0.93 (3H, d, J=6.7 Hz), 0.67 (1H, m), 0.40 (2H, m), 0.10 (2H, m).

Figure 3:
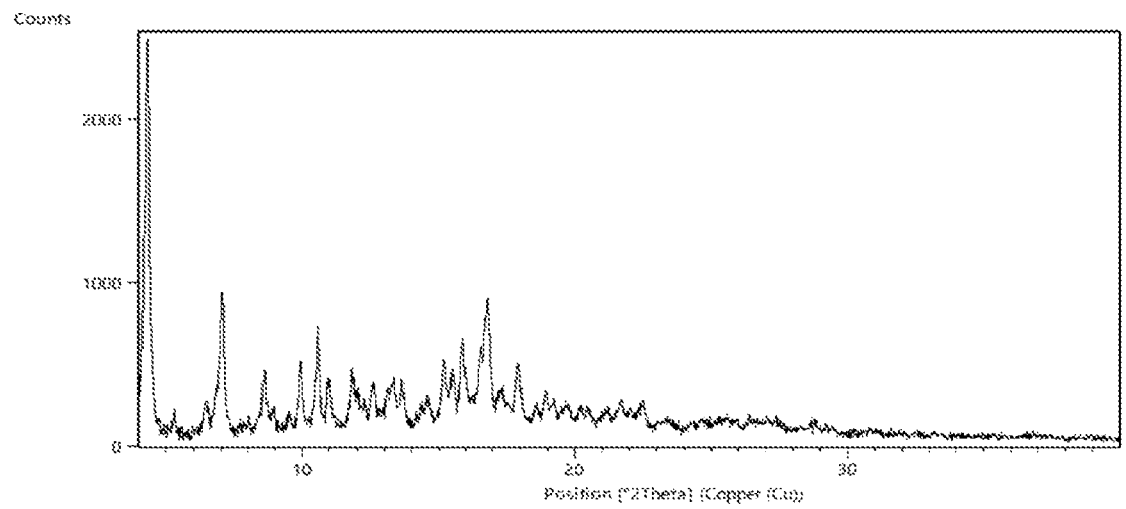
FIG. 3 shows a powder X-ray diffraction pattern of crystal form III of the compound of Example 23.

(Crystal form III) A powder X-ray diffraction pattern is shown in FIG. 3.

Main diffraction peak: 2θ (°)=4.3, 7.0, 9.9, 10.6, 11.8, 15.2, 15.5, 15.9, 16.5, 16.8, 17.9

Distinctive diffraction peak: 2θ (°)=4.3, 7.0, 10.6, 15.9, 16.5, 16.8

Example 6

5-Fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide

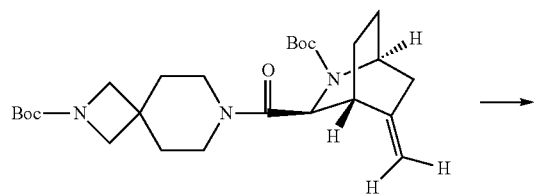

Reference example 42

→

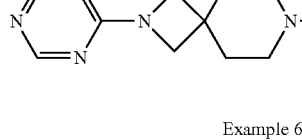

Example 6

Example 6 can also be prepared by the following procedure. To a solution of tert-butyl 7-[(1S,3S,4R)-2-(tert-butoxycarbonyl)-5-methylidene-2-azabicyclo[2.2.2]octane-3-carbonyl]-2,7-diazaspiro[3.5]nonane-2-carboxylate (7.0 g) obtained in Reference example 42 in chloroform (11 mL) was added dropwise TFA (11 mL) at room temperature, and the mixture was stirred at room temperature overnight. The reaction mixture was concentrated under reduced pressure, diluted with acetonitrile (70 mL), and 5 mol/L aqueous sodium hydroxide (28 mL) was added dropwise thereto with ice cooling. 2-[(4-Chloropyrimidin-5-yl)oxy]-5-fluoro-N,N-di(propan-2-yl)benzamide (4.9 g) obtained in Reference example 1 was added thereto, and the mixture was stirred at room temperature for 5 hours. To the reaction was added water (200 mL), and the precipitated solid was filtered, and washed with water. The solid was dried under reduced pressure to yield the titled compound (7.3 g).

Example 24

5-Fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide mono-L(+)-tartrate Example 24

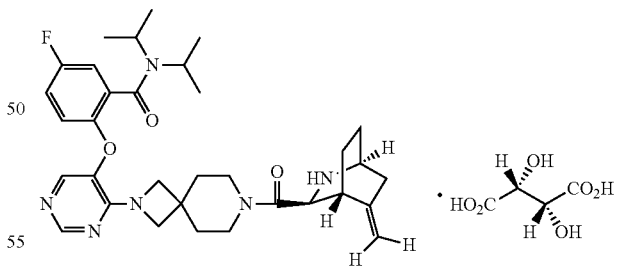

To a solution of the compound (2.0 g) of Example 6 in THF (5 mL) was added L(+)-tartaric acid (0.48 g), and the mixture was stirred at 60° C. for an hour. After cooling, the precipitated solid was filtered, washed with ethyl acetate, and dried under reduced pressure to yield the titled compound (2.0 g) as a crystal (crystal form IV).

$^1$H-NMR (400 MHz, DMSO-$d_6$) δ: 8.28 (1H, s), 7.73 (1H, d, J=5.5 Hz), 7.26-7.17 (2H, m), 7.02 (1H, m), 5.08 (1H, s), 4.85 (1H, s), 4.32 (1H, s), 4.06-3.83 (total 6H, m), 3.68 (1H, m), 3.63-3.39 (total 4H, m), 3.32 (2H, br s), 2.66 (1H, m), 2.54 (1H, br s), 2.39 (1H, m), 1.91-1.64 (total 5H, m), 1.60-1.47 (3H, m), 1.42 (3H, d, J=6.9 Hz), 1.33 (3H, d, J=6.4 Hz), 1.08 (3H, d, J=6.9 Hz), 0.98 (3H, d, J=6.4 Hz).

Figure 4:
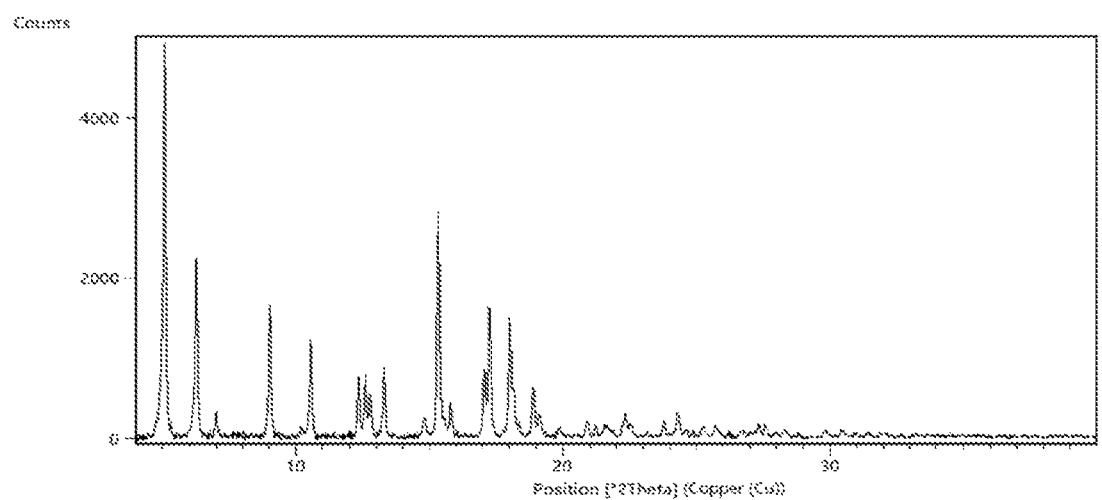
FIG. 4 shows a powder X-ray diffraction pattern of crystal form IV of the compound of Example 24.

(Crystal form IV) A powder X-ray diffraction pattern is shown in FIG. 4.

Main diffraction peak: 2θ (°)=5.1, 6.3, 9.0, 10.5, 12.3, 12.6, 13.3, 15.3, 17.1, 17.2, 18.0

Distinctive diffraction peak: 2θ (°)=5.1, 6.3, 9.0, 15.3, 17.2, 18.0

Example 25

5-Fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide Disuccinate

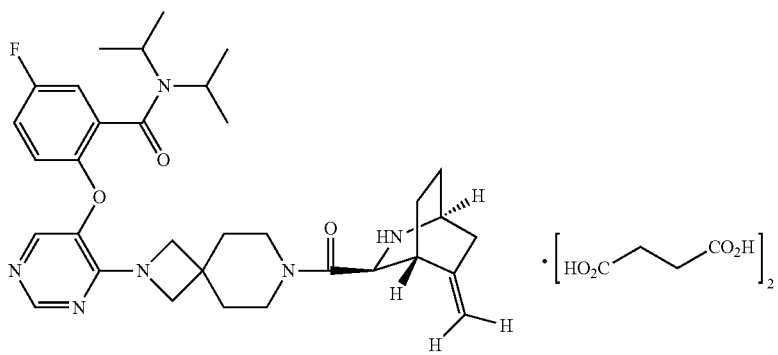

Example 25

To a solution of the compound of Example 6 (2.0 g) in ethyl acetate (8 mL) was added succinic acid (0.78 g), and the mixture was stirred at 60° C. for an hour. After cooling, the precipitated solid was filtered, washed with ethyl acetate, and dried under reduced pressure to yield the titled compound (1.9 g) as a crystal (crystal form V).

$^1$H-NMR (400 MHz, DMSO-$d_6$) δ: 8.27 (1H, s), 7.75 (1H, d, J=4.6 Hz), 7.25-7.18 (2H, m), 7.06 (1H, m), 5.03 (1H, s), 4.81 (1H, s), 4.81 (1H, s), 3.96 (2H, br s), 3.87 (2H, br d, J=9.1 Hz), 3.68 (1H, m), 3.60-3.37 (total 3H, m), 3.31 (3H, br s), 2.59 (1H, br d, J=17.4 Hz), 2.47 (1H, br s), 2.40-2.27 (total 9H, m), 1.85-1.62 (total 5H, m), 1.57-1.45 (total 3H, m), 1.42 (3H, d, J=6.9 Hz), 1.33 (3H, d, J=6.4 Hz), 1.08 (3H, d, J=6.4 Hz), 0.98 (3H, d, J=6.9 Hz).

Figure 5:
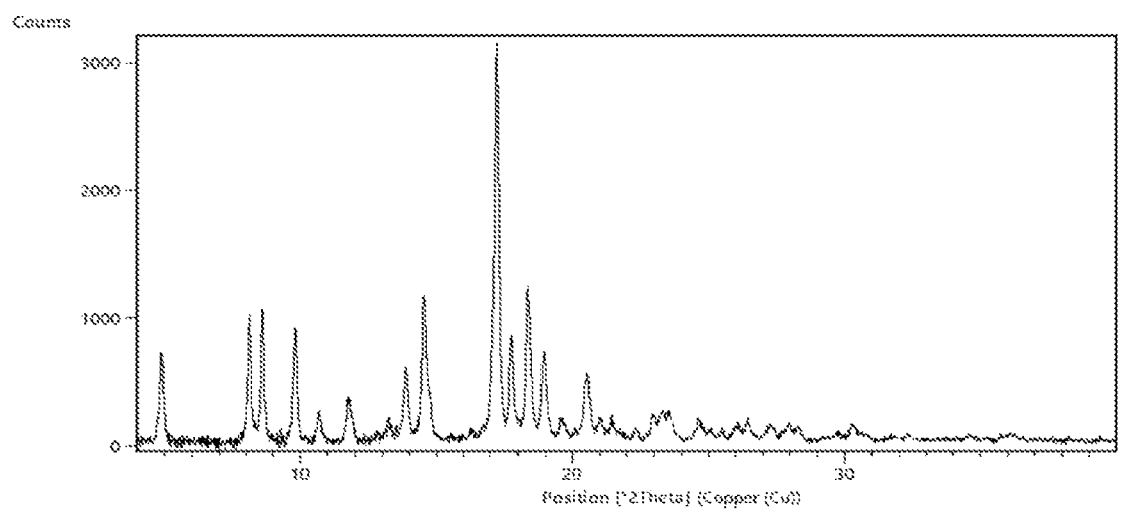
FIG. 5 shows a powder X-ray diffraction pattern of crystal form V of the compound of Example 25.

(Crystal form V) A powder X-ray diffraction pattern is shown in FIG. 5.

Main diffraction peak: 2θ (°)=4.9, 8.1, 8.6, 9.8, 13.9, 14.5, 17.2, 17.8, 18.4, 19.0, 20.5

Distinctive diffraction peak: 2θ (°)=8.1, 8.6, 9.8, 14.5, 17.2, 17.8, 18.4

TESTS

Test 1: Test for Evaluating the Inhibition of the Menin-MLL Binding

Menin$_{1-615}$ wherein 6×His tag and HA tag are inserted in the N-terminus, and myc tag is inserted in the C-terminus (hereinafter, referred to as His-Menin$_{1-615}$), is diluted with an assay buffer (25 mmol/L HEPES, 150 mmol/L NaCl, 1 mmol/L dithiothreitol, 0.5% (w/v) Tween 80, 0.3% (w/v) BSA, 0.3% (w/v) skim milk) to adjust the final concentration to 30 nmol/L. The test compounds are also diluted with the assay buffer to adjust each concentration of the test compounds to 0.005 to 5 μmol/L. The prepared His-Menin$_{1-615}$ and test compounds were added to a light-shielding 384-well low-volume plate (Corning, #4514) in 2 μL/well and 6 μL/well, respectively, and the plate was covered with a lid for light-shielding (Corning, #3935), and incubated at room temperature for 3 hours. After the incubation, MLL$_{1-172}$ wherein FLAG tag is inserted in the C-terminus (MLL$_{1-172}$-FLAG), was separately diluted with the assay buffer to adjust the final concentration to 50 nmol/L. The prepared MLL$_{1-172}$-FLAG was added to the above plate in 2 μL/well, and the plate was covered with a lid for light-shielding and incubated at room temperature for an hour.

Then, anti-6HIS-d2 antibody (cisbio, 61HISDLA) and anti-FLAGM2-K antibody (cisbio, 61FG2KLA) were diluted with an antibody dilution buffer (50 mmol/L Tris, 150 mmol/L NaCl, 800 mmol/L KF, pH 7.4) to adjust the final concentration to 1.4 μg/mL to prepare an antibody mixture. The prepared antibody mixture was added to the above plate in 10 μL/well, and the plate was covered with a lid and incubated at 4° C. for 17 to 24 hours. After the incubation, the signal was detected with RUBYstar (BMG LABTECH). The binding inhibition rate (%) at each concentration of the test compounds was calculated from the following formula, and the IC$_{50}$ value was obtained, that corresponds to the concentration of the test compound at which the binding inhibition rate is 50%.

Binding inhibition rate (%)={1−(A−C)/(B−C)}×100

A: Signal in the presence of test compound
B: Signal of negative control (in the absence of test compound)
C: Signal of positive control (in the presence of known compound at the concentration which shows 100% inhibition ratio)

The results of the evaluation in Test 1 are shown in the following table.

| Example | HTRF IC$_{50}$ (nM) |
|---|---|
| 1 | 5.3 |
| 2 | — |
| 3 | <3.0 |
| 4 | 7.1 |
| 5 | 4.1 |
| 6 | <3.0 |
| 7 | <3.0 |
| 8 | 7.9 |

-continued

| Example | HTRF IC$_{50}$ (nM) |
|---|---|
| 9 | 6.2 |
| 10 | <3.0 |
| 11 | 7.0 |
| 12 | — |
| 13 | — |
| 14 | — |
| 15 | — |
| 16 | — |
| 17 | — |
| 18 | — |
| 19 | — |
| 20 | — |

The compounds of Examples 1, 3, 4, 5, 6, 7, 8, 9, 10, and 11 showed potent Menin-MLL binding inhibition activity as shown in the above table. Among them, the compounds of Examples 3, 6, 7, and 10 showed particularly potent Menin-MLL binding inhibition activity.

Test 2: Test for Evaluating the Inhibition of Cell Proliferation

RS4; 11 cells were obtained from American Type Culture Collection (ATCC). The cells were cultured at 37° C. in the presence of 5% CO$_2$ in RPMI 1640 medium containing 10% fetal bovine serum and 1% penicillin/streptomycin. MOLM-13 cells were separately obtained from DSMZ (Deutsche Sammlung von Mikroorganismen und Zellkulturen GmbH). The cells were cultured at 37° C. in the presence of 5% CO$_2$ in RPMI 1640 medium containing 20% fetal bovine serum and 1% penicillin/streptomycin.

The cells were plated to a 96-well plate in 2000 cells/well, each test compound was added thereto to adjust the final concentration of DMSO to 0.1% of DMSO, and the cells were cultured for 7 days. After the cultivation, the cell viability was calculated with PrestoBlue™ Cell Viability Reagent (Invitrogen, A13261). The IC$_{50}$ value was calculated from a survival curve that corresponds to the concentration of the test compound at which the cell proliferation inhibition rate is 50%.

The results of the evaluation in Test 2 are shown in the following table.

| | IC$_{50}$ (µM) | |
|---|---|---|
| Example | RS4; 11 | MOLM-13 |
| 1 | <0.01 | 0.02 |
| 2 | 0.87 | 0.81 |
| 3 | 0.03 | 0.01 |
| 4 | 0.04 | 0.07 |
| 5 | 0.02 | 0.03 |
| 6 | 0.02 | 0.03 |
| 7 | 0.01 | 0.03 |
| 8 | 0.09 | 0.11 |
| 9 | 0.08 | 0.08 |
| 10 | 0.02 | 0.03 |
| 11 | 0.02 | 0.03 |
| 12 | 0.25 | 0.25 |
| 13 | 2.40 | >3.00 |
| 14 | 0.02 | 0.04 |
| 15 | 0.02 | 0.02 |
| 16 | 0.03 | 0.04 |
| 17 | >3.00 | 1.60 |
| 18 | 0.02 | 0.04 |
| 19 | <0.01 | <0.01 |
| 20 | — | <0.03 |

The compounds of Examples 1, 3, 4, 5, 6, 7, 8, 9, 10, 11, 14, 15, 16, 18, 19, and 20 showed the potent cell proliferation inhibition activity as shown in the above table.

Test 3: Test for the Inhibition of mRNA Transcription with Test Compounds

MV4; 11 cells were obtained from American Type Culture Collection (ATCC). The cells were cultured at 37° C. in the presence of 5% CO$_2$ in RPMI 1640 medium containing 10% fetal bovine serum and 1% penicillin/streptomycin. To the MV4; 11 cells was added each test compound to adjust the final concentration to 1 µmol/L, and the cells were cultured at 37° C. in the presence of 5% CO$_2$ for 20 to 24 hours. After the incubation, the total RNA was extracted from the cells with RNeasy™ Mini Kit (QIAGEN, 74106), and cDNA was synthesized with Superscript™ VILO™ cDNA Synthesis Kit (Invitrogen, #11754250). By using TaqMan™ Gene Expression Master Mix (Applied Biosystems, 4369016) and TaqMan™ probe (Applied Biosystems), the expression level of mRNA was quantified from the obtained cDNA with 7900HT (Applied Biosystems). The expression level of each obtained gene (MEIS1 and HOXA9) was fitted with the expression level of mRNA of GAPDH.

The results of the evaluation in Test 3 are shown in the following table.

| | mRNA at 1 µM (% control) | |
|---|---|---|
| Example | MEIS1 | HOXA9 |
| 1 | 11.8 | 40.2 |
| 2 | — | — |
| 3 | 11.9 | 39.6 |
| 4 | 18.0 | 43.7 |
| 5 | 15.5 | 42.6 |
| 6 | 15.1 | 39.3 |
| 7 | 12.7 | 37.9 |
| 8 | 17.1 | 40.1 |
| 9 | 17.0 | 41.2 |
| 10 | 13.3 | 37.4 |
| 11 | 13.1 | 36.5 |
| 12 | — | — |
| 13 | — | — |
| 14 | — | — |
| 15 | — | — |
| 16 | — | — |
| 17 | — | — |
| 18 | — | — |
| 19 | — | — |
| 20 | — | — |

The compounds of Examples 1, 3, 4, 5, 6, 7, 8, 9, 10, and 11 showed the mRNA transcription inhibition activity which is caused by the binding inhibition of Menin and a MLL fusion protein. Especially, the compound of Example 5 showed an excellent cell proliferation inhibitory activity.

Test 4: Test for the hERG Inhibition

To a cultured CHO cell strain which stably expresses hERG (human Ether-a-go-go Related Gene) was added each test compound to adjust the final concentration to 0.0135 to 0.5% of DMSO. The hERG current was measured with QPatch HT (Sophion Inc.), and the concentration at which 50% of the hERG current was inhibited by each test compound (IC$_{50}$ value; µM) was calculated.

The compounds of Examples were tested according to Test example 4. And, the hERG/RS4; 11 was calculated by dividing the compound concentration obtained in Test example 4, at which 50% of the hERG current is inhibited, by the compound concentration obtained in Test example 2, at which 50% of the proliferation of RS4; 11 cells is inhibited. The results are shown in the following table.

| Example | hERG inhibition IC$_{50}$ (μM) | hERG/RS4; 11 |
| --- | --- | --- |
| 1 | 4.0 | >400 |
| 2 | 11.8 | 13.6 |
| 3 | 6.2 | 620 |
| 4 | 5.8 | 145 |
| 5 | 7.9 | 395 |
| 6 | 51.9 | 2595 |
| 7 | >100 | >10000 |
| 8 | 12.3 | 137 |
| 9 | >10 | >125 |
| 10 | >10 | >500 |
| 11 | >10 | >500 |
| 12 | >100 | >400 |
| 13 | — | — |
| 14 | 11.7 | 557 |
| 15 | >100 | >6250 |
| 16 | >100 | >3571 |
| 17 | >100 | — |
| 18 | 46.1 | >2095 |
| 19 | 6.9 | >690 |
| 20 | 74.8 | — |

As shown in the above table, there is a more than 100-fold gap between the concentration at which 50% of the proliferation of RS4; 11 cells was inhibited and the concentration at which 50% of the hERG current was inhibited in the compounds of Examples 1, 3, 4, 5, 6, 7, 8, 9, 10, 11, 12, 14, 15, 16, 18, and 19. Especially, it is proved that there is a more than 1000-fold excellent gap between the concentration at which 50% of the proliferation of RS4; 11 cells was inhibited and the concentration at which 50% of the hERG current was inhibited in the compounds of Examples 6, 7, 15, 16, and 18.

INDUSTRIAL APPLICABILITY

The compounds of the present invention can inhibit the binding of a MLL fusion protein and menin to provide the antitumor effect.

The invention claimed is:

1. A compound, which is one of
2-[(4-{7-[1S,3S,4R,6R)-6-(cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide,
5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide and
5-fluoro-2-[(4-{7-[(1S,3S,4R)-5-($^2$H$_2$)methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide,
or a pharmaceutically acceptable salt, hydrate, or solvate thereof.

2. The compound of claim 1, wherein the compound is 2-[(4-{7-[(1S,3S,4R,6R)-6-(cyclopropylmethyl)-2-azabicyclo[2.2.2]octane-3-carbonyl]-2,7-diazaspiro[3.5]nonan-2-yl}pyrimidin-5-yl)oxy]-5-fluoro-N,N-di(propan-2-yl)benzamide, or a pharmaceutically acceptable salt thereof.

3. The compound of claim 1, wherein the compound is 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide, or a pharmaceutically acceptable salt thereof.

4. The compound of claim 1, wherein the compound is 5-fluoro-2-[(4-{7-[(1S,3S,4R)-5-($^2$H$_2$)methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide, or a pharmaceutically acceptable salt thereof.

5. The compound of claim 1, wherein the compound is 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide mono-L(+)-tartrate.

6. A pharmaceutical composition, comprising:
one or more of the compound of claim 1; and
at least one member selected from the group consisting of an excipient, a disintegrant, a binder, a fluidizer, a lubricant, a coating agent, a solubilizer, a solubilizing adjuvant, a thickener, a dispersant, a stabilizing agent, a sweetening agent, and a flavor.

7. The pharmaceutical composition of claim 6, comprising fluoro-2-[(4-{7-[1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide.

8. The pharmaceutical composition of claim 6, comprising 5-fluoro-2-[(4-{7-[(1S,3S,4R)-5-($^2$H$_2$)methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide or a pharmaceutically acceptable salt thereof.

9. The pharmaceutical composition of claim 6, comprising 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide or a hydrate or solvate thereof.

10. The pharmaceutical composition of claim 6, comprising 5-fluoro-2-[(4-{7-[(1S,3S,4R)-5-($^2$H$_2$)methylidene-2-azabicyclo[2.2.2]octane-3-carbonyl]-2,7-diazaspiro[3.5]nonan-2-yl}pyrimidin-5-yl)oxy]-N,N-di(propa-2-yl)benzamide or a pharmaceutically acceptable salt, hydrate, or solvate thereof.

* * * * *